US005846765A

United States Patent [19]

Matthews et al.

[11] Patent Number: 5,846,765

[45] Date of Patent: Dec. 8, 1998

[54] IDENTIFICATION OF NOVEL SUBSTRATES

[75] Inventors: David J. Matthews, San Francisco; James A. Wells, Burlingame; Mark J. Zoller, San Francisco, all of Calif.

[73] Assignee: Genentech, Inc., South San Francisco, Calif.

[21] Appl. No.: 441,871

[22] Filed: May 16, 1995

Related U.S. Application Data

[62] Division of Ser. No. 418,928, Apr. 5, 1995, which is a continuation of Ser. No. 161,692, Dec. 3, 1993, abandoned, which is a continuation of Ser. No. 864,452, Apr. 6, 1992, abandoned, which is a continuation-in-part of Ser. No. 50,058, Apr. 30, 1993, Pat. No. 5,750,373, which is a continuation-in-part of Ser. No. 743,614, Aug. 9, 1991, abandoned, which is a continuation-in-part of Ser. No. 715,300, Jun. 14, 1991, abandoned, which is a continuation-in-part of Ser. No. 683,400, Apr. 10, 1991, abandoned, which is a continuation-in-part of Ser. No. 621,667, Dec. 3, 1990, abandoned.

[51] Int. Cl.$^{6}$ .............................. C12P 21/06; C12Q 1/00; C12N 15/00

[52] U.S. Cl. ....................... 435/69.1; 435/320.1; 435/7.2; 435/7.6; 435/69.7

[58] Field of Search ............................ 435/7.2, 7.6, 69.1, 435/320.1, 69.7, 69, 183; 530/399, 412, 413, 300, 344

[56] References Cited

U.S. PATENT DOCUMENTS

| | | | |
|---|---|---|---|
| 5,047,333 | 9/1991 | Grandi et al. | 435/68.1 |
| 5,223,409 | 6/1993 | Ladner et al. | 435/41 |

FOREIGN PATENT DOCUMENTS

| | | | |
|---|---|---|---|
| WO 90/02809 | 3/1990 | WIPO | C12P 21/00 |
| WO 90/04788 | 5/1990 | WIPO . | |

OTHER PUBLICATIONS

Armstrong et al., "Domain Structure of Bacteriophage fd Adsorption Protein" *FEBS Letters* 135(1):167–172 (1981).

Bass et al., "Hormone phage: an enrichment method for variant proteins with altered binding properties" *Protein: Structure, Function, and Genetics* 8(4):309–314 (1990).

Bowie et al., "Deciphering the Message in Protein Sequences: Tolerance to Amino Acid Substitutions" *Science* 247:1306–1310 (1990).

Crissman et al., "Gene–III protein of filamentous phages: evidence for a carboxyl–terminal domain with a role in morphogenesis" *Virology* 132(2):445–455 (1984).

Cunningham et al., "Engineering human prolactin to bind to the human growth hormone receptor" *Science* 247:1461–1465 (1990).

Cwirla et al., "Peptides on phage: a vast library of peptides for identifying ligands" *Proc. Natl. Acad. Sci. USA* 87(16):6378–6382 (1990).

De la Cruz et al., "Immunogenicity and epitope mapping of foreign sequences via genetically engineered filamentous phage" *Journal of Biological Chemistry* 263(9):4318–4322 (1988).

Devlin et al., "Random peptide libraries: a source of specific protein binding molecules" *Science* 249(4967):404–406 (1990).

Fuh et al., "The human growth hormone receptor. Secretion from *Escherichia coli* and disulfide bonding pattern of the extracellular binding domain" *Journal of Biological Chemistry* 265(6):3111–3115 (1990).

Geysen, "Antigen—antibody interactions at the molecular level: adventures in peptide synthesis" *Immunology Today* 6:364–369 (1985).

Geysen et al., "A priori delineation of a peptide which mimics a discontinuous antigenic determinant" *Molecular Immunology* 23(7):709–715 (1986).

Gussow et al. *Cold Spring Harbor Symposia on Quantitative Biology* 54:265–272 (1989).

McCafferty et al., "Phage antibodies: filamentous phage displaying antibody variable domains" *Nature* 348:552–554 (1990).

McFarland et al., "Lutropin–Choriogonadotropin Receptor: An Unusual Member of the G Protein–Coupled Receptor Family" *Science* 245:494–499 (1989).

Orlandi et al., "Cloning Immunoglobulin Variable Domains for Expression by the Polymerase Chain Reaction" *Proc. Natl. Acad. Sci. USA* 86:3833–3837 (1989).
Parmley et al., "Antibody–selectable filamentous fd phage vectors: affinity purification of target genes" *Gene* 73:305–318 (1988).
Rasched et al., "Ff coliphages: structural and functional relationships" *Microbiol. Rev*. 50(4):401–427 (1986).
Rutter et al., "Redesigning Proteins via Genetic Engineering" *Protein Engineering*, Oxender & Fox, Chapter 23, pp. 257–267 (1987).
Scott et al., "Searching for peptide ligands with an epitope library" *Science* 249(4967):386–390 (1990).
Shortle,, "Genetic Strategies for Analyzing Proteins" *Protein Engineering*, Oxender & Fox (eds.), New York:A.R. Liss, Inc. pp. 103–108 (1985).
Smith, "Filamentous fusion phage: novel expression vectors that display cloned antigens on the virion surface" *Science* 228(4705):1315–1317 (1985).
Wells et al., "Cassette mutagenesis: an efficient method for generation of multiple mutations at defined sites" *Gene* 34(2–3):315–323 (1985).
Matthews et al 1994 Protein Science 3:1197–1205.
Matthews et al 1993 Science 260:1113–1117.
Wells et al 1993 Protein Eng 6(Suppl):105.
Lowman et al 1991 Biochemistry 30:10832–10838.

*Primary Examiner*—Karen Cochrane Carlson
*Attorney, Agent, or Firm*—Daryl B. Winter; Timothy R. Schwartz

[57] ABSTRACT

A method for identifying and selecting novel substrates for enzymes is provided. The method comprises constructing a gene fusion comprising DNA encoding a polypeptide fused to DNA encoding a substrate peptide, which in turn is fused to DNA encoding at least a portion of a phage coat protein. The DNA encoding the substrate peptide is mutated at one or more codons thereby generating a family of mutants. The fusion protein is expressed on the surface of a phagemid particle and subjected to chemical or enzymatic modification of the substrate peptide. Those phagemid particles which have been modified are then separated from those that have not.

16 Claims, 23 Drawing Sheets

Starting Library:
NNS codons at hGH residues
172, 174, 176, 178

↓ 3.9 x 10⁷ transformants

Glycine elution

↓

Glycine elution

↓

KELR  +        += L163P
KDIN
REGK
RNGP
CNGK
SKLS
QRPG  ++      ++= K168R
LLLV

1 NF

| THEORETICAL | | EXPERIMENTAL |
|---|---|---|
| $1.05 \times 10^6$ | DNA seq.'s | $8.2 \times 10^6$ |
| $1.6 \times 10^5$ | A.A. seq.'s | ?? |

```
ATG AAA AAG AAT ATC GCA TTT CTT CTT GCA TCT ATG 36
Met Lys Lys Asn Ile Ala Phe Leu Leu Ala Ser Met
     1               5                  10

TTC GTT TTT TCT ATT GCT ACA AAC GCG TAC GCT GAT ATC 75
Phe Val Phe Ser Ile Ala Thr Asn Ala Tyr Ala Asp Ile
         15                  20                  25

CAG ATG ACC CAG TCC CCG AGC TCC CTG TCC GCC TCT GTG 114
Gln Met Thr Gln Ser Pro Ser Ser Leu Ser Ala Ser Val
                 30                  35

GGC GAT AGG GTC ACC ATC ACC TGC CGT GCC AGT CAG GAT 153
Gly Asp Arg Val Thr Ile Thr Cys Arg Ala Ser Gln Asp
     40                  45                  50

GTG AAT ACT GCT GTA GCC TGG TAT CAA CAG AAA CCA GGA 192
Val Asn Thr Ala Val Ala Trp Tyr Gln Gln Lys Pro Gly
             55                  60

AAA GCT CCG AAA CTA CTG ATT TAC TCG GCA TCC TTC CTC 231
Lys Ala Pro Lys Leu Leu Ile Tyr Ser Ala Ser Phe Leu
 65                  70                  75

TAC TCT GGA GTC CCT TCT CGC TTC TCT GGA TCC AGA TCT 270
Tyr Ser Gly Val Pro Ser Arg Phe Ser Gly Ser Arg Ser
         80                  85                  90
```

FIG. 11A

```
GGG ACG GAT TTC ACT CTG ACC ATC AGC AGT CTG CAG CCG 309
Gly Thr Asp Phe Thr Leu Thr Ile Ser Ser Leu Gln Pro
                 95                 100

GAA GAC TTC GCA ACT TAT TAC TGT CAG CAA CAT TAT ACT 348
Glu Asp Phe Ala Thr Tyr Tyr Cys Gln Gln His Tyr Thr
    105                 110                 115

ACT CCT CCC ACG TTC GGA CAG GGT ACC AAG GTG GAG ATC 387
Thr Pro Pro Thr Phe Gly Gln Gly Thr Lys Val Glu Ile
            120                 125

AAA CGA ACT GTG GCT GCA CCA TCT GTC TTC ATC TTC CCG 426
Lys Arg Thr Val Ala Ala Pro Ser Val Phe Ile Phe Pro
130                 135                 140

CCA TCT GAT GAG CAG TTG AAA TCT GGA ACT GCC TCT GTT 465
Pro Ser Asp Glu Gln Leu Lys Ser Gly Thr Ala Ser Val
        145                 150                 155

GTG TGC CTG CTG AAT AAC TTC TAT CCC AGA GAG GCC AAA 504
Val Cys Leu Leu Asn Asn Phe Tyr Pro Arg Glu Ala Lys
                160                 165

GTA CAG TGG AAG GTG GAT AAC GCC CTC CAA TCG GGT AAC 543
Val Gln Trp Lys Val Asp Asn Ala Leu Gln Ser Gly Asn
    170                 175                 180
```

FIG. 11B

```
TCC CAG GAG AGT GTC ACA GAG CAG GAC AGC AAG GAC AGC 582
Ser Gln Glu Ser Val Thr Glu Gln Asp Ser Lys Asp Ser
            185                 190

ACC TAC AGC CTC AGC AGC ACC CTG ACG CTG AGC AAA GCA 621
Thr Tyr Ser Leu Ser Ser Thr Leu Thr Leu Ser Lys Ala
195                 200                 205

GAC TAC GAG AAA CAC AAA GTC TAC GCC TGC GAA GTC ACC 660
Asp Tyr Glu Lys His Lys Val Tyr Ala Cys Glu Val Thr
        210                 215                 220

CAT CAG GGC CTG AGC TCG CCC GTC ACA AAG AGC TTC AAC 699
His Gln Gly Leu Ser Ser Pro Val Thr Lys Ser Phe Asn
                225                 230

AGG GGA GAG TGT TAAGCTGAT CCTCTACGCC GGACGCATCG 740
Arg Gly Glu Cys
    235     237

TGGCCCTAGT ACGCAAGTTC ACGTAAAAAG GGTATCTAGA GGTTGAGGTG 790

ATTTT      ATG AAA AAG AAT ATC GCA TTT CTT CTT GCA TCT 828
           Met Lys Lys Asn Ile Ala Phe Leu Leu Ala Ser
           238     240                 245
```

FIG. 11C

```
ATG TTC GTT TTT TCT ATT GCT ACA AAC GCG TAC GCT GAG 867
Met Phe Val Phe Ser Ile Ala Thr Asn Ala Tyr Ala Glu
    250                 255                 260

GTT CAG CTG GTG GAG TCT GGC GGT GGC CTG GTG CAG CCA 906
Val Gln Leu Val Glu Ser Gly Gly Gly.Leu Val Gln Pro
            265                 270

GGG GGC TCA CTC CGT TTG TCC TGT GCA GCT TCT GGC TTC 945
Gly Gly Ser Leu Arg Leu Ser Cys Ala Ala Ser Gly Phe
275                 280                 285

AAC ATT AAA GAC ACC TAT ATA CAC TGG GTG CGT CAG GCC 984
Asn Ile Lys Asp Thr Tyr Ile His Trp Val Arg Gln Ala
        290                 295                 300

CCG GGT AAG GGC CTG GAA TGG GTT GCA AGG ATT TAT CCT 1023
Pro Gly Lys Gly Leu Glu Trp Val Ala Arg Ile Tyr Pro
                305                 310

ACG AAT GGT TAT ACT AGA TAT GCC GAT AGC GTC AAG GGC 1062
Thr Asn Gly Tyr Thr Arg Tyr Ala Asp Ser Val Lys Gly
    315                 320                 325

CGT TTC ACT ATA AGC GCA GAC ACA TCC AAA AAC ACA GCC 1101
Arg Phe Thr Ile Ser Ala Asp Thr Ser Lys Asn Thr Ala
            330                 335
```

FIG. 11D

TAC CTG CAG ATG AAC AGC CTG CGT GCT GAG GAC ACT GCC 1140
Tyr Leu Gln Met Asn Ser Leu Arg Ala Glu Asp Thr Ala
340 345 350

GTC TAT TAT TGT TCT AGA TGG GGA GGG GAC GGC TTC TAT 1179
Val Tyr Tyr Cys Ser Arg Trp Gly Gly Asp Gly Phe Tyr
355 360 365

GCT ATG GAC TAC TGG GGT CAA GGA ACC CTG GTC ACC GTC 1218
Ala Met Asp Tyr Trp Gly Gln Gly Thr Leu Val Thr Val
370 375

TCC TCG GCC TCC ACC AAG GGC CCA TCG GTC TTC CCC CTG 1257
Ser Ser Ala Ser Thr Lys Gly Pro Ser Val Phe Pro Leu
380 385 390

GCA CCC TCC TCC AAG AGC ACC TCT GGG GGC ACA GCG GCC 1296
Ala Pro Ser Ser Lys Ser Thr Ser Gly Gly Thr Ala Ala
395 400

CTG GGC TGC CTG GTC AAG GAC TAC TTC CCC GAA CCG GTG 1335
Leu Gly Cys Leu Val Lys Asp Tyr Phe Pro Glu Pro Val
405 410 415

ACG GTG TCG TGG AAC TCA GGC GCC CTG ACC AGC GGC GTG 1374
Thr Val Ser Trp Asn Ser Gly Ala Leu Thr Ser Gly Val
420 425 430

FIG. 11E

```
CAC ACC TTC CCG GCT GTC CTA CAG TCC TCA GGA CTC TAC 1413
His Thr Phe Pro Ala Val Leu Gln Ser Ser Gly Leu Tyr
                435                 440

TCC CTC AGC AGC GTG GTG ACT GTG CCC TCT AGC AGC TTG 1452
Ser Leu Ser Ser Val Val Thr Val Pro Ser Ser Ser Leu
    445                 450                 455

GGC ACC CAG ACC TAC ATC TGC AAC GTG AAT CAC AAG CCC 1491
Gly Thr Gln Thr Tyr Ile Cys Asn Val Asn His Lys Pro
            460                 465

AGC AAC ACC AAG GTG GAC AAG AAA GTT GAG CCC AAA TCT 1530
Ser Asn Thr Lys Val Asp Lys Lys Val Glu Pro Lys Ser
470                 475                 480

TGT GAC AAA ACT CAC ACA GGG CCC TTC GTT TGT GAA TAT 1569
Cys Asp Lys Thr His Thr Gly Pro Phe Val Cys Glu Tyr
        485                 490                 495

CAA GGC CAA TCG TCT GAC CTG CCT CAA CCT CCT GTC AAT 1608
Gln Gly Gln Ser Ser Asp Leu Pro Gln Pro Pro Val Asn
                500                 505

GCT GGC GGC GGC TCT GGT GGT GGT TCT GGT GGC GGC TCT 1647
Ala Gly Gly Gly Ser Gly Gly Gly Ser Gly Gly Gly Ser
    510                 515                 520
```

```
GAG GGT GGT GGC TCT GAG GGT GGC GGT TCT GAG GGT GGC 1686
Glu Gly Gly Gly Ser Glu Gly Gly Gly Ser Glu Gly Gly
            525                 530

GGC TCT GAG GGA GGC GGT TCC GGT GGT GGC TCT GGT TCC 1725
Gly Ser Glu Gly Gly Gly Ser Gly Gly Gly Ser Gly Ser
535                 540                 545

GGT GAT TTT GAT TAT GAA AAG ATG GCA AAC GCT AAT AAG 1764
Gly Asp Phe Asp Tyr Glu Lys Met Ala Asn Ala Asn Lys
        550                 555                 560

GGG GCT ATG ACC GAA AAT GCC GAT GAA AAC GCG CTA CAG 1803
Gly Ala Met Thr Glu Asn Ala Asp Glu Asn Ala Leu Gln
                565                 570

TCT GAC GCT AAA GGC AAA CTT GAT TCT GTC GCT ACT GAT 1842
Ser Asp Ala Lys Gly Lys Leu Asp Ser Val Ala Thr Asp
    575                 580                 585

TAC GGT GCT GCT ATC GAT GGT TTC ATT GGT GAC GTT TCC 1881
Tyr Gly Ala Ala Ile Asp Gly Phe Ile Gly Asp Val Ser
            590                 595

GGC CTT GCT AAT GGT AAT GGT GCT ACT GGT GAT TTT GCT 1920
Gly Leu Ala Asn Gly Asn Gly Ala Thr Gly Asp Phe Ala
600                 605                 610
```

```
GGC TCT AAT TCC CAA ATG GCT CAA GTC GGT GAC GGT GAT 1959
Gly Ser Asn Ser Gln Met Ala Gln Val Gly Asp Gly Asp
        615                 620                 625

AAT TCA CCT TTA ATG AAT AAT TTC CGT CAA TAT TTA CCT 1998
Asn Ser Pro Leu Met Asn Asn Phe Arg Gln Tyr Leu Pro
                630                 635

TCC CTC CCT CAA TCG GTT GAA TGT CGC CCT TTT GTC TTT 2037
Ser Leu Pro Gln Ser Val Glu Cys Arg Pro Phe Val Phe
    640                 645                 650

AGC GCT GGT AAA CCA TAT GAA TTT TCT ATT GAT TGT GAC 2076
Ser Ala Gly Lys Pro Tyr Glu Phe Ser Ile Asp Cys Asp
            655                 660

AAA ATA AAC TTA TTC CGT GGT GTC TTT GCG TTT CTT TTA 2115
Lys Ile Asn Leu Phe Arg Gly Val Phe Ala Phe Leu Leu
665                 670                 675

TAT GTT GCC ACC TTT ATG TAT GTA TTT TCT ACG TTT GCT 2154
Tyr Val Ala Thr Phe Met Tyr Val Phe Ser Thr Phe Ala
        680                 685                 690

AAC ATA CTG CGT AAT AAG GAG TCT 2178
Asn Ile Leu Arg Asn Lys Glu Ser
                695         698
```

FIG. 11H

SEQUENCE LISTING ( 1 ) GENERAL INFORMATION:

( i i i ) NUMBER OF SEQUENCES: 152

( 2 ) INFORMATION FOR SEQ ID NO:1:

( i ) SEQUENCE CHARACTERISTICS:
( A ) LENGTH: 4 amino acids
( B ) TYPE: amino acid
( D ) TOPOLOGY: linear ( x i ) SEQUENCE DESCRIPTION: SEQ ID NO:1:

Lys Ser Tyr Arg
1 4

( 2 ) INFORMATION FOR SEQ ID NO:2:

( i ) SEQUENCE CHARACTERISTICS:
( A ) LENGTH: 4 amino acids
( B ) TYPE: amino acid
( D ) TOPOLOGY: linear ( x i ) SEQUENCE DESCRIPTION: SEQ ID NO:2:

Lys Glu Phe Arg
1 4

( 2 ) INFORMATION FOR SEQ ID NO:3:

( i ) SEQUENCE CHARACTERISTICS:
( A ) LENGTH: 4 amino acids
( B ) TYPE: amino acid
( D ) TOPOLOGY: linear ( x i ) SEQUENCE DESCRIPTION: SEQ ID NO:3:

Ala Asn His Gln
1 4

( 2 ) INFORMATION FOR SEQ ID NO:4:

( i ) SEQUENCE CHARACTERISTICS:
( A ) LENGTH: 4 amino acids
( B ) TYPE: amino acid
( D ) TOPOLOGY: linear ( x i ) SEQUENCE DESCRIPTION: SEQ ID NO:4:

Thr Leu Asp Thr
1 4

( 2 ) INFORMATION FOR SEQ ID NO:5:

( i ) SEQUENCE CHARACTERISTICS:
( A ) LENGTH: 36 bases
( B ) TYPE: nucleic acid
( C ) STRANDEDNESS: single
( D ) TOPOLOGY: linear ( x i ) SEQUENCE DESCRIPTION: SEQ ID NO:5:

GGCAGCTGTG GCTTCTAGAG TGGCGGCGGC TCTGGT 36

( 2 ) INFORMATION FOR SEQ ID NO:6:

-continued ( i ) SEQUENCE CHARACTERISTICS:
( A ) LENGTH: 36 bases
( B ) TYPE: nucleic acid
( C ) STRANDEDNESS: single
( D ) TOPOLOGY: linear ( x i ) SEQUENCE DESCRIPTION: SEQ ID NO:6:

A G C T G T G G C T   T C G G G C C C T T   A G C A T T T A A T   G C G G T A   3 6

( 2 ) INFORMATION FOR SEQ ID NO:7:

( i ) SEQUENCE CHARACTERISTICS:
( A ) LENGTH: 33 bases
( B ) TYPE: nucleic acid
( C ) STRANDEDNESS: single
( D ) TOPOLOGY: linear ( x i ) SEQUENCE DESCRIPTION: SEQ ID NO:7:

T T C A C A A A C G   A A G G G C C C C T   A A T T A A A G C C   A G A   3 3

( 2 ) INFORMATION FOR SEQ ID NO:8:

( i ) SEQUENCE CHARACTERISTICS:
( A ) LENGTH: 30 bases
( B ) TYPE: nucleic acid
( C ) STRANDEDNESS: single
( D ) TOPOLOGY: linear ( x i ) SEQUENCE DESCRIPTION: SEQ ID NO:8:

C A A T A A T A A C   G G G C T A G C C A   A A A G A A C T G G   3 0

( 2 ) INFORMATION FOR SEQ ID NO:9:

( i ) SEQUENCE CHARACTERISTICS:
( A ) LENGTH: 24 bases
( B ) TYPE: nucleic acid
( C ) STRANDEDNESS: single
( D ) TOPOLOGY: linear ( x i ) SEQUENCE DESCRIPTION: SEQ ID NO:9:

C A C G A C A G A A   T T C C C G A C T G   G A A A   2 4

( 2 ) INFORMATION FOR SEQ ID NO:10:

( i ) SEQUENCE CHARACTERISTICS:
( A ) LENGTH: 23 bases
( B ) TYPE: nucleic acid
( C ) STRANDEDNESS: single
( D ) TOPOLOGY: linear ( x i ) SEQUENCE DESCRIPTION: SEQ ID NO:10:

C T G T T T C T A G   A G T G A A A T T G   T T A   2 3

( 2 ) INFORMATION FOR SEQ ID NO:11:

( i ) SEQUENCE CHARACTERISTICS:
( A ) LENGTH: 23 bases
( B ) TYPE: nucleic acid
( C ) STRANDEDNESS: single
( D ) TOPOLOGY: linear ( x i ) SEQUENCE DESCRIPTION: SEQ ID NO:11:

G A C A T T C C T G   G G T A C C G T G C   A G T   2 3

( 2 ) INFORMATION FOR SEQ ID NO:12:

( i ) SEQUENCE CHARACTERISTICS:
( A ) LENGTH: 63 bases ( B ) TYPE: nucleic acid
( C ) STRANDEDNESS: single
( D ) TOPOLOGY: linear ( x i ) SEQUENCE DESCRIPTION: SEQ ID NO:12:

GCTTCAGGAA GGACATGGAC NNSGTCNNSA CANNSCTGNN SATCGTGCAG 50

TGCCGCTCTG TGG 63

( 2 ) INFORMATION FOR SEQ ID NO:13:

( i ) SEQUENCE CHARACTERISTICS:
( A ) LENGTH: 24 bases
( B ) TYPE: nucleic acid
( C ) STRANDEDNESS: single
( D ) TOPOLOGY: linear ( x i ) SEQUENCE DESCRIPTION: SEQ ID NO:13:

AAGGTCTCCA CATACCTGAG GATC 24

( 2 ) INFORMATION FOR SEQ ID NO:14:

( i ) SEQUENCE CHARACTERISTICS:
( A ) LENGTH: 33 bases
( B ) TYPE: nucleic acid
( C ) STRANDEDNESS: single
( D ) TOPOLOGY: linear ( x i ) SEQUENCE DESCRIPTION: SEQ ID NO:14:

ATGGACAAGG TGTCGACATA CCTGCGCATC GTG 33

( 2 ) INFORMATION FOR SEQ ID NO:15:

( i ) SEQUENCE CHARACTERISTICS:
( A ) LENGTH: 36 bases
( B ) TYPE: nucleic acid
( C ) STRANDEDNESS: single
( D ) TOPOLOGY: linear ( x i ) SEQUENCE DESCRIPTION: SEQ ID NO:15:

GGCAGCTGTG GCTTCTAGAG TGGCGGCGGC TCTGGT 36

( 2 ) INFORMATION FOR SEQ ID NO:16:

( i ) SEQUENCE CHARACTERISTICS:
( A ) LENGTH: 12 amino acids
( B ) TYPE: amino acid
( D ) TOPOLOGY: linear ( x i ) SEQUENCE DESCRIPTION: SEQ ID NO:16:

Gly Ser Cys Gly Phe Glu Ser Gly Gly Gly Ser Gly
1 5 10 12

( 2 ) INFORMATION FOR SEQ ID NO:17:

( i ) SEQUENCE CHARACTERISTICS:
( A ) LENGTH: 36 bases
( B ) TYPE: nucleic acid
( C ) STRANDEDNESS: single
( D ) TOPOLOGY: linear ( x i ) SEQUENCE DESCRIPTION: SEQ ID NO:17:

GGCAGCTGTG GATTCTAGAG TGGCGGTGGC TCTGGT 36

( 2 ) INFORMATION FOR SEQ ID NO:18:

( i ) SEQUENCE CHARACTERISTICS:
( A ) LENGTH: 27 bases (B) TYPE: nucleic acid
(C) STRANDEDNESS: single
(D) TOPOLOGY: linear (xi) SEQUENCE DESCRIPTION: SEQ ID NO:18:

CGGACTGGGC AGATATTCAA GCAGACC 27

(2) INFORMATION FOR SEQ ID NO:19:

(i) SEQUENCE CHARACTERISTICS:
(A) LENGTH: 38 bases
(B) TYPE: nucleic acid
(C) STRANDEDNESS: single
(D) TOPOLOGY: linear (xi) SEQUENCE DESCRIPTION: SEQ ID NO:19:

CTCAAGAACT ACGGGTTACC CTGACTGCTT CAGGAAGG 38

(2) INFORMATION FOR SEQ ID NO:20:

(i) SEQUENCE CHARACTERISTICS:
(A) LENGTH: 30 bases
(B) TYPE: nucleic acid
(C) STRANDEDNESS: single
(D) TOPOLOGY: linear (xi) SEQUENCE DESCRIPTION: SEQ ID NO:20:

CGCATCGTGC AGTGCAGATC TGTGGAGGGC 30

(2) INFORMATION FOR SEQ ID NO:21:

(i) SEQUENCE CHARACTERISTICS:
(A) LENGTH: 66 bases
(B) TYPE: nucleic acid
(C) STRANDEDNESS: single
(D) TOPOLOGY: linear (xi) SEQUENCE DESCRIPTION: SEQ ID NO:21:

GTTACTCTAC TGCTTTCAGG AAGGACATGG ACNNSGTCNN SACANNSCTG 50

NNSATCGTGC AGTGCA 66

(2) INFORMATION FOR SEQ ID NO:22:

(i) SEQUENCE CHARACTERISTICS:
(A) LENGTH: 64 bases
(B) TYPE: nucleic acid
(C) STRANDEDNESS: single
(D) TOPOLOGY: linear (xi) SEQUENCE DESCRIPTION: SEQ ID NO:22:

GATCTGCACT GCACGATSNN CAGSNNTGTS NNGACSNNGT CCATGTCCTT 50

CCTGAAGCAG TAGA 64

(2) INFORMATION FOR SEQ ID NO:23:

(i) SEQUENCE CHARACTERISTICS:
(A) LENGTH: 7 bases
(B) TYPE: nucleic acid
(C) STRANDEDNESS: single
(D) TOPOLOGY: linear (xi) SEQUENCE DESCRIPTION: SEQ ID NO:23:

GGTNACC 7

(2) INFORMATION FOR SEQ ID NO:24:

( i ) SEQUENCE CHARACTERISTICS:
( A ) LENGTH: 4 amino acids
( B ) TYPE: amino acid
( D ) TOPOLOGY: linear ( x i ) SEQUENCE DESCRIPTION: SEQ ID NO:24:

Lys Xaa Asn Thr
1 4

( 2 ) INFORMATION FOR SEQ ID NO:25:

( i ) SEQUENCE CHARACTERISTICS:
( A ) LENGTH: 4 amino acids
( B ) TYPE: amino acid
( D ) TOPOLOGY: linear ( x i ) SEQUENCE DESCRIPTION: SEQ ID NO:25:

Thr Trp Gly Ser
1 4

( 2 ) INFORMATION FOR SEQ ID NO:26:

( i ) SEQUENCE CHARACTERISTICS:
( A ) LENGTH: 4 amino acids
( B ) TYPE: amino acid
( D ) TOPOLOGY: linear ( x i ) SEQUENCE DESCRIPTION: SEQ ID NO:26:

Pro Xaa Glu Arg
1 4

( 2 ) INFORMATION FOR SEQ ID NO:27:

( i ) SEQUENCE CHARACTERISTICS:
( A ) LENGTH: 4 amino acids
( B ) TYPE: amino acid
( D ) TOPOLOGY: linear ( x i ) SEQUENCE DESCRIPTION: SEQ ID NO:27:

Leu Pro Pro Ser
1 4

( 2 ) INFORMATION FOR SEQ ID NO:28:

( i ) SEQUENCE CHARACTERISTICS:
( A ) LENGTH: 4 amino acids
( B ) TYPE: amino acid
( D ) TOPOLOGY: linear ( x i ) SEQUENCE DESCRIPTION: SEQ ID NO:28:

Ser Leu Asp Pro
1 4

( 2 ) INFORMATION FOR SEQ ID NO:29:

( i ) SEQUENCE CHARACTERISTICS:
( A ) LENGTH: 4 amino acids
( B ) TYPE: amino acid
( D ) TOPOLOGY: linear ( x i ) SEQUENCE DESCRIPTION: SEQ ID NO:29:

Gln Gln Ser Asn
1 4

( 2 ) INFORMATION FOR SEQ ID NO:30:

( i ) SEQUENCE CHARACTERISTICS:
( A ) LENGTH: 4 amino acids ( B ) TYPE: amino acid
( D ) TOPOLOGY: linear ( x i ) SEQUENCE DESCRIPTION: SEQ ID NO:30:

Gly Ser Lys Thr
1 4

( 2 ) INFORMATION FOR SEQ ID NO:31:

( i ) SEQUENCE CHARACTERISTICS:
( A ) LENGTH: 4 amino acids
( B ) TYPE: amino acid
( D ) TOPOLOGY: linear ( x i ) SEQUENCE DESCRIPTION: SEQ ID NO:31:

Thr Pro Val Thr
1 4

( 2 ) INFORMATION FOR SEQ ID NO:32:

( i ) SEQUENCE CHARACTERISTICS:
( A ) LENGTH: 4 amino acids
( B ) TYPE: amino acid
( D ) TOPOLOGY: linear ( x i ) SEQUENCE DESCRIPTION: SEQ ID NO:32:

Arg Ser Arg Ala
1 4

( 2 ) INFORMATION FOR SEQ ID NO:33:

( i ) SEQUENCE CHARACTERISTICS:
( A ) LENGTH: 4 amino acids
( B ) TYPE: amino acid
( D ) TOPOLOGY: linear ( x i ) SEQUENCE DESCRIPTION: SEQ ID NO:33:

Leu Cys Gly Leu
1 4

( 2 ) INFORMATION FOR SEQ ID NO:34:

( i ) SEQUENCE CHARACTERISTICS:
( A ) LENGTH: 4 amino acids
( B ) TYPE: amino acid
( D ) TOPOLOGY: linear ( x i ) SEQUENCE DESCRIPTION: SEQ ID NO:34:

Thr Gly Arg Leu
1 4

( 2 ) INFORMATION FOR SEQ ID NO:35:

( i ) SEQUENCE CHARACTERISTICS:
( A ) LENGTH: 4 amino acids
( B ) TYPE: amino acid
( D ) TOPOLOGY: linear ( x i ) SEQUENCE DESCRIPTION: SEQ ID NO:35:

Ala Lys Ala Ser
1 4

( 2 ) INFORMATION FOR SEQ ID NO:36:

( i ) SEQUENCE CHARACTERISTICS:
( A ) LENGTH: 4 amino acids
( B ) TYPE: amino acid
( D ) TOPOLOGY: linear ( x i ) SEQUENCE DESCRIPTION: SEQ ID NO:36:

Gly Asn Asp Asp
1 4

( 2 ) INFORMATION FOR SEQ ID NO:37:

( i ) SEQUENCE CHARACTERISTICS:
( A ) LENGTH: 4 amino acids
( B ) TYPE: amino acid
( D ) TOPOLOGY: linear ( x i ) SEQUENCE DESCRIPTION: SEQ ID NO:37:

Lys Thr Glu Gln
1 4

( 2 ) INFORMATION FOR SEQ ID NO:38:

( i ) SEQUENCE CHARACTERISTICS:
( A ) LENGTH: 4 amino acids
( B ) TYPE: amino acid
( D ) TOPOLOGY: linear ( x i ) SEQUENCE DESCRIPTION: SEQ ID NO:38:

Asn Asn Cys Arg
1 4

( 2 ) INFORMATION FOR SEQ ID NO:39:

( i ) SEQUENCE CHARACTERISTICS:
( A ) LENGTH: 4 amino acids
( B ) TYPE: amino acid
( D ) TOPOLOGY: linear ( x i ) SEQUENCE DESCRIPTION: SEQ ID NO:39:

Phe Pro Cys Leu
1 4

( 2 ) INFORMATION FOR SEQ ID NO:40:

( i ) SEQUENCE CHARACTERISTICS:
( A ) LENGTH: 4 amino acids
( B ) TYPE: amino acid
( D ) TOPOLOGY: linear ( x i ) SEQUENCE DESCRIPTION: SEQ ID NO:40:

Asn Ser Asp Phe
1 4

( 2 ) INFORMATION FOR SEQ ID NO:41:

( i ) SEQUENCE CHARACTERISTICS:
( A ) LENGTH: 4 amino acids
( B ) TYPE: amino acid
( D ) TOPOLOGY: linear ( x i ) SEQUENCE DESCRIPTION: SEQ ID NO:41:

His Arg Pro Ser
1 4

( 2 ) INFORMATION FOR SEQ ID NO:42:

( i ) SEQUENCE CHARACTERISTICS:
( A ) LENGTH: 4 amino acids
( B ) TYPE: amino acid
( D ) TOPOLOGY: linear ( x i ) SEQUENCE DESCRIPTION: SEQ ID NO:42:

Leu Ser Leu Xaa
1 4

( 2 ) INFORMATION FOR SEQ ID NO:43:

( i ) SEQUENCE CHARACTERISTICS:
( A ) LENGTH: 4 amino acids
( B ) TYPE: amino acid
( D ) TOPOLOGY: linear ( x i ) SEQUENCE DESCRIPTION: SEQ ID NO:43:

Asn Gly Ser Lys
1 4

( 2 ) INFORMATION FOR SEQ ID NO:44:

( i ) SEQUENCE CHARACTERISTICS:
( A ) LENGTH: 4 amino acids
( B ) TYPE: amino acid
( D ) TOPOLOGY: linear ( x i ) SEQUENCE DESCRIPTION: SEQ ID NO:44:

Leu Thr Thr Glu
1 4

( 2 ) INFORMATION FOR SEQ ID NO:45:

( i ) SEQUENCE CHARACTERISTICS:
( A ) LENGTH: 4 amino acids
( B ) TYPE: amino acid
( D ) TOPOLOGY: linear ( x i ) SEQUENCE DESCRIPTION: SEQ ID NO:45:

Pro Ser Gly Gly
1 4

( 2 ) INFORMATION FOR SEQ ID NO:46:

( i ) SEQUENCE CHARACTERISTICS:
( A ) LENGTH: 4 amino acids
( B ) TYPE: amino acid
( D ) TOPOLOGY: linear ( x i ) SEQUENCE DESCRIPTION: SEQ ID NO:46:

Leu Trp Phe Pro
1 4

( 2 ) INFORMATION FOR SEQ ID NO:47:

( i ) SEQUENCE CHARACTERISTICS:
( A ) LENGTH: 4 amino acids
( B ) TYPE: amino acid
( D ) TOPOLOGY: linear ( x i ) SEQUENCE DESCRIPTION: SEQ ID NO:47:

Pro Ala Gly Ser
1 4

( 2 ) INFORMATION FOR SEQ ID NO:48:

( i ) SEQUENCE CHARACTERISTICS:
( A ) LENGTH: 4 amino acids
( B ) TYPE: amino acid
( D ) TOPOLOGY: linear ( x i ) SEQUENCE DESCRIPTION: SEQ ID NO:48:

Gly Arg Ala Lys

-continued 1 4

( 2 ) INFORMATION FOR SEQ ID NO:49:

( i ) SEQUENCE CHARACTERISTICS:
( A ) LENGTH: 4 amino acids
( B ) TYPE: amino acid
( D ) TOPOLOGY: linear ( x i ) SEQUENCE DESCRIPTION: SEQ ID NO:49:

Gly Thr Asn Gly
1 4

( 2 ) INFORMATION FOR SEQ ID NO:50:

( i ) SEQUENCE CHARACTERISTICS:
( A ) LENGTH: 4 amino acids
( B ) TYPE: amino acid
( D ) TOPOLOGY: linear ( x i ) SEQUENCE DESCRIPTION: SEQ ID NO:50:

Cys Val Leu Gln
1 4

( 2 ) INFORMATION FOR SEQ ID NO:51:

( i ) SEQUENCE CHARACTERISTICS:
( A ) LENGTH: 4 amino acids
( B ) TYPE: amino acid
( D ) TOPOLOGY: linear ( x i ) SEQUENCE DESCRIPTION: SEQ ID NO:51:

Glu Ala Ser Leu
1 4

( 2 ) INFORMATION FOR SEQ ID NO:52:

( i ) SEQUENCE CHARACTERISTICS:
( A ) LENGTH: 4 amino acids
( B ) TYPE: amino acid
( D ) TOPOLOGY: linear ( x i ) SEQUENCE DESCRIPTION: SEQ ID NO:52:

Ser Ser Lys Glu
1 4

( 2 ) INFORMATION FOR SEQ ID NO:53:

( i ) SEQUENCE CHARACTERISTICS:
( A ) LENGTH: 4 amino acids
( B ) TYPE: amino acid
( D ) TOPOLOGY: linear ( x i ) SEQUENCE DESCRIPTION: SEQ ID NO:53:

Ala Leu Leu Leu
1 4

( 2 ) INFORMATION FOR SEQ ID NO:54:

( i ) SEQUENCE CHARACTERISTICS:
( A ) LENGTH: 4 amino acids
( B ) TYPE: amino acid
( D ) TOPOLOGY: linear ( x i ) SEQUENCE DESCRIPTION: SEQ ID NO:54:

Pro Ser His Pro
1 4

-continued ( 2 ) INFORMATION FOR SEQ ID NO:55:

( i ) SEQUENCE CHARACTERISTICS:
( A ) LENGTH: 4 amino acids
( B ) TYPE: amino acid
( D ) TOPOLOGY: linear ( x i ) SEQUENCE DESCRIPTION: SEQ ID NO:55:

Ser Tyr Ala Pro
1 4

( 2 ) INFORMATION FOR SEQ ID NO:56:

( i ) SEQUENCE CHARACTERISTICS:
( A ) LENGTH: 4 amino acids
( B ) TYPE: amino acid
( D ) TOPOLOGY: linear ( x i ) SEQUENCE DESCRIPTION: SEQ ID NO:56:

Ala Ser Asn Gly
1 4

( 2 ) INFORMATION FOR SEQ ID NO:57:

( i ) SEQUENCE CHARACTERISTICS:
( A ) LENGTH: 4 amino acids
( B ) TYPE: amino acid
( D ) TOPOLOGY: linear ( x i ) SEQUENCE DESCRIPTION: SEQ ID NO:57:

Glu Ala Asn Asn
1 4

( 2 ) INFORMATION FOR SEQ ID NO:58:

( i ) SEQUENCE CHARACTERISTICS:
( A ) LENGTH: 4 amino acids
( B ) TYPE: amino acid
( D ) TOPOLOGY: linear ( x i ) SEQUENCE DESCRIPTION: SEQ ID NO:58:

Lys Asn Ala Lys
1 4

( 2 ) INFORMATION FOR SEQ ID NO:59:

( i ) SEQUENCE CHARACTERISTICS:
( A ) LENGTH: 4 amino acids
( B ) TYPE: amino acid
( D ) TOPOLOGY: linear ( x i ) SEQUENCE DESCRIPTION: SEQ ID NO:59:

Ser Arg Gly Lys
1 4

( 2 ) INFORMATION FOR SEQ ID NO:60:

( i ) SEQUENCE CHARACTERISTICS:
( A ) LENGTH: 4 amino acids
( B ) TYPE: amino acid
( D ) TOPOLOGY: linear ( x i ) SEQUENCE DESCRIPTION: SEQ ID NO:60:

Gly Leu Asp Gly
1 4

( 2 ) INFORMATION FOR SEQ ID NO:61:

( i ) SEQUENCE CHARACTERISTICS:
( A ) LENGTH: 4 amino acids
( B ) TYPE: amino acid
( D ) TOPOLOGY: linear ( x i ) SEQUENCE DESCRIPTION: SEQ ID NO:61:

Asn Asp Pro Ile
1 4

( 2 ) INFORMATION FOR SEQ ID NO:62:

( i ) SEQUENCE CHARACTERISTICS:
( A ) LENGTH: 4 amino acids
( B ) TYPE: amino acid
( D ) TOPOLOGY: linear ( x i ) SEQUENCE DESCRIPTION: SEQ ID NO:62:

Arg Ser Phe Arg
1 4

( 2 ) INFORMATION FOR SEQ ID NO:63:

( i ) SEQUENCE CHARACTERISTICS:
( A ) LENGTH: 4 amino acids
( B ) TYPE: amino acid
( D ) TOPOLOGY: linear ( x i ) SEQUENCE DESCRIPTION: SEQ ID NO:63:

Arg Ala Tyr Arg
1 4

( 2 ) INFORMATION FOR SEQ ID NO:64:

( i ) SEQUENCE CHARACTERISTICS:
( A ) LENGTH: 4 amino acids
( B ) TYPE: amino acid
( D ) TOPOLOGY: linear ( x i ) SEQUENCE DESCRIPTION: SEQ ID NO:64:

Lys Thr Tyr Lys
1 4

( 2 ) INFORMATION FOR SEQ ID NO:65:

( i ) SEQUENCE CHARACTERISTICS:
( A ) LENGTH: 4 amino acids
( B ) TYPE: amino acid
( D ) TOPOLOGY: linear ( x i ) SEQUENCE DESCRIPTION: SEQ ID NO:65:

Arg Ser Tyr Arg
1 4

( 2 ) INFORMATION FOR SEQ ID NO:66:

( i ) SEQUENCE CHARACTERISTICS:
( A ) LENGTH: 4 amino acids
( B ) TYPE: amino acid
( D ) TOPOLOGY: linear ( x i ) SEQUENCE DESCRIPTION: SEQ ID NO:66:

Lys Ala Tyr Arg
1 4

( 2 ) INFORMATION FOR SEQ ID NO:67:

( i ) SEQUENCE CHARACTERISTICS:

( A ) LENGTH: 4 amino acids
( B ) TYPE: amino acid
( D ) TOPOLOGY: linear ( x i ) SEQUENCE DESCRIPTION: SEQ ID NO:67:

Arg Phe Phe Arg
1 4

( 2 ) INFORMATION FOR SEQ ID NO:68:

( i ) SEQUENCE CHARACTERISTICS:
( A ) LENGTH: 4 amino acids
( B ) TYPE: amino acid
( D ) TOPOLOGY: linear ( x i ) SEQUENCE DESCRIPTION: SEQ ID NO:68:

Lys Gln Tyr Arg
1 4

( 2 ) INFORMATION FOR SEQ ID NO:69:

( i ) SEQUENCE CHARACTERISTICS:
( A ) LENGTH: 4 amino acids
( B ) TYPE: amino acid
( D ) TOPOLOGY: linear ( x i ) SEQUENCE DESCRIPTION: SEQ ID NO:69:

Arg Thr Tyr His
1 4

( 2 ) INFORMATION FOR SEQ ID NO:70:

( i ) SEQUENCE CHARACTERISTICS:
( A ) LENGTH: 4 amino acids
( B ) TYPE: amino acid
( D ) TOPOLOGY: linear ( x i ) SEQUENCE DESCRIPTION: SEQ ID NO:70:

Gln Arg Tyr Arg
1 4

( 2 ) INFORMATION FOR SEQ ID NO:71:

( i ) SEQUENCE CHARACTERISTICS:
( A ) LENGTH: 4 amino acids
( B ) TYPE: amino acid
( D ) TOPOLOGY: linear ( x i ) SEQUENCE DESCRIPTION: SEQ ID NO:71:

Lys Lys Tyr Lys
1 4

( 2 ) INFORMATION FOR SEQ ID NO:72:

( i ) SEQUENCE CHARACTERISTICS:
( A ) LENGTH: 4 amino acids
( B ) TYPE: amino acid
( D ) TOPOLOGY: linear ( x i ) SEQUENCE DESCRIPTION: SEQ ID NO:72:

Arg Ser Phe Ser
1 4

( 2 ) INFORMATION FOR SEQ ID NO:73:

( i ) SEQUENCE CHARACTERISTICS:
( A ) LENGTH: 4 amino acids
( B ) TYPE: amino acid ( D ) TOPOLOGY: linear ( x i ) SEQUENCE DESCRIPTION: SEQ ID NO:73:

Lys Ser Asn Arg
1 4

( 2 ) INFORMATION FOR SEQ ID NO:74:

( i ) SEQUENCE CHARACTERISTICS:
( A ) LENGTH: 4 amino acids
( B ) TYPE: amino acid
( D ) TOPOLOGY: linear ( x i ) SEQUENCE DESCRIPTION: SEQ ID NO:74:

Lys Ala Phe Arg
1 4

( 2 ) INFORMATION FOR SEQ ID NO:75:

( i ) SEQUENCE CHARACTERISTICS:
( A ) LENGTH: 25 bases
( B ) TYPE: nucleic acid
( C ) STRANDEDNESS: single
( D ) TOPOLOGY: linear ( x i ) SEQUENCE DESCRIPTION: SEQ ID NO:75:

GCCTTTGACA GGTACCAGGA GTTTG 25

( 2 ) INFORMATION FOR SEQ ID NO:76:

( i ) SEQUENCE CHARACTERISTICS:
( A ) LENGTH: 34 bases
( B ) TYPE: nucleic acid
( C ) STRANDEDNESS: single
( D ) TOPOLOGY: linear ( x i ) SEQUENCE DESCRIPTION: SEQ ID NO:76:

CCAACTATAC CACTCTCGAG GTCTATTCGA TAAC 34

( 2 ) INFORMATION FOR SEQ ID NO:77:

( i ) SEQUENCE CHARACTERISTICS:
( A ) LENGTH: 66 bases
( B ) TYPE: nucleic acid
( C ) STRANDEDNESS: single
( D ) TOPOLOGY: linear ( x i ) SEQUENCE DESCRIPTION: SEQ ID NO:77:

TCGAGGCTCN NSGACAACGC GNNSCTGCGT GCTNNSCGTC TTNNSCAGCT 50

GGCCTTTGAC ACGTAC 66

( 2 ) INFORMATION FOR SEQ ID NO:78:

( i ) SEQUENCE CHARACTERISTICS:
( A ) LENGTH: 58 bases
( B ) TYPE: nucleic acid
( C ) STRANDEDNESS: single
( D ) TOPOLOGY: linear ( x i ) SEQUENCE DESCRIPTION: SEQ ID NO:78:

GTGTCAAAGG CCAGCTGSNN AAGACGSNNA GCACGCAGSN NCGCGTTGTC 50

SNNGAGCC 58

( 2 ) INFORMATION FOR SEQ ID NO:79:

( i ) SEQUENCE CHARACTERISTICS:

-continued ( A ) LENGTH: 65 bases
( B ) TYPE: nucleic acid
( C ) STRANDEDNESS: single
( D ) TOPOLOGY: linear ( x i ) SEQUENCE DESCRIPTION: SEQ ID NO:79:

GTTACTCTAC TGCTTCNNSA AGGACATGNN SAAGGTCAGC NNSTACCTGC 50

GCNNSGTGCA GTGCA 65

( 2 ) INFORMATION FOR SEQ ID NO:80:

( i ) SEQUENCE CHARACTERISTICS:
( A ) LENGTH: 64 bases
( B ) TYPE: nucleic acid
( C ) STRANDEDNESS: single
( D ) TOPOLOGY: linear ( x i ) SEQUENCE DESCRIPTION: SEQ ID NO:80:

GATCTGCACT GCACSNNGCG CAGGTASNNG CTGACCTTSN NCATGTCCTT 50

SNNGAAGCAG TAGA 64

( 2 ) INFORMATION FOR SEQ ID NO:81:

( i ) SEQUENCE CHARACTERISTICS:
( A ) LENGTH: 48 bases
( B ) TYPE: nucleic acid
( C ) STRANDEDNESS: single
( D ) TOPOLOGY: linear ( x i ) SEQUENCE DESCRIPTION: SEQ ID NO:81:

TTCGGGCCCT TCGCTGCTCA CTATACGCGT CAGTCGACTG ACCTGCCT 48

( 2 ) INFORMATION FOR SEQ ID NO:82:

( i ) SEQUENCE CHARACTERISTICS:
( A ) LENGTH: 42 amino acids
( B ) TYPE: amino acid
( D ) TOPOLOGY: linear ( x i ) SEQUENCE DESCRIPTION: SEQ ID NO:82:

Pro His Glu Gly Leu Tyr Pro Arg Xaa Pro His Glu Ala Leu Ala
1 5 10 15

Ala Leu Ala His Ile Ser Thr Tyr Arg Thr His Arg Ala Arg Gly
20 25 30

Gly Leu Asn Ser Glu Arg Thr His Arg Ala Ser Pro
35 40 42

( 2 ) INFORMATION FOR SEQ ID NO:83:

( i ) SEQUENCE CHARACTERISTICS:
( A ) LENGTH: 21 amino acids
( B ) TYPE: amino acid
( D ) TOPOLOGY: linear ( x i ) SEQUENCE DESCRIPTION: SEQ ID NO:83:

Ala Leu Ala Ala Leu Ala His Ile Ser Thr Tyr Arg Thr His Arg
1 5 10 15

Ala Arg Gly Gly Leu Asn
20 21

( 2 ) INFORMATION FOR SEQ ID NO:84:

( i ) SEQUENCE CHARACTERISTICS:
( A ) LENGTH: 45 bases
( B ) TYPE: nucleic acid (C) STRANDEDNESS: single
(D) TOPOLOGY: linear (xi) SEQUENCE DESCRIPTION: SEQ ID NO:84:

AGCTGTGGCT TCGGGCCCGC CGCCGCGTCG ACTGGCGGTG GCTCT 45

(2) INFORMATION FOR SEQ ID NO:85:

(i) SEQUENCE CHARACTERISTICS:
(A) LENGTH: 45 bases
(B) TYPE: nucleic acid
(C) STRANDEDNESS: single
(D) TOPOLOGY: linear (xi) SEQUENCE DESCRIPTION: SEQ ID NO:85:

AGCTGTGGCT TCGGGCCCGC CCCCGCGTCG ACTGGCGGTG GCTCT 45

(2) INFORMATION FOR SEQ ID NO:86:

(i) SEQUENCE CHARACTERISTICS:
(A) LENGTH: 25 bases
(B) TYPE: nucleic acid
(C) STRANDEDNESS: single
(D) TOPOLOGY: linear (xi) SEQUENCE DESCRIPTION: SEQ ID NO:86:

CTTCGCTGCT NNSNNSACCC GGCAA 25

(2) INFORMATION FOR SEQ ID NO:87:

(i) SEQUENCE CHARACTERISTICS:
(A) LENGTH: 33 bases
(B) TYPE: nucleic acid
(C) STRANDEDNESS: single
(D) TOPOLOGY: linear (xi) SEQUENCE DESCRIPTION: SEQ ID NO:87:

TCGATTGCCG GGTSNNSNNA GCAGCGAAGG GCC 33

(2) INFORMATION FOR SEQ ID NO:88:

(i) SEQUENCE CHARACTERISTICS:
(A) LENGTH: 7 amino acids
(B) TYPE: amino acid
(D) TOPOLOGY: linear (xi) SEQUENCE DESCRIPTION: SEQ ID NO:88:

Ala Ala His Tyr Thr Arg Gln
1 5 7

(2) INFORMATION FOR SEQ ID NO:89:

(i) SEQUENCE CHARACTERISTICS:
(A) LENGTH: 21 bases
(B) TYPE: nucleic acid
(C) STRANDEDNESS: single
(D) TOPOLOGY: linear (xi) SEQUENCE DESCRIPTION: SEQ ID NO:89:

GCTGCTCACT ACACCCGGCA A 21

(2) INFORMATION FOR SEQ ID NO:90:

(i) SEQUENCE CHARACTERISTICS:
(A) LENGTH: 7 amino acids
(B) TYPE: amino acid
(D) TOPOLOGY: linear ( x i ) SEQUENCE DESCRIPTION: SEQ ID NO:90:

Ala Ala His Met Thr Arg Gln
1 5 7

( 2 ) INFORMATION FOR SEQ ID NO:91:

( i ) SEQUENCE CHARACTERISTICS:
( A ) LENGTH: 21 bases
( B ) TYPE: nucleic acid
( C ) STRANDEDNESS: single
( D ) TOPOLOGY: linear ( x i ) SEQUENCE DESCRIPTION: SEQ ID NO:91:

GCTGCTCACA TGACCCGGCA A 21

( 2 ) INFORMATION FOR SEQ ID NO:92:

( i ) SEQUENCE CHARACTERISTICS:
( A ) LENGTH: 7 amino acids
( B ) TYPE: amino acid
( D ) TOPOLOGY: linear ( x i ) SEQUENCE DESCRIPTION: SEQ ID NO:92:

Ala Ala Leu His Thr Arg Gln
1 5 7

( 2 ) INFORMATION FOR SEQ ID NO:93:

( i ) SEQUENCE CHARACTERISTICS:
( A ) LENGTH: 21 bases
( B ) TYPE: nucleic acid
( C ) STRANDEDNESS: single
( D ) TOPOLOGY: linear ( x i ) SEQUENCE DESCRIPTION: SEQ ID NO:93:

GCTGCTCTCC ACACCCGGCA A 21

( 2 ) INFORMATION FOR SEQ ID NO:94:

( i ) SEQUENCE CHARACTERISTICS:
( A ) LENGTH: 21 bases
( B ) TYPE: nucleic acid
( C ) STRANDEDNESS: single
( D ) TOPOLOGY: linear ( x i ) SEQUENCE DESCRIPTION: SEQ ID NO:94:

GCTGCTCTGC ACACCCGGCA A 21

( 2 ) INFORMATION FOR SEQ ID NO:95:

( i ) SEQUENCE CHARACTERISTICS:
( A ) LENGTH: 6 amino acids
( B ) TYPE: amino acid
( D ) TOPOLOGY: linear ( x i ) SEQUENCE DESCRIPTION: SEQ ID NO:95:

Ala Ala His Thr Arg Gln
1 5 6

( 2 ) INFORMATION FOR SEQ ID NO:96:

( i ) SEQUENCE CHARACTERISTICS:
( A ) LENGTH: 18 bases
( B ) TYPE: nucleic acid
( C ) STRANDEDNESS: single
( D ) TOPOLOGY: linear ( x i ) SEQUENCE DESCRIPTION: SEQ ID NO:96:

GCTGCTCACA CCCGGCAA 18

(2) INFORMATION FOR SEQ ID NO:97:

(i) SEQUENCE CHARACTERISTICS:
(A) LENGTH: 7 amino acids
(B) TYPE: amino acid
(D) TOPOLOGY: linear (xi) SEQUENCE DESCRIPTION: SEQ ID NO:97:

Ala Ala Xaa His Thr Arg Gln
1 5 7

(2) INFORMATION FOR SEQ ID NO:98:

(i) SEQUENCE CHARACTERISTICS:
(A) LENGTH: 21 bases
(B) TYPE: nucleic acid
(C) STRANDEDNESS: single
(D) TOPOLOGY: linear (xi) SEQUENCE DESCRIPTION: SEQ ID NO:98:

GCTGCTNNNC ACACCCGGCA A 21

(2) INFORMATION FOR SEQ ID NO:99:

(i) SEQUENCE CHARACTERISTICS:
(A) LENGTH: 21 bases
(B) TYPE: nucleic acid
(C) STRANDEDNESS: single
(D) TOPOLOGY: linear (xi) SEQUENCE DESCRIPTION: SEQ ID NO:99:

GCTGCTCACT ATACGCGTCA G 21

(2) INFORMATION FOR SEQ ID NO:100:

(i) SEQUENCE CHARACTERISTICS:
(A) LENGTH: 7 amino acids
(B) TYPE: amino acid
(D) TOPOLOGY: linear (xi) SEQUENCE DESCRIPTION: SEQ ID NO:100:

Ala Ala Xaa His Thr Arg Gln
1 5 7

(2) INFORMATION FOR SEQ ID NO:101:

(i) SEQUENCE CHARACTERISTICS:
(A) LENGTH: 21 bases
(B) TYPE: nucleic acid
(C) STRANDEDNESS: single
(D) TOPOLOGY: linear (xi) SEQUENCE DESCRIPTION: SEQ ID NO:101:

GCTGCTCAGC ACACCCGGCA A 21

(2) INFORMATION FOR SEQ ID NO:102:

(i) SEQUENCE CHARACTERISTICS:
(A) LENGTH: 7 amino acids
(B) TYPE: amino acid
(D) TOPOLOGY: linear (xi) SEQUENCE DESCRIPTION: SEQ ID NO:102:

Ala Ala Thr His Thr Arg Gln
1 5 7

( 2 ) INFORMATION FOR SEQ ID NO:103:

( i ) SEQUENCE CHARACTERISTICS:
( A ) LENGTH: 21 bases
( B ) TYPE: nucleic acid
( C ) STRANDEDNESS: single
( D ) TOPOLOGY: linear ( x i ) SEQUENCE DESCRIPTION: SEQ ID NO:103:

GCTGCTACGC ACACCCGGCA A 21

( 2 ) INFORMATION FOR SEQ ID NO:104:

( i ) SEQUENCE CHARACTERISTICS:
( A ) LENGTH: 6 amino acids
( B ) TYPE: amino acid
( D ) TOPOLOGY: linear ( x i ) SEQUENCE DESCRIPTION: SEQ ID NO:104:

Ala Ala His Ser Arg Gln
1 5 6

( 2 ) INFORMATION FOR SEQ ID NO:105:

( i ) SEQUENCE CHARACTERISTICS:
( A ) LENGTH: 18 bases
( B ) TYPE: nucleic acid
( C ) STRANDEDNESS: single
( D ) TOPOLOGY: linear ( x i ) SEQUENCE DESCRIPTION: SEQ ID NO:105:

GCTGCTCACT CCCGGCAA 18

( 2 ) INFORMATION FOR SEQ ID NO:106:

( i ) SEQUENCE CHARACTERISTICS:
( A ) LENGTH: 7 amino acids
( B ) TYPE: amino acid
( D ) TOPOLOGY: linear ( x i ) SEQUENCE DESCRIPTION: SEQ ID NO:106:

Ala Ala His His Thr Arg Gln
1 5 7

( 2 ) INFORMATION FOR SEQ ID NO:107:

( i ) SEQUENCE CHARACTERISTICS:
( A ) LENGTH: 21 bases
( B ) TYPE: nucleic acid
( C ) STRANDEDNESS: single
( D ) TOPOLOGY: linear ( x i ) SEQUENCE DESCRIPTION: SEQ ID NO:107:

GCTGCTCATC ATACCCGGCA A 21

( 2 ) INFORMATION FOR SEQ ID NO:108:

( i ) SEQUENCE CHARACTERISTICS:
( A ) LENGTH: 6 amino acids
( B ) TYPE: amino acid
( D ) TOPOLOGY: linear ( x i ) SEQUENCE DESCRIPTION: SEQ ID NO:108:

Ala Ala His Phe Arg Gln
1 5 6

( 2 ) INFORMATION FOR SEQ ID NO:109:

( i ) SEQUENCE CHARACTERISTICS:
( A ) LENGTH: 18 bases
( B ) TYPE: nucleic acid
( C ) STRANDEDNESS: single
( D ) TOPOLOGY: linear ( x i ) SEQUENCE DESCRIPTION: SEQ ID NO:109:

GCTGCTCACT TCCGGCAA 1

( 2 ) INFORMATION FOR SEQ ID NO:110:

( i ) SEQUENCE CHARACTERISTICS:
( A ) LENGTH: 17 amino acids
( B ) TYPE: amino acid
( D ) TOPOLOGY: linear ( x i ) SEQUENCE DESCRIPTION: SEQ ID NO:110:

Gly Leu Tyr Gly Leu Tyr Xaa Xaa Xaa Xaa Xaa Gly Leu Tyr Gly
1 5 10 15

Leu Tyr
17

( 2 ) INFORMATION FOR SEQ ID NO:111:

( i ) SEQUENCE CHARACTERISTICS:
( A ) LENGTH: 33 bases
( B ) TYPE: nucleic acid
( C ) STRANDEDNESS: single
( D ) TOPOLOGY: linear ( x i ) SEQUENCE DESCRIPTION: SEQ ID NO:111:

CTAATGATAA TGAATTAATT GATAATGATA ATG 33

( 2 ) INFORMATION FOR SEQ ID NO:112:

( i ) SEQUENCE CHARACTERISTICS:
( A ) LENGTH: 41 bases
( B ) TYPE: nucleic acid
( C ) STRANDEDNESS: single
( D ) TOPOLOGY: linear ( x i ) SEQUENCE DESCRIPTION: SEQ ID NO:112:

TCGACATTAT CATTATCAAT TAATTCATTA TCATTAGGGC C 41

( 2 ) INFORMATION FOR SEQ ID NO:113:

( i ) SEQUENCE CHARACTERISTICS:
( A ) LENGTH: 34 bases
( B ) TYPE: nucleic acid
( C ) STRANDEDNESS: single
( D ) TOPOLOGY: linear ( x i ) SEQUENCE DESCRIPTION: SEQ ID NO:113:

CGGTGGTNNS NNSNNSNNSN NSGGTGGTCC TGGC 34

( 2 ) INFORMATION FOR SEQ ID NO:114:

( i ) SEQUENCE CHARACTERISTICS:
( A ) LENGTH: 42 bases
( B ) TYPE: nucleic acid
( C ) STRANDEDNESS: single
( D ) TOPOLOGY: linear ( x i ) SEQUENCE DESCRIPTION: SEQ ID NO:114:

TCGAGCCAGG ACCACCSNNS NNSNNSNNSN NACCACCGGG CC 42

( 2 ) INFORMATION FOR SEQ ID NO:115:

( i ) SEQUENCE CHARACTERISTICS:
( A ) LENGTH: 24 amino acids
( B ) TYPE: amino acid
( D ) TOPOLOGY: linear ( x i ) SEQUENCE DESCRIPTION: SEQ ID NO:115:

Gly Leu Tyr Gly Leu Tyr His Ile Ser Pro Arg Xaa Ser Glu Arg
1 5 10 15

Gly Leu Xaa Gly Leu Tyr Gly Leu Tyr
20 24

( 2 ) INFORMATION FOR SEQ ID NO:116:

( i ) SEQUENCE CHARACTERISTICS:
( A ) LENGTH: 17 amino acids
( B ) TYPE: amino acid
( D ) TOPOLOGY: linear ( x i ) SEQUENCE DESCRIPTION: SEQ ID NO:116:

Ala Leu Ala Ala Leu Ala Xaa Xaa Thr His Arg Ala Arg Gly Gly
1 5 10 15

Leu Asn
17

( 2 ) INFORMATION FOR SEQ ID NO:117:

( i ) SEQUENCE CHARACTERISTICS:
( A ) LENGTH: 5 amino acids
( B ) TYPE: amino acid
( D ) TOPOLOGY: linear ( x i ) SEQUENCE DESCRIPTION: SEQ ID NO:117:

Phe His Met Asn Val
1 5

( 2 ) INFORMATION FOR SEQ ID NO:118:

( i ) SEQUENCE CHARACTERISTICS:
( A ) LENGTH: 5 amino acids
( B ) TYPE: amino acid
( D ) TOPOLOGY: linear ( x i ) SEQUENCE DESCRIPTION: SEQ ID NO:118:

Asn His Tyr Thr Leu
1 5

( 2 ) INFORMATION FOR SEQ ID NO:119:

( i ) SEQUENCE CHARACTERISTICS:
( A ) LENGTH: 5 amino acids
( B ) TYPE: amino acid
( D ) TOPOLOGY: linear ( x i ) SEQUENCE DESCRIPTION: SEQ ID NO:119:

Thr His Tyr Phe Leu
1 5

( 2 ) INFORMATION FOR SEQ ID NO:120:

( i ) SEQUENCE CHARACTERISTICS:
( A ) LENGTH: 5 amino acids
( B ) TYPE: amino acid
( D ) TOPOLOGY: linear ( x i ) SEQUENCE DESCRIPTION: SEQ ID NO:120:

Lys His Ala Tyr Leu
1 5

( 2 ) INFORMATION FOR SEQ ID NO:121:

( i ) SEQUENCE CHARACTERISTICS:
( A ) LENGTH: 5 amino acids
( B ) TYPE: amino acid
( D ) TOPOLOGY: linear ( x i ) SEQUENCE DESCRIPTION: SEQ ID NO:121:

Tyr His Met Met Ala
1 5

( 2 ) INFORMATION FOR SEQ ID NO:122:

( i ) SEQUENCE CHARACTERISTICS:
( A ) LENGTH: 5 amino acids
( B ) TYPE: amino acid
( D ) TOPOLOGY: linear ( x i ) SEQUENCE DESCRIPTION: SEQ ID NO:122:

Tyr His Leu Lys Met
1 5

( 2 ) INFORMATION FOR SEQ ID NO:123:

( i ) SEQUENCE CHARACTERISTICS:
( A ) LENGTH: 5 amino acids
( B ) TYPE: amino acid
( D ) TOPOLOGY: linear ( x i ) SEQUENCE DESCRIPTION: SEQ ID NO:123:

Thr His Thr Thr Gln
1 5

( 2 ) INFORMATION FOR SEQ ID NO:124:

( i ) SEQUENCE CHARACTERISTICS:
( A ) LENGTH: 5 amino acids
( B ) TYPE: amino acid
( D ) TOPOLOGY: linear ( x i ) SEQUENCE DESCRIPTION: SEQ ID NO:124:

Lys His Tyr Thr Ile
1 5

( 2 ) INFORMATION FOR SEQ ID NO:125:

( i ) SEQUENCE CHARACTERISTICS:
( A ) LENGTH: 5 amino acids
( B ) TYPE: amino acid
( D ) TOPOLOGY: linear ( x i ) SEQUENCE DESCRIPTION: SEQ ID NO:125:

Gln His Tyr Val Asn
1 5

( 2 ) INFORMATION FOR SEQ ID NO:126:

( i ) SEQUENCE CHARACTERISTICS:
( A ) LENGTH: 5 amino acids
( B ) TYPE: amino acid
( D ) TOPOLOGY: linear ( x i ) SEQUENCE DESCRIPTION: SEQ ID NO:126:

Asp Gly Tyr His Leu 1 5

( 2 ) INFORMATION FOR SEQ ID NO:127:

( i ) SEQUENCE CHARACTERISTICS:
( A ) LENGTH: 5 amino acids
( B ) TYPE: amino acid
( D ) TOPOLOGY: linear ( x i ) SEQUENCE DESCRIPTION: SEQ ID NO:127:

Thr Ser Asn His Ile
1 5

( 2 ) INFORMATION FOR SEQ ID NO:128:

( i ) SEQUENCE CHARACTERISTICS:
( A ) LENGTH: 5 amino acids
( B ) TYPE: amino acid
( D ) TOPOLOGY: linear ( x i ) SEQUENCE DESCRIPTION: SEQ ID NO:128:

Leu Leu Arg His Thr
1 5

( 2 ) INFORMATION FOR SEQ ID NO:129:

( i ) SEQUENCE CHARACTERISTICS:
( A ) LENGTH: 5 amino acids
( B ) TYPE: amino acid
( D ) TOPOLOGY: linear ( x i ) SEQUENCE DESCRIPTION: SEQ ID NO:129:

Ala Thr Leu His Leu
1 5

( 2 ) INFORMATION FOR SEQ ID NO:130:

( i ) SEQUENCE CHARACTERISTICS:
( A ) LENGTH: 5 amino acids
( B ) TYPE: amino acid
( D ) TOPOLOGY: linear ( x i ) SEQUENCE DESCRIPTION: SEQ ID NO:130:

Ala Xaa Met His Met
1 5

( 2 ) INFORMATION FOR SEQ ID NO:131:

( i ) SEQUENCE CHARACTERISTICS:
( A ) LENGTH: 5 amino acids
( B ) TYPE: amino acid
( D ) TOPOLOGY: linear ( x i ) SEQUENCE DESCRIPTION: SEQ ID NO:131:

Thr Ser Met His Thr
1 5

( 2 ) INFORMATION FOR SEQ ID NO:132:

( i ) SEQUENCE CHARACTERISTICS:
( A ) LENGTH: 5 amino acids
( B ) TYPE: amino acid
( D ) TOPOLOGY: linear ( x i ) SEQUENCE DESCRIPTION: SEQ ID NO:132:

Tyr Ser Leu His Val
1 5

( 2 ) INFORMATION FOR SEQ ID NO:133:

( i ) SEQUENCE CHARACTERISTICS:
( A ) LENGTH: 5 amino acids
( B ) TYPE: amino acid
( D ) TOPOLOGY: linear ( x i ) SEQUENCE DESCRIPTION: SEQ ID NO:133:

Tyr Ala Met His Phe
1 5

( 2 ) INFORMATION FOR SEQ ID NO:134:

( i ) SEQUENCE CHARACTERISTICS:
( A ) LENGTH: 5 amino acids
( B ) TYPE: amino acid
( D ) TOPOLOGY: linear ( x i ) SEQUENCE DESCRIPTION: SEQ ID NO:134:

Phe Arg Ala Met His
1 5

( 2 ) INFORMATION FOR SEQ ID NO:135:

( i ) SEQUENCE CHARACTERISTICS:
( A ) LENGTH: 5 amino acids
( B ) TYPE: amino acid
( D ) TOPOLOGY: linear ( x i ) SEQUENCE DESCRIPTION: SEQ ID NO:135:

Ser Pro Ala Gln Asn
1 5

( 2 ) INFORMATION FOR SEQ ID NO:136:

( i ) SEQUENCE CHARACTERISTICS:
( A ) LENGTH: 5 amino acids
( B ) TYPE: amino acid
( D ) TOPOLOGY: linear ( x i ) SEQUENCE DESCRIPTION: SEQ ID NO:136:

Leu Ser Pro Asn Met
1 5

( 2 ) INFORMATION FOR SEQ ID NO:137:

( i ) SEQUENCE CHARACTERISTICS:
( A ) LENGTH: 5 amino acids
( B ) TYPE: amino acid
( D ) TOPOLOGY: linear ( x i ) SEQUENCE DESCRIPTION: SEQ ID NO:137:

Met Pro Arg Thr Phe
1 5

( 2 ) INFORMATION FOR SEQ ID NO:138:

( i ) SEQUENCE CHARACTERISTICS:
( A ) LENGTH: 5 amino acids
( B ) TYPE: amino acid
( D ) TOPOLOGY: linear ( x i ) SEQUENCE DESCRIPTION: SEQ ID NO:138:

Lys Ser Met Val Ala
1 5

( 2 ) INFORMATION FOR SEQ ID NO:139:

( i ) SEQUENCE CHARACTERISTICS:
( A ) LENGTH: 5 amino acids
( B ) TYPE: amino acid
( D ) TOPOLOGY: linear ( x i ) SEQUENCE DESCRIPTION: SEQ ID NO:139:

Ile Asn Asp Thr Leu
1 5

( 2 ) INFORMATION FOR SEQ ID NO:140:

( i ) SEQUENCE CHARACTERISTICS:
( A ) LENGTH: 5 amino acids
( B ) TYPE: amino acid
( D ) TOPOLOGY: linear ( x i ) SEQUENCE DESCRIPTION: SEQ ID NO:140:

Asp Val Asn Lys Pro
1 5

( 2 ) INFORMATION FOR SEQ ID NO:141:

( i ) SEQUENCE CHARACTERISTICS:
( A ) LENGTH: 5 amino acids
( B ) TYPE: amino acid
( D ) TOPOLOGY: linear ( x i ) SEQUENCE DESCRIPTION: SEQ ID NO:141:

Ala Arg Arg Thr Val
1 5

( 2 ) INFORMATION FOR SEQ ID NO:142:

( i ) SEQUENCE CHARACTERISTICS:
( A ) LENGTH: 5 amino acids
( B ) TYPE: amino acid
( D ) TOPOLOGY: linear ( x i ) SEQUENCE DESCRIPTION: SEQ ID NO:142:

Gly Asn Ser Gln Ser
1 5

( 2 ) INFORMATION FOR SEQ ID NO:143:

( i ) SEQUENCE CHARACTERISTICS:
( A ) LENGTH: 5 amino acids
( B ) TYPE: amino acid
( D ) TOPOLOGY: linear ( x i ) SEQUENCE DESCRIPTION: SEQ ID NO:143:

Glu Trp Ala Leu Leu
1 5

( 2 ) INFORMATION FOR SEQ ID NO:144:

( i ) SEQUENCE CHARACTERISTICS:
( A ) LENGTH: 5 amino acids
( B ) TYPE: amino acid
( D ) TOPOLOGY: linear ( x i ) SEQUENCE DESCRIPTION: SEQ ID NO:144:

Ile Ser Pro Leu Ile
1 5

( 2 ) INFORMATION FOR SEQ ID NO:145:

( i ) SEQUENCE CHARACTERISTICS:

( A ) LENGTH: 5 amino acids
( B ) TYPE: amino acid
( D ) TOPOLOGY: linear ( x i ) SEQUENCE DESCRIPTION: SEQ ID NO:145:

Ala Leu Met Asp Ser
1 5

( 2 ) INFORMATION FOR SEQ ID NO:146:

( i ) SEQUENCE CHARACTERISTICS:
( A ) LENGTH: 5 amino acids
( B ) TYPE: amino acid
( D ) TOPOLOGY: linear ( x i ) SEQUENCE DESCRIPTION: SEQ ID NO:146:

Thr Asn Phe Ser Ala
1 5

( 2 ) INFORMATION FOR SEQ ID NO:147:

( i ) SEQUENCE CHARACTERISTICS:
( A ) LENGTH: 5 amino acids
( B ) TYPE: amino acid
( D ) TOPOLOGY: linear ( x i ) SEQUENCE DESCRIPTION: SEQ ID NO:147:

Thr Gly Asn Asn Thr
1 5

( 2 ) INFORMATION FOR SEQ ID NO:148:

( i ) SEQUENCE CHARACTERISTICS:
( A ) LENGTH: 5 amino acids
( B ) TYPE: amino acid
( D ) TOPOLOGY: linear ( x i ) SEQUENCE DESCRIPTION: SEQ ID NO:148:

Ser Arg Ile Ser Leu
1 5

( 2 ) INFORMATION FOR SEQ ID NO:149:

( i ) SEQUENCE CHARACTERISTICS:
( A ) LENGTH: 5 amino acids
( B ) TYPE: amino acid
( D ) TOPOLOGY: linear ( x i ) SEQUENCE DESCRIPTION: SEQ ID NO:149:

Asn Leu Glu Leu Asn
1 5

( 2 ) INFORMATION FOR SEQ ID NO:150:

( i ) SEQUENCE CHARACTERISTICS:
( A ) LENGTH: 5 amino acids
( B ) TYPE: amino acid
( D ) TOPOLOGY: linear ( x i ) SEQUENCE DESCRIPTION: SEQ ID NO:150:

Val Tyr Ser Thr Asn
1 5

( 2 ) INFORMATION FOR SEQ ID NO:151:

( i ) SEQUENCE CHARACTERISTICS:
( A ) LENGTH: 5 amino acids
( B ) TYPE: amino acid -continued ( D ) TOPOLOGY: linear ( x i ) SEQUENCE DESCRIPTION: SEQ ID NO:151:

His Pro Ser Glu Pro
1 5

( 2 ) INFORMATION FOR SEQ ID NO:152:

( i ) SEQUENCE CHARACTERISTICS:
( A ) LENGTH: 5 amino acids
( B ) TYPE: amino acid
( D ) TOPOLOGY: linear ( x i ) SEQUENCE DESCRIPTION: SEQ ID NO:152:

Pro Ser Lys Ser Tyr
1 5

IDENTIFICATION OF NOVEL SUBSTRATES

CROSS REFERENCES

This application is a divisional of U.S. application Ser. No. 08/418,928 filed 5 Apr. 1995, which application is a continuation of U.S. application Ser. No. 08/161,692 filed 3 Dec. 1993 (abandoned), which application is a continuation of U.S. application Ser. No. 07/864,452 filed 6 Apr. 1992 (abandoned), which application is a continuation-in-part of U.S. application Ser. No. 08/050,058 filed 30 Apr. 1993, now U.S. Pat. No. 5,750,373, which application is a 371 of International Application No. PCT/US91/09133 filed 3 Dec. 1991, which application is a continuation-in-part of U.S. application Ser. No. 07/743,614 filed 9 Aug. 1991 (abandoned), which application is a continuation-in-part of U.S. application Ser. No. 07/715,300 filed 14 Jun. 1991 (abandoned), which application is a continuation-in-part of U.S. application Ser. No. 07/683,400 filed 10 Apr. 1991 (abandoned), which application is a continuation-in-part of U.S. application Ser. No. 07/621,667 filed 3 Dec. 1990 (abandoned), which applications are incorporated herein by reference and to which applications priority is claimed under 35 USC §120.

FIELD OF THE INVENTION

This invention relates to the preparation and systematic selection of improved substrates for enzymes. Specifically, this invention relates to methods for identifying substrates for enzymes with altered affinity.

BACKGROUND OF THE INVENTION

Variant polypeptide substrates having increased or decreased affinity for enzymes compared to their endogenous homologues are useful as therapeutic agonists and antagonists as well as for diagnostics. Methods for making non-naturally occurring variant substrates are often expensive and difficult requiring individual synthesis and testing of each compound. Considerable effort has been devoted to develop rapid and reliable methods for making and testing variant polypeptide substrates for pharmaceutically important enzymes.

Smith and coworkers (Smith, *Science,* 228: 1315–1317 (1985)) and Parmley and Smith, *Gene,* 73: 305–318 (1985) have demonstrated that small protein fragments (10–50 amino acids) can be "displayed" polyvalently on the surface of filamentous phage by inserting short gene fragments into gene III of the fd phage ("fusion phage"). The gene III minor coat protein (present in about 5 copies at one end of the virion) is important for proper phage assembly and for infection by attachment to the pili of *E. coli* (see Rasched et al., *Microbiol. Rev.,* 50: 401–427 (1986)). Recently, "fusion phage" have been shown to be useful for polyvalent display of short mutated peptide sequences for identifying peptides that may react with antibodies (Scott et al., *Science* 249: 386–390, (1990)) and Cwirla et al., *Proc. Natl. Acad. U.S.A* 87: 6378–6382, (1990)), or a foreign protein (Devlin et al., *Science,* 249: 404–406 (1990)).

There are, however, several important limitations in using such polyvalent "fusion phage" to identify altered peptides or proteins with new or enhanced binding properties. First, it has been shown (Parmley et al., *Gene,* 73: 305–318, (1988)) that fusion phage are useful only for displaying proteins of less than 100 and preferably less than 50 amino acid residues, because large inserts presumably disrupt the function of gene III and therefore phage assembly and infectivity. Second, prior art methods have been unable to select peptides from a library having the highest binding affinity for a target molecule. For example, after exhaustive panning of a random peptide library with an anti-β endorphin monoclonal antibody, Cwirla and co-workers could not separate moderate affinity peptides ($K_d$~10 μM) from higher affinity peptides ($K_d$~0.4 μM) fused to phage. The parent β-endorphin peptide sequence which has very high affinity ($K_d$~7 nM), was not panned from the epitope library. In addition, the infectivity of phage produced by polyvalent display can be dramatically reduced (<1% of wild-type) because the ability of the gene III protein to bind to the pili protein of *E. coli* can be impaired (McCafferty et al., *Nature* 348: 552–554 (1990); *Prot. Eng.* 4: 955–961 (1991)).

Ladner WO 90/02802 discloses a method for selecting novel binding proteins displayed on the outer surface of cells and viral particles where it is contemplated that the heterologous proteins may have up to 164 amino acid residues. The method contemplates isolating and amplifying the polyvalent displayed proteins to engineer a new family of binding proteins having desired affinity for a target molecule. More specifically, Ladner discloses a "fusion phage" polyvalently displaying proteins having "initial protein binding domains" ranging from 46 residues (crambin) to 164 residues (T4 lysozyme) fused to the M13 gene III coat protein. Ladner teaches the use of proteins "no larger than necessary" because it is easier to arrange restriction sites in smaller amino acid sequences and prefers the 58 amino acid residue bovine pancreatic trypsin inhibitor (BPTI). Small fusion proteins, such as BPTI, are preferred when the target is a protein or macromolecule, while larger fusion proteins, such as T4 lysozyme, are preferred for small target molecules such as steroids because such large proteins have clefts and grooves into which small molecules can fit. The preferred protein, BPTI, is proposed to be fused to gene III in a polyvalent fashion at the site disclosed by Smith et al. or de la Cruz et al., *J. Biol. Chem.,* 263: 4318–4322 (1988), or to one of the terminii. Ladner does not address the problem of successfully panning high affinity peptides from the random peptide library which plagues the biological selection and screening methods of the prior art.

Recently, Roberts et al., *PNAS, USA,* 89: 2429–2433 (1992) reported the use of phage display to select high affinity variants ($K_d$~1 pM) of bovine pancreatic trypsin inhibitor (BPTI) that bind human neutrophil elastase (HNE). A small library (~$5\times10^3$ independents) of BPTI variants was generated by mutagenesis of residues 15 to 19, which are known to interact with mammalian serine proteases from structural and functional data. The random mutagenesis scheme limited the scope of possible substitutions (~$10^3$ possible protein sequences) to those believed to enhance affinity for HNE based on prior mutational studies. After three rounds of sorting and differential pH elution, some variants were found that bound 50-fold tighter to HNE than those produced by structure-based design. The vector (SHOKUN2) which was not described, was designed for polyvalent display. This system was able to isolate mutants binding in the $10^{-12}$M range, in contrast to others' experience with polyvalent display (Cwirla et al., *PNAS, USA,* 87: 6378–6382 (1990); Bass et al., *Proteins: Struct., Funct. Genet.,* 8: 309–314 (1990); Barbas et al., *PNAS, USA,* 88: 7978–7982 (1991)). Multiple point attachment of BPTI-phage may have been avoided because of substantial degradation of BTPI on the phage. This is known to occur for polyvalent Fv-phage (McCafferty et al., *Nature,* 348: 552–554 (1990)) and alkaline phosphatase-phage (McCafferty et al., *Prot. Eng.,* 4: 955–961 (1991)) in which up to 95% of the fusion protein was degraded on the phage. Thus, some polyvalent display phage preparations contain mixtures of peptides whose display valencies are variable, irreproducible and unknown.

Accordingly, it is an object of this invention to provide a rapid and effective method for the systematic preparation of candidate variant enzyme substrates.

It is another object of this invention to prepare variant substrates displayed on surface of a phagemid particle that are conformationally stable.

It is also the object of this invention to provide "substrate-phage" that can be used to determine and prepare improved amino acid sequences surrounding a site of post translational modification.

It is still another object to prepare a family of related polypeptide substrates displayed on a phage which may be chemically or enzymatically modified such that their substrate characteristics are altered.

Finally, it is an object of this invention to produce a phagemid particle that rarely displays more than one copy of candidate binding proteins on the outer surface of the phagemid particle so that efficient and reproducible selection of high affinity binding proteins can be achieved.

These and other objects of this invention will be apparent from consideration of the invention as a whole.

SUMMARY OF THE INVENTION

Preferably in the method of this invention the plasmid is under tight control of the transcription regulatory element, and the culturing conditions are adjusted so that the amount or number of phagemid particles displaying more than one copy of the fusion protein on the surface of the particle is less than about 1%. Also preferably, amount of phagemid particles displaying more than one copy of the fusion protein is less than 10% the amount of phagemid particles displaying a single copy of the fusion protein. Most preferably the amount is less than 20%.

The objects of this invention have been achieved by providing a method for selecting novel polypeptides.

Briefly, the method consists of first constructing a replicable expression vector comprising a transcription regulatory element operably linked to a gene fusion, where the gene fusion comprises:

(i) a first gene encoding a polypeptide;

(ii) a second gene encoding a substrate peptide; and (iii) a third gene encoding at least a portion of a phage coat protein.

The 3' end of the first gene is linked to the 5' end of the second gene, and the 3' end of the second gene is linked to the 5' end of the third gene.

The method further consists of mutating the vector at one or more selected positions within the second gene thereby forming a family of related plasmids encoding substrate peptides.

Next, suitable host cells are transformed with the plasmids, and the transformed host cells are infected the with a helper phage having a gene encoding the phage coat protein. The transformed infected host cells are cultured under conditions suitable for forming recombinant phagemid particles containing at least a portion of the plasmid. Preferably, the conditions are adjusted so that no more than a minor amount of phagemid particles display more than one copy of the fusion protein on the surface of the particle.

The phagemid particles are then exposed to at least one protease, and the family of protease treated phagemid particles are contacted with an affinity molecule, where the affinity molecule has affinity for the polypeptide encoded by the first gene.

Finally, the phagemid particles that bind to the affinity molecule are separated from those that do not.

Optionally the method further comprises determining the rate of proteolytic hydrolysis of those particles that do not bind. Also optionally, The method further comprises determining the site of hydrolysis, and optionally determining the sequence surrounding the site of hydrolysis.

Optionally, the foregoing method may be repeated one or more times with either the phagemid particle that bound to the affinity molecule or those that did not.

The polypeptide is typically selected from; human growth hormone(hGH), N-methionyl human growth hormone, bovine growth hormone, parathyroid hormone, thyroxine, insulin A-chain, insulin B-chain, proinsulin, relaxin A-chain, relaxin B-chain, prorelaxin, glycoprotein hormones such as follicle stimulating hormone(FSH), thyroid stimulating hormone(TSH), and leutinizing hormone(LH), glycoprotein hormone receptors, calcitonin, glucagon, factor VIII, an antibody, lung surfactant, urokinase, streptokinase, human tissue-type plasminogen activator (t-PA), bombesin, factor IX, thrombin, hemopoietic growth factor, tumor necrosis factor-alpha and -beta, enkephalinase, human serum albumin, mullerian-inhibiting substance, mouse gonadotropin-associated peptide, a microbial protein, such as betalactamase, tissue factor protein, inhibin, activin, vascular endothelial growth factor, receptors for hormones or growth factors; integrin, thrombopoietin, protein A or D, rheumatoid factors, nerve growth factors such as NGF-b, platelet-growth factor, transforming growth factors (TGF) such as TGF-alpha and TGF-beta, insulin-like growth factor-I and -II, insulin-like growth factor binding proteins, CD4, DNase, latency associated peptide, erythropoietin, osteoinductive factors, interferons such as interferon-alpha, -beta, and -gamma, colony stimulating factors (CSFs) such as M-CSF, GM-CSF, and G-CSF, interleukins (ILs) such as IL-1, IL-2, IL-3, IL-4, superoxide dismutase; decay accelerating factor, viral antigen, HIV envelope proteins such as GP120, GP140, atrial natriuretic peptides A, B or C, immunoglobulins, or derivatives thereof.

Preferably, the protease is selected from; HIV protease, thrombin, human neutrophil elastase and other serine proteases, Factor Xa, tissue plasminogen activator (t-PA), urokinase, streptokinase, angiotensin converting enzyme and other metalloproteases, prohormone converting enzymes selected from pancreatic protease and enterokinase, and subtilisin.

Optionally, the polypeptide may be derivatized with a substituent capable of binding with an affinity molecule.

Also optionally, instead of being treated with a protease, the phagemid particles are exposed to a process capable of modifying at least one covalent bond of an amino acid in the substrate peptide followed by contacting the family of exposed phagemid particles with an affinity molecule, where the affinity molecule has affinity for the amino acid residue having the modified covalent bond. Thereafter, the phagemid particles that bind are separated from those that do not. Preferably, the process is a post-translational covalent bond modifying process selected from phosphorylation, glycosylation, carboxylation, ADP-ribosylation, methylation, isoprenylation and acylation. Optionally, the modified amino acid residue is derivatized with a substituent capable of binding with an affinity molecule.

BRIEF DESCRIPTION OF THE FIGURES

FIG. 10B. A schematic diagram of the entire plasma pDH188 containing the insert described in 5A. After transformation of the plasmid into *E. coli* SR101 cells and the addition of helper phage, the plasmid is packaged into phage particles. Some of these particles display the $F_{ab}$-p III fusion (where p III is the protein encoded by the M13 gene III DNA). The segments in the plasmid figure correspond to the insert shown in 5A.

FIGS. 11A through 11H show the sequence of DNA encoding the 4D5 antibody of Example XI are collectively referred to here as FIG. 11. The nucleotide (Seq. ID No. 25) sequence of the DNA encoding the 4D5 $F_{ab}$ molecule expressed on the phagemid surface. The amino acid sequence of the light chain is also shown (Seq. ID No. 26), as is the amino acid sequence of the heavy chain p III fusion (Seq. ID No. 27).

DETAILED DESCRIPTION OF THE INVENTION

Figure 14:
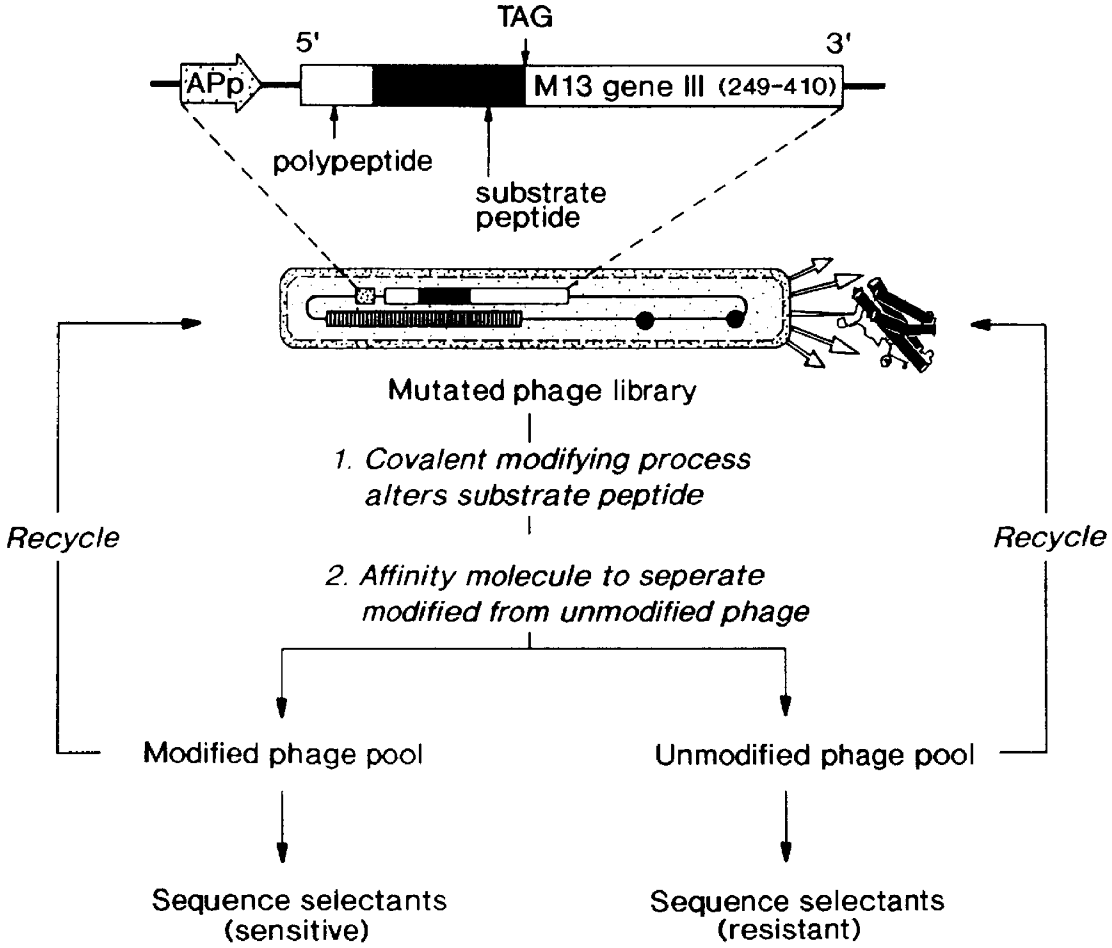
FIG. 14. Schematic diagram of one embodiment of the invention. DNA encoding a first gene (polypeptide) is fused to DNA encoding a peptide substrate which in turn is fused to DNA encoding at least a portion of the phage M13 gene 3 coat protein or other phage coat protein. One or more codons of the substrate peptide may by imitated. Expression of this fusion protein is driven by the alkaline phosphatase (APp) or other promoter. The DNA encoding these three genes is inserted into a suitable vector which is incorporated into a phagemid, and the fusion protein is expressed on the surface of the phagemid particles. The phagemid particle are then exposed to a protease or other covalent modifying process, which may alter the substrate peptide. An immobilized affinity molecule is then used to separate modified from unmodified phage.

The following discussion will be best understood by referring to FIG. 14. In its simplest form, the method of the instant invention comprises a method for rapidly producing many substrate peptides. Those with the desired characteristics can rapidly be selected, and their sequences identified. To accomplish this, the wild-type substrate peptide or a random peptide of suitable length is obtained and fused at its 5' end to the 3' end of a polypeptide. The 3' end of the substrate peptide is fused to a phage coat protein or portion thereof. All of this DNA, fused together, is then inserted into a suitable vestor. The vector is transformed into *E. coli* or other acceptable host cells to which helper phage is added. A portion of this vector containing the DNA encoding the fusion protein is then packaged into the phage, thereby generating phagemid particles which express the fusion protein on their surface.

The substrate peptide, and optionally, the polypeptide, may be mutated at one or more positions to generate a family of mutated plasmids, each of which then be expressed on the surface of a phagemid particle. The mutant fusion proteins are then exposed to a protease which may or may not recognize and cleave the mutant substrate peptide. If cleavage does occur, the polypeptide (encoded by gene 1) will become dissociated from the phagemid particle, and, when the phagemid particle is contacted with an affinity molecule specific for the polypeptide, it will not bind. However, if cleavage does not occur because the protease does not recognize the mutant substrate peptide, the polypeptide encoded be gene 1 will not be dissociated, and, when the phagemid particle is contacted with an affinity molecule specific for the polypeptide, it will not bind. However, if cleavage does not occur because the protease does not recognize the mutant substrate peptide, the polypeptide encoded by gene 1 will not be dissociated, and, when the phagemid particle is contacted with the affinity molecule, binding will occur.

It is possible that there will be competing sites of proteolysis recognized by the protease on the phage coat protein itself, or on the polypeptide. This problem can be solved by mutating this competing site to make it protease resistant. In this regard it should be mentioned that the phage itself is extraordinarily resistant to proteolysis as it has been battling endogenous *E. coli* proteases throughout evolution.

In addition, it is important to note that the *E. coli* expression system can "edit-out" good protease substrates or those that impair the folding of the affinity domain. To limit some of these problems it may be desirable to use protease deficient strains of *E. coli* so that substrate-phage cannot be cleaved endogenously. One way to diagnose such editing is to identify whether there is a distinct lack of particular amino acid residue(s) in both the sensitive and resistant substrate phage pools. For example, the fact that Cys and Trp are missing from both resistant and sensitive substrate-phage pools suggests they have been edited out by the phage.

I. Choice of Polypeptides for the First Gene (gene I)

This invention contemplates any polypeptide that binds to an affinity molecule, and includes antibodies. Preferred polypeptides include; a growth hormone, including human growth hormone, des-N-methionyl human growth hormone, and bovine growth hormone; parathyroid hormone; thyroid stimulating hormone; thyroxine; insulin A-chain; insulin B-chain; proinsulin; follicle stimulating hormone; calcitonin; leutinizing hormone; glucagon; factor VIII; an antibody; lung surfactant; a plasminogen activator, such as urokinase or human tissue-type plasminogen activator (t-PA); bombesin; factor IX, thrombin; hemopoietic growth factor; tumor necrosis factor-alpha and -beta; enkephalinase; a serum albumin such as human serum albumin; mullerian-inhibiting substance; relaxin A-chain; relaxin B-chain; prorelaxin; mouse gonadotropin-associated peptide; a microbial protein, such as betalactamase; tissue factor protein; inhibin; activin; vascular endothelial growth factor; receptors for hormones or growth factors; integrin; thrombopoietin; protein A or D; rheumatoid factors; nerve growth factor such as NGF-β; platelet-derived growth factor; fibroblast growth factor such as aFGF and bFGF; epidermal growth factor; transforming growth factor (TGF) such as TGF-alpha and TGF-beta; insulin-like growth factor-I and -II; insulin-like growth factor binding proteins; CD4; DNase; latency associated peptide; erythropoietin; osteoinductive factors; an interferon such as interferon-alpha, -beta, and -gamma; colony stimulating factors (CSFs), e.g., M-CSF, GM-CSF, and G-CSF; interleukins (ILs), e.g., IL-1, IL-2, IL-3, IL-4, etc.; superoxide dismutase; decay accelerating factor; atrial natriuretic peptides A, B or C; viral antigen such as, for example, a portion of the HIV envelope; immunoglobulins; and fragments of any of the above-listed polypeptides. In addition, one or more predetermined amino acid residues on the polypeptide may be substituted, inserted, or deleted, for example, to produce products with improved biological properties. Further, fragments and derivatives of these polypeptides, especially biologically active fragments, are included. Yet more preferred polypeptides of this invention are human growth hormone, and atrial naturetic peptides A, B, and C, endotoxin. It is most preferred that the polypeptide not be a protease.

II. Selection of Substrate Peptide

The substrate peptides contemplated in this invention are peptide sequences of at least three amino acids in length. Each sequences in its wild-type or naturally occurring form, is acted on by any enzyme that cleaves peptide bonds (although other types of enzymes which act by chemically modifying their substrates rather than hydrolyzing them are included in the scope of this invention as are their specific substrates.) Thus, included in the scope of this invention are any peptide sequences that are cut or cleaved by any naturally occurring or synthetic proteinase including α-aminoacylpeptide hydrolases, peptidylamino-acid or acylamino-acid hydrolases, dipeptide hydrolase, dipeptidylpeptide hydrolases, peptidylpeptide hydrolases, serine carboxypeptidases, metallo-carboxypeptidases, serine proteinases, thiolproteinases, carboxyl (acid) proteinases, metalloproteinases, and other proteinases of unknown catalytic mechanism. Preferred substrates are those which are recognized and cut by by HIV protease, thrombin, human neutrophil elastase and other serine proteases, Factor Xa, tissue plasminogen activator (t-PA), urokinase, streptokinase, angiotensin converting enzyme and other metalloproteases, prohormone converting enzymes such as pancreatic protease and enterokinase, and subtilisin.

Most preferred substances are those recognized and cleaved by HIV protease, thrombin, human netrophil elastase, and substilisin.

III. Obtaining a First Gene (Gene 1) Encoding the Desired Polypeptide and a Second Gene Encoding the Substrate Peptide The gene encoding the polypeptide can be obtained by methods known in the art (see generally, Sambrook et al., *Molecular Biology: A Laboratory Manual*, Cold Spring Harbor Press, Cold Spring Harbor, N.Y. (1989)). If the sequence of the gene is known, the DNA encoding the gene may be chemically synthesized. Engels et al. (*Agnew. Chem. Int. Ed. Engl.,* 28: 716–734 [1989]), specifically incorporated by reference. These methods include triester, phosphite, phosphoramidite and H-Phosphonate methods, PCR and other sutoprimer methods, and oligonucleotide syntheses on solid supports. If the sequence of the gene is not known, or if the gene has not previously been isolated, it may be cloned from a cDNA library (made from RNA obtained from a suitable tissue in which the desired gene is expressed) or from a suitable genomic DNA library. The gene is then isolated using an appropriate probe. For cDNA libraries, suitable probes include monoclonal or polyclonal antibodies (provided that the cDNA library is an expression library), oligonucleotides, and complementary or homologous cDNAs or fragments thereof. The probes that may be used to isolate the gene of interest from genomic DNA libraries include cDNAs or fragments thereof that encode the same or a similar gene, homologous genomic DNAs or DNA fragments, and oligonucleotides. Screening the cDNA or genomic library with the selected probe is conducted using standard procedures as described in chapters 10–12 of Sambrook et al., supra.

An alternative means to isolating the gene encoding the polypeptide is to use polymerase chain reaction methodology (PCR) as described in section 14 of Sambrook et al., supra. This method requires the use of oligonucleotides that will hybridize to the gene of interest; thus, at least some of the DNA sequence for this gene must be known in order to generate the oligonucleotides.

Any of the methods discussed immediately above may be used to obtain the DNA encoding the substrate peptide. However, in most cases, this DNA sequence will be relatively short, coding for 3 to 10 amino acids. Thus, the most expedient method to obtain this DNA may be by chemical synthesis.

After each gene has been isolated, it may be inserted into a suitable vector (preferably a plasmid) for amplification, as described generally in Sambrook et al., supra. Prior to insertion into the vector, it may be preferable to first ligate these together using methods described below.

IV. Constructing Replicable Expression Vectors

While several types of vectors are available and may be used to practice this invention, plasmid vectors are the preferred vectors for use herein, as they may be constructed with relative ease, and can be readily amplified. Plasmid vectors generally contain a variety of components including promoters, signal sequences, phenotypic selection genes, origin of replication sites, and other necessary components as are known to those of ordinary skill in the art.

Promoters most commonly used in prokaryotic vectors include the lac Z promoter system, the alkaline phosphatase pho A promoter, the bacteriophage λPL promoter (a temperature sensitive promoter), the tac promoter (a hybrid trp-lac promoter that is regulated by the lac repressor), the tryptophan promoter, and the bacteriophage T7 promoter. For general descriptions of promoters, see section 17 of Sambrook et al. supra. While these are the most commonly used promoters, other suitable microbial promoters may be used as well.

Preferred promoters for practicing this invention are those that can be tightly regulated such that expression of the fusion gene can be controlled. It is believed that the problem that went unrecognized in the prior art was that display of multiple copies of the fusion protein on the surface of the phagemid particle lead to multipoint attachment of the phagemid with the target. It is believed this effect, referred to as the "chelate effect", results in selection of false "high affinity" polypeptides when multiple copies of the fusion protein are displayed on the phagemid particle in close proximity to one another so that the target was "chelated". When multipoint attachment occurs, the effective or apparent Kd may be as high as the product of the individual Kds for each copy of the displayed fusion protein. This effect may be the reason Cwirla and coworkers supra were unable to separate moderate affinity peptides from higher affinity peptides.

It has been discovered that by tightly regulating expression of the fusion protein so that no more than a minor amount, i.e. fewer than about 1%, of the phagemid particles contain multiple copies of the fusion protein the "chelate effect" is overcome allowing proper selection of high affinity polypeptides. Thus, depending on the promoter, culturing conditions of the host are adjusted to maximize the number of phagemid particles containing a single copy of the fusion protein and minimize the number of phagemid particles containing multiple copies of the fusion protein.

Preferred promoters used to practice this invention are the lac Z promoter and the pho A promoter. The lac Z promoter is regulated by the lac repressor protein lac i, and thus transcription of the fusion gene can be controlled by manipulation of the level of the lac repressor protein. By way of illustration, the phagemid containing the lac Z promotor is grown in a cell strain that contains a copy of the lac i repressor gene, a repressor for the lac Z promotor. Exemplary cell strains containing the lac i gene include JM 101 and XL1-blue. In the alternative, the host cell can be cotransfected with a plasmid containing both the repressor lac i and the lac Z promotor. Occasionally both of the above techniques are used simultaneously, that is, phagmide particles containing the lac Z promoter are grown in cell strains containing the lac i gene and the cell strains are cotransfected with a plasmid containing both the lac Z and lac i genes. Normally when one wishes to express a gene, to the transfected host above one would add an inducer such as isopropylthiogalactoside (IPTG). In the present invention however, this step is omitted to (a) minimize the expression of the gene III fusion protein thereby minimizing the copy number (i.e. the number of gene III fusions per phagemid number) and to (b) prevent poor or improper packaging of the phagemid caused by inducers such as IPTG even at low concentrations. Typically, when no inducer is added, the number of fusion proteins per phagemid particle is about 0.1 (number of bulk fusion proteins/number of phagemid particles). The most preferred promoter used to practice this invention is pho A. This promoter is believed to be regulated by the level of inorganic phosphate in the cell where the phosphate acts to down-regulate the activity of the promoter. Thus, by depleting cells of phosphate, the activity of the promoter can be increased. The desired result is achieved by growing cells in a phosphate enriched medium such as 2 YT or LB thereby controlling the expression of the gene III fusion.

One other optional component of vectors used to practice this invention is a signal sequence. This sequence is typically located immediately 5' to the gene encoding the polypeptide (first gene) fusion protein, and will thus be transcribed at the amino terminus of the fusion protein. However, in certain cases, the signal sequence has been demonstrated to be located at positions other 5' to the gene encoding the protein to be secreted. This sequence targets the protein to which it is attached across the inner membrane of the bacterial cell. The DNA encoding the signal sequence may be obtained as a restriction endonuclease fragment from any gene encoding a protein that has a signal sequence. Suitable prokaryotic signal sequences may be obtained from genes encoding, for example, LamB or OmpF (Wong et al., *Gene,* 68: 193 (1983)), MalE, PhoA and other genes. A preferred prokaryotic signal sequence for practicing this invention is the *E. coli* heat-stable enterotoxin II (STII) signal sequence as described by Chang et al. , *Gene,* 55: 189 (1987).

Another useful component of the vectors used to practice this invention is phenotypic selection genes. Typical phenotypic selection genes are those encoding proteins that confer antibiotic resistance upon the host cell. By way of illustration, the ampicillin resistance gene (amp), and the tetracycline resistance gene (tet) are readily employed for this purpose.

Construction of suitable vectors comprising the aforementioned components as well as the gene encoding the desired polypeptide (gene 1) are prepared using standard recombinant DNA procedures as described in Sambrook et al. supra. Isolated DNA fragments to be combined to form the vector are cleaved, tailored, and ligated together in a specific order and orientation to generate the desired vector.

The DNA is cleaved using the appropriate restriction enzyme or enzymes in a suitable buffer. In general, about 0.2–1 $\mu$g of plasmid or DNA fragments is used with about 1–2 units of the appropriate restriction enzyme in about 20 $\mu$l of buffer solution. Appropriate buffers, DNA concentrations, and incubation times and temperatures are specified by the manufacturers of the restriction enzymes. Generally, incubation times of about one or two hours at 37° C. are adequate, although several enzymes require higher temperatures. After incubation, the enzymes and other contaminants are removed by extraction of the digestion solution with a mixture of phenol and chloroform, and the DNA is recovered from the aqueous fraction by precipitation with ethanol.

To ligate the DNA fragments together to form a functional vector, the ends of the DNA fragments must be compatible with each other. In some cases, the ends will be directly compatible after endonuclease digestion. However, it may be necessary to first convert the sticky ends commonly produced by endonuclease digestion to blunt ends to make them compatible for ligation. To blunt the ends, the DNA is treated in a suitable buffer for at least 15 minutes at 15° C. with 10 units of of the Klenow fragment of DNA polymerase I (Klenow) in the presence of the four deoxynucleotide triphosphates. The DNA is then purified by phenol-chloroform extraction and ethanol precipitation.

The cleaved DNA fragments may be size-separated and selected using DNA gel electrophoresis. The DNA may be electrophoresed through either an agarose or a polyacrylamide matrix. The selection of the matrix will depend on the size of the DNA fragments to be separated. After electrophoresis, the DNA is extracted from the matrix by electroelution, or, if low-melting agarose has been used as the matrix, by melting the agarose and extracting the DNA from it, as described in sections 6.30–6.33 of Sambrook et al., supra.

The DNA fragments that are to be ligated together (previously digested with the appropriate restriction enzymes such that the ends of each fragment to be ligated are compatible) are put in solution in about equimolar amounts. The solution will also contain ATP, ligase buffer and a ligase such as T4 DNA ligase at about 10 units per 0.5 μg of DNA. If the DNA fragment is to be ligated into a vector, the vector is at first linearized by cutting with the appropriate restriction endonuclease(s). The linearized vector is then treated with alkaline phosphatase or calf intestinal phosphatase. The phosphatasing prevents self-ligation of the vector during the ligation step.

After ligation, the vector with the foreign gene now inserted is transformed into a suitable host cell. Prokaryotes are the preferred host cells for this invention. Suitable prokaryotic host cells include *E. coli* strain JM101, *E. coli* K12 strain 294 (ATCC number 31,446), *E. coli* strain W3110 (ATCC number 27,325), *E. coli* X1776 (ATCC number 31,537), *E. coli* XL-1Blue (stratagene), and *E. coli* B; however many other strains of *E. coli*, such as HB101, NM522, NM538, NM539, and many other species and genera of prokaryotes may be used as well. In addition to the *E. coli* strains listed above, bacilli such as *Bacillus subtilis*, other enterobacteriaceae such as *Salmonella typhimurium* or *Serratia marcesans*, and various Pseudomonas species may all be used as hosts.

Transformation of prokaryotic cells is readily accomplished using the calcium chloride method as described in section 1.82 of Sambrook et al., supra. Alternatively, electroporation (Neumann et al., *EMBO J.,* 1: 841 (1982)) may be used to transform these cells. The transformed cells are selected by growth on an antibiotic, commonly tetracycline (tet) or ampicillin (amp), to which they are rendered resistant due to the presence of tet and/or amp resistance genes on the vector.

After selection of the transformed cells, these cells are grown in culture and the plasmid DNA (or other vector with the foreign gene inserted) is then isolated. Plasmid DNA can be isolated using methods known in the art. Two suitable methods are the small scale preparation of DNA and the large-scale preparation of DNA as described in sections 1.25–1.33 of Sambrook et al., supra. The isolated DNA can be purified by methods known in the art such as that described in section 1.40 of Sambrook et al., supra. This purified plasmid DNA is then analyzed by restriction mapping and/or DNA sequencing. DNA sequencing is generally performed by either the method of Messing et al. *Nucleic Acids Res.,* 9: 309 (1981) or by the method of Maxam et al. *Meth. Enzymol.,* 65: 499 (1980).

V. Gene Fusion

This invention contemplates fusing two or three genes together such that a fusion protein is generated during transcription. Gene 3 is typically a coat protein gene of a phage, and preferably it is the phage M13 gene III coat protein, or a fragment thereof. Fusion of genes 1, 2 and 3 may be accomplished by inserting gene 2 into a particular site on a plasmid that contains gene 1, or by inserting gene 1 into a particular site on a plasmid that contains gene 2.

Insertion of a gene into a plasmid requires that the plasmid be cut at the precise location that the gene is to be inserted. Thus, there must be a restriction endonuclease site at this location (preferably a unique site such that the plasmid will only be cut at a single location during restriction endonuclease digestion). The plasmid is digested, phosphatased, and purified as described above. The gene is then inserted into this linearized plasmid by ligating the two DNAs together. Ligation can be accomplished if the ends of the plasmid are compatible with the ends of the gene to be inserted. If the restriction enzymes are used to cut the plasmid and isolate the gene to be inserted create blunt ends or compatible sticky ends, the DNAs can be ligated together directly using a ligase such as bacteriophage T4 DNA ligase and incubating the mixture at 16° C. for 1–4 hours in the presence of ATP and ligase buffer as described in section 1.68 of Sambrook et al., supra. If the ends are not compatible, they must first be made blunt by using the Klenow fragment of DNA polymerase I or bacteriophage T4 DNA polymerase, both of which require the four deoxyribonucleotide triphosphates to fill-in overhanging single-stranded ends of the digested DNA. Alternatively, the ends may be blunted using a nuclease such as nuclease S1 or mung-bean nuclease, both of which function by cutting back the overhanging single strands of DNA. The DNA is then religated using a ligase as described above. In some cases, it may not be possible to blunt the ends of the gene to be inserted, as the reading frame of the coding region will be altered. To overcome this problem, oligonucleotide linkers may be used. The linkers serve as a bridge to connect the plasmid to the gene to be inserted. These linkers can be made synthetically as double stranded or single stranded DNA using standard methods. The linkers have one end that is compatible with the ends of the gene to be inserted; the linkers are first ligated to this gene using ligation methods described above. The other end of the linkers is designed to be compatible with the plasmid for ligation. In designing the linkers, care must be taken to not destroy the reading frame of the gene to be inserted or the reading frame of the gene contained on the plasmid. In some cases, it may be necessary to design the linkers such that they code for part of an amino acid, or such that they code for one or more amino acids.

VI. Alteration (Mutation) of Genes at Selected Positions

Gene 2, encoding the substrate peptide, may be altered at one or more selected codons. In some embodiments of the present invention, Gene 1, encoding a polypeptide, may also be mutated. An alteration is defined as a substitution, deletion, or insertion of one or more codons in the gene encoding the polypeptide that results in a change in the amino acid sequence of the polypeptide as compared with the unaltered or native sequence of the same polypeptide. Preferably, the alterations will be by substitution of at least one amino acid with any other amino acid in one or more regions of the molecule. The alterations may be produced be a variety of methods known in the art. These methods include but are not limited to oligonucleotide-mediated mutagenesis and cassette mutagenesis.

A. Oligonucleotide-Mediated Mutagenesis

Oligonucleotide-mediated mutagenesis is preferred method for preparing substitution, deletion, and insertion variants of gene 1. This technique is well known in the art as described by Zoller et al. Nucleic Acids Res. 10: 6487–6504 (1987). Briefly, gene 1 is altered by hybridizing an oligonucleotide encoding the desired mutation to a DNA template, where the template is the single-stranded form of the plasmid containing the unaltered or native DNA sequence of gene 1. After hybridization, a DNA polymerase is used to synthesize an entire second complementary strand of the template will thus incorporate the oligonucleotide primer, and will code for the selected alteration in gene 1.

Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al. *Proc. Nat'l. Acad. Sci. USA,* 75: 5765 (1978).

The DNA template can only be generated by those vectors that are either derived from bacteriophage M13 vectors (the commercially available M13mp18 and M13mp19, vectors are suitable), or those vectors that contain a single-stranded phage origin of replication as described by Viera et al. *Meth. Enzymol.,* 153: 3 (1987). Thus, the DNA that is to be mutated must be inserted into one of these vectors in order to generate single-stranded template. Production of the single-stranded template is described in sections 4.21–4.41 of Sambrook et al., supra.

To alter the native DNA sequence, the oligonucleotide is hybridized to the single stranded template under suitable hybridization conditions. A DNA polymerizing enzyme, usually the Klenow fragment of DNA polymerase I, is then added to synthesize the complementary strand of the template using the oligonucleotide as a primer for synthesis. A heteroduplex molecule is thus formed such that one strand of DNA encodes the mutated form of gene 1, and the other strand (the original template) encodes the native, unaltered sequence of gene 1. This heteroduplex molecule is then transformed into a suitable host cell, usually a prokaryote such as *E. Coli* JM101. After growing the cells, they are plated onto agarose plates and screened using the oligonucleotide primer radiolabelled with 32-Phosphate to identify the bacterial colonies that contain the mutated DNA.

The method described immediately above may be modified such that a homoduplex molecule is created wherein both strands of the plasmid contain the mutation(s). The modifications are as follows: The single-stranded oligonucleotide is annealed to the single-stranded template as described above. A mixture of three deoxyribonucleotides, deoxyriboadenosine (dATP), deoxyriboguanosine (dGTP), and deoxyribothymidine (dTTP), is combined with a modified thio-deoxyribocytosine called dCTP-(aS) (which can be obtained from Amersham). This mixture is added to the template-oligonucleotide complex. Upon addition of DNA polymerase to this mixture, a strand of DNA identical to the template except for the mutated bases is generated. In addition, this new strand of DNA will contain dCTP-(aS) instead of dCTP, which serves to protect it from restriction endonuclease digestion. After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell such as *E. coli* JM101, as described above.

Mutants with more than one amino acid to be substituted may be generated in one of several ways. If the amino acids are located close together in the polypeptide chain, they may be mutated simultaneously using one oligonucleotide that codes for all of the desired amino acid substitutions. If, however, the amino acids are located some distance from each other (separated by more than about ten amino acids), it is more difficult to generate a single oligonucleotide that encodes all of the desired changes. Instead, one of two alternative methods may be employed.

In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions. The alternative method involves two or more rounds of mutagenesis to produce the desired mutant. The first round is as described for the single mutants: wild-type DNA is used for the template, an oligonucleotide encoding the first desired amino acid substitution(s) is annealed to this template, and the heteroduplex DNA molecule is then generated. The second round of mutagenesis utilizes the mutated DNA produced in the first round of mutagenesis as the template. Thus, this template already contains one or more mutations. The oligonucleotide encoding the additional desired amino acid substitution(s) is then annealed to this template, and the resulting strand of DNA now encodes mutations from both the first and second rounds of mutagenesis. This resultant DNA can be used as a template in a third round of mutagenesis, and so on.

B. Cassette Mutagenesis

This method is also a preferred method for preparing substitution, deletion, and insertion variants of gene 1. The method is based on that described by Wells et al. *Gene,* 34:315 (1985). The starting material is the plasmid (or other vector) comprising gene 1, the gene to be mutated. The codon(s) in gene 1 to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in gene 1. After the restriction sites have been introduced into the plasmid, the plasmid is cut at these sites to linearize it. A double-stranded oligonucleotide encoding the sequence of the DNA between the restriction sites but containing the desired mutation(s) is synthesized using standard procedures. The two strands are synthesized separately and then hybridized together using standard techniques. This double-stranded oligonucleotide is referred to as the cassette. This cassette is designed to have 3' and 5' ends that are compatible with the ends of the linearized plasmid, such that it can be directly ligated to the plasmid. This plasmid now contains the mutated DNA sequence of gene 1.

VII. Obtaining DNA encoding Polypeptides with More Than One Subunit

In an alternative embodiment, this invention contemplates the use of polypeptides containing one or more subunits. Each subunit is typically encoded by separate gene. Each gene encoding each subunit can be obtained by methods known in the art as described above. In some instances, it may be necessary to obtain the gene encoding the various subunits using separate techniques selected from any of the methods described in Section II.

When constructing a replicable expression vector where the polypeptide contains more than one subunit, all subunits can be regulated by the same promoter, typically located 5' to the DNA encoding the subunits, or each may be regulated by separate promoter suitably oriented in the vector so that each promoter is operably linked to the DNA it is intended to regulate. Selection of promoters is carried out as described in above.

When constructing a family of variants of the multi-subunit polypeptide, DNA encoding each subunit in the vector may mutated in one or more positions in each subunit. When multi-subunit antibody variants are constructed, preferred sites of mutagenesis correspond to codons encoding amino acid residues located in the complementarity-determining regions (CDR) of either the light chain, the heavy chain, or both chains. The CDRs are commonly referred to as the hypervariable regions. Methods for mutagenizing DNA encoding each subunit of the polypeptide are conducted essentially as described in Section V above.

VII. Preparing an Affinity Molecule

The affinity molecule contemplated in this invention includes any type of molecule that has specific affinity for the polypeptide encoded by gene 1. Such molecules may include, but are not limited to, polypeptides such as receptors (especially where gene 1 encodes a hormone polypeptide), or antibodies, preferably monoclonal, although polyclonals that are highly specific for the polypeptide, may also be employed.

Proteinaceous affinity molecules such as polypeptide receptors, may be isolated from natural sources or prepared by recombinant methods by procedures known in the art. By way of illustration, glycoprotein hormone receptors may be prepared by the technique described by McFarland et al., *Science* 245: 494–499 (1989), nonglycosylated forms expressed in *E. coli* are described by Fuh et al. J. Biol. Chem 265: 3111–3115 (1990). Other receptors and antibodies can be prepared by standard methods.

The affinity molecule may be nonproteinaceous as well. For example, if the polypeptide contains free sulfhydryl groups, the affinity molecule may be p-chloromercuribenzoate, or immobilized biotin when the polypeptide is avidin. Alternatively, if the polypeptide is a dye binding hydrophobic protein, immobilized Cibacron Blue may be used, or an immobilized substrate (e.g. Immobilized mannose for mannan binding protein or immobilized meilbiose for α-galactosidase). The polypeptide may also be a monoclonal antibody specific for an immobilized nonproteinaceous ligand. Many other such affinity molecules will be apparent to one of ordinary skill.

Optionally, the polypeptide may be derivitized for binding with either a proteinacious or nonproteinaceous affinity molecule. For example, the polypeptide may be glycosylated either enzymatically or nonenzymatically and the phagemid particles so produced contacted with a boronate affinity gel. Alternatively the polypeptide may be biotinylated with NHS-biotin for binding with the affinity molecule, an immobilized avidin. Also optionally, the polypeptide may be linked to the immobilized affinity molecule through a homo- or heterobifunctional cleavable cross-linker such as dimethyldithiobispropionimidate or disulfosuccinimidyltartrate (see the Pierce general catalogue). Many other methods of derivitizing and binding the polypeptide to the affinity molecule will be readily apparent to the skilled artisan.

In an alternative embodiment, attachment or binding to the affinity molecule may occur through the substrate peptide encoded by the second gene. This is especially appropriate when a functional group such as a phosphate or carbohydrate is enzymatically added as it is during post-translational modification. Here the modified phagemid particles may be bound directly to the affinity molecule or the functional group may be first derivitized and then bound to the affinity molecule. In the former case a monoclonal antibody specific for phosphotyrosine may be employed as the affinity molecule to isolate phagemid particles whose substrate peptides were successfully phosphorylated at Tyr. Alternatively, when the posttranslational modification is a glycosylation the affinity molecule may be an immobilized boronate. Optionally, the carbohydrate may be modified with a cleavable bifunctional crosslinker and contacted with a suitable immobilized matrix.

The purified affinity molecule may be attached to a suitable matrix such as agarose beads, acrylamide beads, glass beads, cellulose, various acrylic copolymers, hydroxylalkyl methacrylate gels, polyacrylic and polymethacrylic copolymers, nylon, neutral and ionic carriers, and the like. Attachment of the affinity molecule to the matrix may be accomplished by methods such as those described in *Methods in Enzymology,* 44 (1976), or by other means known in the art. Attachment of the affinity molecule to the matrix serves to immobilize the affinity molecule.

After attachment of the affinity molecule to the matrix, the family of phagemid particles previously treated with protease, are contacted with the affinity molecule matrix under conditions suitable for binding of at least a portion of the phagemid particles. Normally, the conditions, including pH, ionic strength, temperature and the like will mimic these physiological conditions to which the polypeptide normally is surrounded.

Bound phagemid particles ("binders") having high affinity for the immobilized affinity molecule matrix are separated from those having a low affinity (and thus do not bind to the affinity molecule) by washing. Binders may be dissociated from the immobilized affinity molecule by a variety of methods. These methods include competitive dissociation using for example the wild-type ligand, a higher affinity ligand, soluble ligand, altering pH and/or ionic strength, and other methods known in the art.

Suitable host cells are infected with the binders or non-binders and helper phage, and the host cells are cultured under conditions suitable for amplification of the phagemid particles. The phagemid particles are then collected and the selection process is repeated one or more times until binders having the desired affinity for the affinity molecule matrix are selected. Or, in the case of non-binders, until adequate amplification and/or purification selected substrate peptide sequence(s) has been achieved.

IX. Uses of the Invention

This invention contemplates generating novel substrate peptide sequences. The sequences are generated randomly and all possible naturally occurring amino acids may be substituted into each position that is mutated.

The resultant products are then exposed to naturally occurring or mutated proteases (or other enzymes that naturally "act" upon the native or wild-type form of the substrate).

The protease may act upon the substrate by cutting it, or because of the mutation. The protease may no longer 'recognize' the substrate and thus will not be able to cut it. Of those sequences it does recognize, it may cut some faster than others, as it may have a greater affinity for some of these.

The sequences not cut by proteases, the "resistant" sequences are useful as "inhibition" sequences. These sequences may be engineered into pharmaceutically important proteins (that are naturally protease susceptible) to make them protease resistant.

The sequences that are cut by proteases, the "sensitive" sequences, are useful as improved substrates for assay or diagnostic kits. Such kits may be used for example in detection of protease activity in various bodily fluids such as blood or urine, and in various bodily tissues and cell types.

Optionally, the sequences that are cut best ie the "best" substrates may be chemically altered at the sessile peptide bond so that it resists hydrolysis thereby producing a good competitive inhibitor for the protease.

EXAMPLES

Without further description, it is believed that one of ordinary skill in the art can, using the preceding description and illustrative examples, make and utilize the present invention to the fullest extent. The following working examples therefore specifically point out preferred embodiments of the present invention, and are not to be construed as limiting in any way of the remainder of the disclosure.

Example I

Plasmid Constructions and Preparation of hGH-phagemid Particles

The plasmid phGH-M13gIII (FIG. 1), was constructed from M13KO7 and the hGH producing plasmid, pBO473 (Cunningham, B. C., et al., *Science,* 243: 1330–1336, (1989) ). A synthetic oligonucleotide 5'-AGC-TGT-GGC-TTC-GGG-CCC-TTA-GCA-TTT-AAT-GCG-GTA-3' (SEQ ID NO:6) was used to introduce a unique ApaI restriction site (underlined) into pBO473 after the final Phe191 codon of hGH. The oligonucleotide 5'-TTC-ACA-AAC-GAA-GGG-CCC-CTA-ATT-AAA-GCC-AGA-3' (SEQ ID NO:7) was used to introduce a unique ApaI restriction site (underlined), and a Glu197-to-amber stop codon (bold lettering) into M13KO7 gene III. The oligonucleotide 5'-CAA-TAA-TAA-CGG-GCT-AGC-CAA-AAG-AAC-TGG-3' (SEQ ID NO:8) introduces a unique NheI site (underlined) after the 3' end of the gene III coding sequence. The resulting 650 base pair (bp) ApaI-NheI fragment from the doubly mutated M13KO7 gene III was cloned into the large ApaI-NheI fragment of pBO473 to create the plasmid, pSO132. This fuses the carboxyl terminus of hGH (Phe191) to the Pro198 residue of the gene III protein with the insertion of a glycine residue encoded from the ApaI site and places the fusion protein under control of the *E. coli* alkaline phosphatase (phoA) promoter and stII secretion signal sequence (Chang, C. N., et al., *Gene,* 55: 189–196, (1987)). For inducible expression of the fusion protein in rich media, the phoA promoter was replaced with the lac promoter and operator. A 138 bp EcoRI-XbaI fragment containing the lac promoter, operator, and Cap binding site was produced by PCR of plasmid pUC119 using the oligonucleotides 5'-CACGACA GAATTCCCGACTGGAAA-3' (SEQ ID NO:9) and 5'-CTGTT TCTAGAGTGAAATTGTTA-3' (SEQ ID NO:10) that flank the desired lac sequences and introduce the EcoRI and XbaI restriction sites (underlined). This lac fragment was gel purified and ligated into the large EcoRI-XbaI fragment of pSO132 to create the plasmid, phGH-M13gIII. The sequences of all tailored DNA junctions were verified by the dideoxy sequence method (Sanger, F., et al. *Proc. Natl. Acad. Sci. U.S.A.* 74: 5463–5467, (1977)). The R64A variant hGH phagemid was constructed as follows: the NsiI-BglII mutated fragment of hGH (Cunninghamet al. supra) encoding the Arg64 to Ala substitution (R64A) (Cunningham, B. C., Wells, J. A., *Science* 244: 1081–1085, (1989)) was cloned between the corresponding restriction sites in the phGH-M13gIII plasmid (FIG. 1) to replace the wild-type hGH sequence. The R64A hGH phagemid particles were propagated and titered as described below for the wild-type hGH-phagemid.

Plasmids were transformed into a male strain of *E. coli* (JM101) and selected on carbenicillin plates. A single transformant was grown in 2 ml 2 YT medium for 4 h at 37° C. and infected with 50 μl of M13KO7 helper phage. The infected culture was diluted into 30 ml 2 YT, grown overnight, and phagemid particles were harvested by precipitation with polyethylene glycol (Vierra, J., Messing, J., *Methods in Enzymology,* 153: 3–11, (1987)). Typical phagemid particle titers ranged from 2 to $5\times10^{11}$ cfu/ml. The particles were purified to homogeneity by CsCl density centrifugation (Day, L. A. *J. Mol. Biol.,* 39: 265–277, (1969)) to remove any fusion protein not attached to virions.

Example II

Immunochemical Analyses of hGH on the Fusion Phage

Rabbit polyclonal antibodies to hGH were purified with protein A, and coated onto microtiter plates (Nunc) at a concentration of 2 μg/ml in 50 mM sodium carbonate buffer (pH 10) at 4° C. for 16–20 hours. After washing in PBS containing 0.05% Tween 20, hGH or hGH-phagemid particles were serially diluted from 2.0–0.002 nM in buffer A (50 mM Tris (pH 7.5), 50 mM NaCl, 2 mM EDTA, 5 mg/ml bovine serum albumin, and 0.05% Tween 20). After 2 hours at room temperature (rt), the plates were washed well and the indicated Mab (Cunningham et al. supra) was added at 1 μg/ml in buffer A for 2 hours at rt. Following washing, horseradish peroxidase conjugated goat anti-mouse IgG antibody was bound at rt for 1 hour. After a final wash, the peroxidase activity was assayed with the substrate, o-phenylenediamine.

Example III

Coupling of the hGH Binding Protein to Polyacrylamide Beads

Oxirane polyacrylamide beads (Sigma) were conjugated to the purified extracellular domain of the hGH receptor (hGHbp) (Fuh, G., et al., *J. Biol. Chem.* 265: 3111–3115 (1990)) containing an extra cysteine residue introduced by site-directed mutagenesis at position 237 that does not affect binding of hGH (J. Wells, unpublished). The hGHbp was conjugated as recommended by the supplier to a level of 1.7 pmol hGHbp/mg dry oxirane bead, as measured by binding of ($^{125}$I) hGH to the resin. Subsequently, any unreacted oxirane groups were blocked with BSA and Tris. As a control for non-specific binding of phagemid particles, BSA was similarly coupled to the beads. Buffer for adsorption and washing contained 10 mM Tris.HCl (pH 7.5), 1 mM EDTA, 50 mM NaCl, 1 mg/ml BSA, and 0.02% Tween 20. Elution buffers contained wash buffer plus 200 nM hGH or 0.2M glycine (pH 2.1). Parental phage M13KO7 was mixed with hGH phagemid particles at a ratio of nearly 3000:1 (original mixture) and tumbled for 8–12 h with a 5 μl aliquot (0.2 mg of acrylamide beads) of either absorbent in a 50 μl volume at room temperature. The beads were pelleted by centrifugation and the supernate carefully removed. The beads were resuspended in 200 μl wash buffer and tumbled at room temperature for 4 hours (wash 1). After a second wash (wash 2), the beads were eluted twice with 200 nM hGH for 6–10 hours each (eluate 1, eluate 2). The final elution was with a glycine buffer (pH 2.1) for 4 hours to remove remaining hGH phagemid particles (eluate 3). Each fraction was diluted appropriately in 2 YT media, mixed with fresh JM101, incubated at 37° C. for 5 minutes, and plated with 3 ml of 2 YT soft agar on LB or LB carbenicillin plates.

Example IV

Construction of hGH-phagemid Particles with a Mixture of Gene III Products

Figure 1:
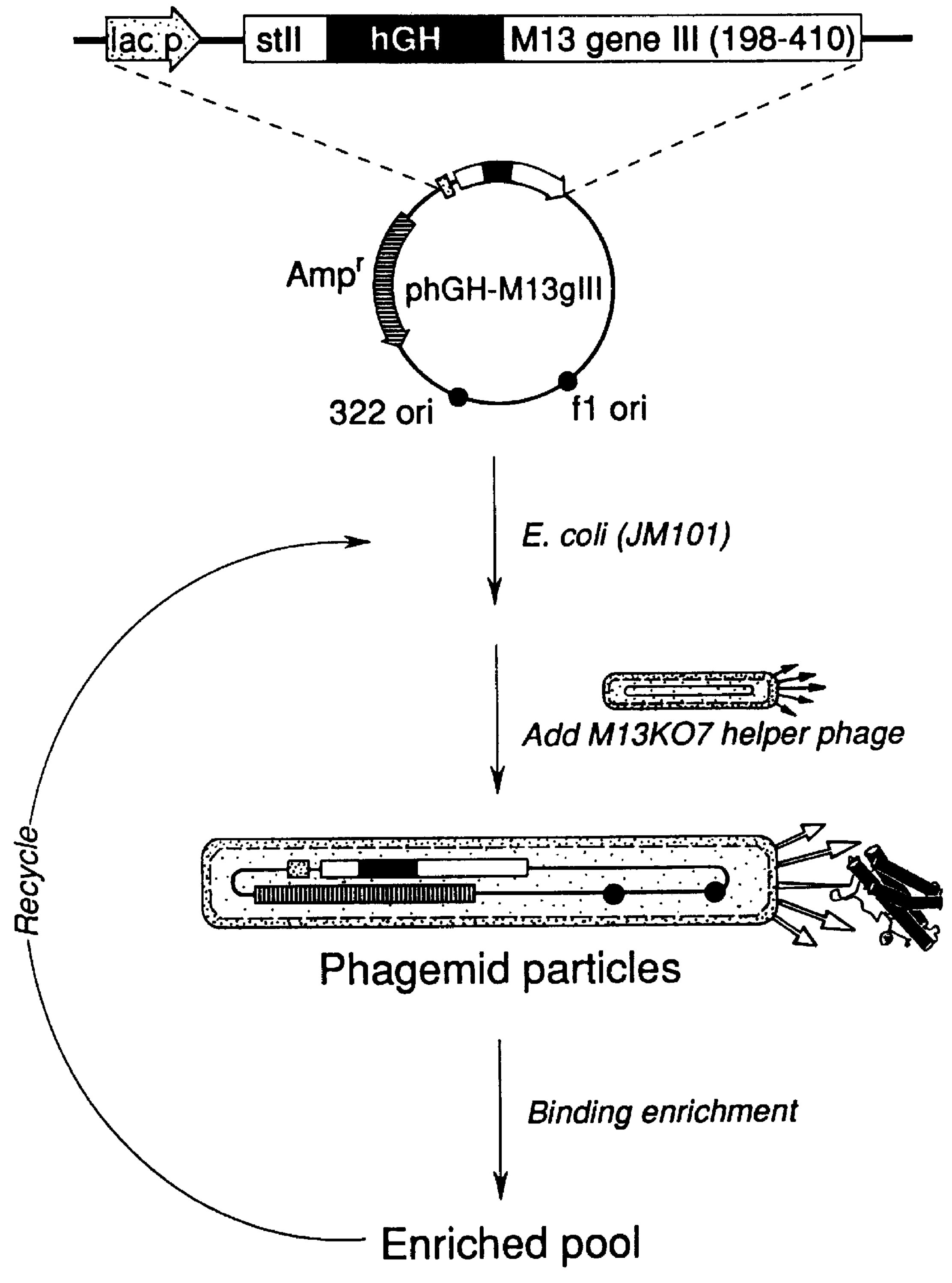
FIG. 1. Strategy for displaying large proteins on the surface of filamentous phage and enriching for altered receptor binding properties. A plasmid, phGH-M13gIII was constructed that fuses the entire coding sequence of hGH to the carboxyl terminal domain of M13 gene III. Transcription of the fusion protein is under control of the lac promoter/operator sequence, and secretion is directed by the stII signal sequence. Phagemid particles are produced by infection with the "helper" phage, M13KO7, and particles displaying hGH can be enriched by binding to an affinity matrix containing the hGH receptor. The wild-type gene III (derived from the M13KO7 phage) is diagramed by 4–5 copies of the multiple arrows on the tip of the phage, and the fusion protein (derived from the phagemid, phGH-M13gIII) is indicated schematically by the folding diagram of hGH replacing the arrow head.

The gene III protein is composed of 410 residues divided into two domains that are separated by a flexible linker sequence (Armstrong, J., et al., *FEBS Lett.,* 135: 167–172, (1981)). The amino-terminal domain is required for attachment to the pili of *E. coli,* while the carboxyl-terminal domain is imbedded in the phage coat and required for proper phage assembly (Crissman, J. W., Smith, G. P., *Virology,* 132: 445–455, (1984)). The signal sequence and amino-terminal domain of gene III was replaced with the stII signal and entire hGH gene (Chang et al. supra) by fusion to residue 198 in the carboxyl-terminal domain of gene III (FIG. 1). The hGH-gene III fusion was placed under control of the lac promoter/operator in a plasmid (phGH-M13gIII; FIG. 1) containing the pBR322 β-lactamase gene and Col E1 replication origin, and the phage f1 intergenic region. The vector can be easily maintained as a small plasmid vector by selection on carbenicillin, which avoids relying on a functional gene III fusion for propagation. Alternatively, the plasmid can be efficiently packaged into virions (called phagemid particles) by infection with helper phage such as M13KO7 (Viera et al. supra) which avoids problems of phage assembly. Phagemid infectivity titers based upon transduction to carbenicillin resistance in this system varied from $2–5\times10^{11}$ colony forming units (cfu)/ml. The titer of the M13KO7 helper phage in these phagemid stocks is $\sim10^{10}$ plaque forming units (pfu)/ml.

With this system was confirmed previous studies (Parmley, Smith supra) that homogeneous expression of large proteins fused to gene III is deleterious to phage production (data not shown). For example, induction of the lac promoter in phGH-M13gIII by addition of IPTG produced low phagemid titers. Moreover, phagemid particles produced by co-infection with M13KO7 containing an amber mutation in gene III gave very low phagemid titers ($<10^{10}$ cfu/ml). It was believed that multiple copies of the gene III fusion attached to the phagemid surface could lead to multiple point attachment (the "chelate effect") of the fusion phage to the immobilized affinity molecule. Therefore to control the fusion protein copy number, transcription of the hGH-gene III fusion was limited by culturing the plasmid in *E. coli* JM101 ($lacI^Q$) which contains a constitutively high level of the lac repressor protein. The *E. coli* JM101 cultures containing phGH-M13gIII were best propagated and infected with M13KO7 in the absence of the lac operon inducer (IPTG); however, this system is flexible so that co-expression of other gene III fusion proteins can be balanced. It was estimated that about 10% of the phagemid particles contain one copy of the hGH gene III fusion protein from the ratio of the amount of hGH per virion (based on hGH immunoreactive material in CsCl gradient purified phagemid). Therefore, the titer of fusion phage displaying the hGH gene III fusion is about $2–5\times10^{10}$/ml. This number is much greater than the titer of *E. coli* ($\sim10^8$ to $10^9$/ml) in the culture from which they are derived. Thus, on average every *E. coli* cell produces 10–100 copies of phage decorated with an hGH gene III fusion protein.

Example V

Structural Integrity of the hGH-gene III Fusion

Figures 2A, 2B:
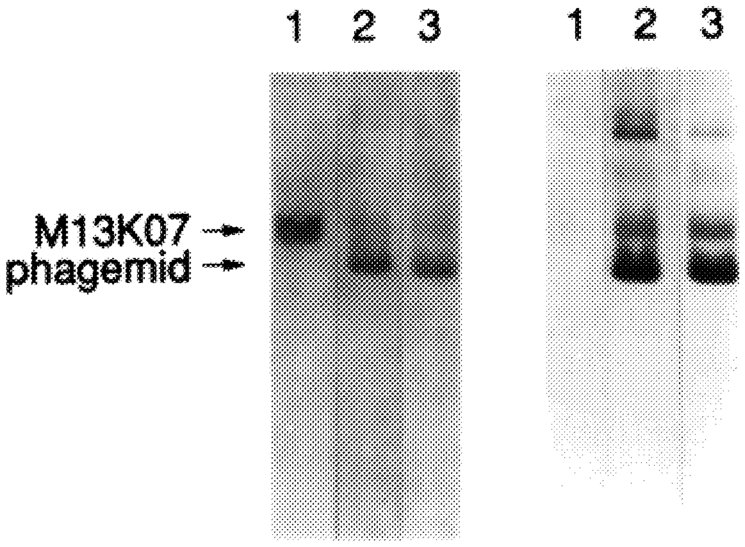
FIGS. 2A and 2B. Immunoblot of whole phage particles shows that hGH comigrates with phage. Phagemid particles purified in a cesium chloride gradient were loaded into duplicate wells and electrophoresed through a 1% agarose gel in 375 mM Tris, 40 mM glycine pH 9.6 buffer. The gel was soaked in transfer buffer (25 mM Tris, pH 8.3, 200 mM glycine, 20% methanol) containing 2% SDS and 2% β-mercaptoethanol for 2 hours, then rinsed in transfer buffer for 6 hours. The proteins in the gel were then electroblotted onto immobilon membranes (Millipore). The membrane containing one set of samples was stained with Coomassie blue to show the position of the phage proteins (FIG. 2A). The duplicate membrane was immuno-stained for hGH by reacting the membrane with polyclonal rabbit anti-hGH antibodies followed by reaction with horseradish peroxidase conjugated goat anti-rabbit IgG antibodies (FIG. 2B). Lane 1 contains the M13KO7 parent phage and is visible only in the Coomassie blue stained membrane, since it lacks hGH. Lanes 2 and 3 contain separate preparations of the hormone phagemid particles which is visible both by Coomassie and hGH immuno-staining. The difference in migration distance between the parent M13KO7 phage and hormone phagemid particles reflects the different size genomes that are packaged within (8.7 kb vs. 5.1 kb, respectively).

Immunoblot analysis (FIGS. 2A and B) of the hGH-gene III phagemid show that hGH cross-reactive material comigrates with phagemid particles in agarose gels. This indicates that the hGH is tightly associated with phagemid particles. The hGH-gene III fusion protein from the phagemid particles runs as a single immuno-stained band showing that there is little degradation of the hGH when it is attached to gene III. Wild-type gene III protein is clearly present because about 25% of the phagemid particles are infectious. This is comparable to specific infectivity estimates made for wild-type M13 phage that are similarly purified (by CsCl density gradients) and concentrations estimated by UV absorbance (Smith, G. P. supra and Parmley, Smith supra) Thus, both wild-type gene III and the hGH-gene III fusion proteins are displayed in the phage pool.

It was important to confirm that the tertiary structure of the displayed hGH was maintained in order to have confidence that results from binding selections will translate to the native protein. Monoclonal antibodies (Mabs) to hGH were used to evaluate the structural integrity of the displayed hGH gene III fusion protein (Table I).

TABLE I

Binding of Eight Different Monoclonal Antibodies (Mab's) to hGH and hGH Phagemid Particles*

| | $IC_{50}$ (nM) | |
|---|---|---|
| Mab | hGH | hGH-phagemid |
| 1 | 0.4 | 0.4 |
| 2 | 0.04 | 0.04 |
| 3 | 0.2 | 0.2 |
| 4 | 0.1 | 0.1 |
| 5 | 0.2 | >2.0 |
| 6 | 0.07 | 0.2 |
| 7 | 0.1 | 0.1 |
| 8 | 0.1 | 0.1 |

*Values given represent the concentration (nM) of hGH or hGH-phagemid particles to give half-maximal binding to the particular Mab. Standard errors in these measurements are typically at or below ±30% of the reported value. See Materials and Methods for further details.

The epitopes on hGH for these Mabs have been mapped (Cunningham et al. supra) and binding for 7 of 8 Mabs requires that hGH be properly folded. The $IC_{50}$ values for all Mabs were equivalent to wild-type hGH except for Mab 5 and 6. Both Mabs 5 and 6 are known to have binding determinants near the carboxyl-terminus of hGH which is blocked in the gene III fusion protein. The relative $IC_{50}$ value for Mab1 which reacts with both native and denatured hGH is unchanged compared to the conformationally sensitive Mabs 2–5, 7 and 8. Thus, Mab1 serves as a good internal control for any errors in matching the concentration of the hGH standard to that of the hGH-gene III fusion.

Example VI

Binding Enrichments on Receptor Affinity Beads

Previous workers (Parmley, Smith supra; Scott, Smith supra; Cwirla et al. supra; and Devlin et al. supra) have fractionated phage by panning with streptavidin coated polystyrene petri dishes or microtiter plates. However, chromatographic systems would allow more efficient fractionation of phagemid particles displaying mutant proteins with different binding affinities. Non-porous oxirane beads were chosen (Sigma) to avoid trapping of phagemid particles in the chromatographic resin. Furthermore, these beads have a small particle size (1 μm) to maximize the surface area to mass ratio. The extracellular domain of the hGH receptor (hGHbp) (Fuh et al., supra) containing a free cysteino residue was efficiently coupled to these beads and phagemid particles showed very low non-specific binding to beads coupled only to bovine serum albumin (Table II).

TABLE II

Specific Binding of Hormone Phage to hGHbp-coated Beads Provides an Enrichment for hGH-Phage Over M13KO7 Phage*

| Sample | Absorbent‡ | Total pfu | Total cfu | Ratio (cfu/pfu) | Enrichment§ |
|---|---|---|---|---|---|
| Original mixture† | | $8.3 \times 10^{11}$ | $2.9 \times 10^{8}$ | $3.5 \times 10^{-4}$ | (1) |
| Supernatant | BSA | $7.4 \times 10^{11}$ | $2.8 \times 10^{8}$ | $3.8 \times 10^{-4}$ | 1.1 |
| | hGHbp | $7.6 \times 10^{11}$ | $3.3 \times 10^{8}$ | $4.3 \times 10^{-4}$ | 1.2 |
| Wash 1 | BSA | $1.1 \times 10^{10}$ | $6.0 \times 10^{6}$ | $5.5 \times 10^{-4}$ | 1.6 |
| | hGHbp | $1.9 \times 10^{10}$ | $1.7 \times 10^{7}$ | $8.9 \times 10^{-4}$ | 2.5 |
| Wash 2 | BSA | $5.9 \times 10^{7}$ | $2.8 \times 10^{4}$ | $4.7 \times 10^{-4}$ | 1.3 |
| | hGHbp | $4.9 \times 10^{7}$ | $2.7 \times 10^{6}$ | $5.5 \text{ X } 10^{-2}$ | $1.6 \times 10^{2}$ |
| Eluate 1 (hGH) | BSA | $1.1 \times 10^{6}$ | $1.9 \times 10^{3}$ | $1.7 \times 10^{-3}$ | 4.9 |
| | hGHbp | $1.2 \times 10^{6}$ | $2.1 \times 10^{6}$ | 1.8 | $5.1 \times 10^{3}$ |
| Eluate 2 (hGH) | BSA | $5.9 \times 10^{5}$ | $1.2 \times 10^{3}$ | $2.0. \times 10^{-3}$ | 5.7 |
| | hGHbp | $5.5 \times 10^{5}$ | $1.3 \times 10^{6}$ | 2.4 | $6.9 \times 10^{3}$ |
| Eluate 3 (pH 2.1) | BSA | $4.6 \times 10^{5}$ | $2.0 \times 10^{3}$ | $4.3 \times 10^{-3}$ | 12.3 |
| | hGHbp | $3.8 \times 10^{5}$ | $4.0 \times 10^{6}$ | 10.5 | $3.0 \times 10^{4}$ |

*The titers of M13KO7 and hGH-phagemid particles in each fraction was determined by multiplying the number of plaque forming units (pfu) or carbenicillin resistant colony forming units (cfu) by the dilution factor, respectively. See Example IV for details.
†The ratio of M13KO7 to hGH-phagemid particles was adjusted to 3000:1 in the original mixture.
‡Absorbents were conjugated with BSA or hGHbp.
§Enrichments are calcutated by dividing the cfu/pfu ratio after each step by cfu/pfu ratio in the original mixture.

In a typical enrichment experiment (Table II), one part of hGH phagemid was mixed with >3,000 parts M13KO7 phage. After one cycle of binding and elution, $10^6$ phage were recovered and the ratio of phagemid to M13KO7 phage was 2 to 1. Thus, a single binding selection step gave >5000-fold enrichment. Additional elutions with free hGH or acid treatment to remove remaining phagemids produced even greater enrichments. The enrichments are comparable to those obtained by Smith and coworkers using batch elution from coated polystyrene plates (Smith, G. P. supra and Parmely, Smith supra ) however much smaller volumes are used on the beads (200 $\mu$l vs. 6 ml). There was almost no enrichment for the hGH phagemid over M13KO7 when beads linked only to BSA were used. The slight enrichment observed for control beads (~10-fold for pH 2.1 elution; Table 2) may result from trace contaminants of bovine growth hormone binding protein present in the BSA linked to the bead. Nevertheless these data show the enrichments for the hGH phage depend upon the presence of the hGHbp on the bead suggesting binding occurs by specific interaction between hGH and the hGHbp.

The enrichment for wild-type hGH over a weaker binding variant of the hGH on fusion phagemids was evaluated to further demonstrate enrichment specificity, and to link the reduction in binding affinity for the purified hormones to enrichment factors after panning fusion phagemids. A fusion phagemid was constructed with an hGH mutant in which Arg64 was substituted with Ala (R64A). The R64A variant hormone is about 20-fold reduced in receptor binding affinity compared to hGH (Kd values of 7.1 nM and 0.34 nM, respectively (Cunningham, Wells, supra)). The titers of the R64A hGH-gene III fusion phagemid were comparable to those of wild-type hGH phagemid. After one round of binding and elution (Table E) the wild-type hGH phagemid was enriched from a mixture of the two phagemids plus M13KO7 by 8-fold relative to the phagemid R64A, and ~$10^4$ relative to M13KO7 helper phage.

TABLE III hGHbp-Coated Beads Select for hGH Phagemids Over a Weaker Binding hGH Variant Phagemid

| | Control beads | | hGHbp beads | |
|---|---|---|---|---|
| Sample | WT phagemid / total phagemid | enrichment for WT/R64A | WT phagemid / total phagemid | enrichment for WT/R64A |
| Original mixture | 8/20 | (1) | 8/20 | (1) |
| Supernatant ND | | — | 4/10 | 1.0 |
| Elution 1 (hGH) | 7/20 | 0.8 | 17/20 | 8.5‡ |
| Elution 2 (pH 2.1) | 11/20 | 1.8 | 21/27 | 5.2 |

*The parent M13KO7 phage, wild-type hGH phagemid and R64A phagemid particles were mixed at a ratio of $10^4$:0.4:0.6. Binding selections were carried out using beads linked with BSA (control beads) or with the hGHbp (hGHbp beads) as described in Table II and the Materiais and Methods After each step, plasmid DNA was isolated(Birnboim, H. C., Doly, J., Nucleic Acids Res., 7:1513–1523, (1979)) from carbenicillin resistant colonies and analyzed by restriction analysis to determine if it contained the wild-type hGH or the R64A hGH gene III fusion.
†The enrichment for wild-type hGH phagemid over R64A mutant was calculated from the ratio of hGH phagemid present after each step to that present in the original mixture (8/20), divided by the corresponding ratio for R64A phagemids. WT = wild-type; ND = not determined.
‡The enrichment for phagemid over total M13KO7 parental phage was ~$10^4$ after this step.

By displaying a mixture of wild-type gene III and the gene III fusion protein on phagemid particles one can assemble and propagate virions that display a large and proper folded protein as a fusion to gene III. The copy number of the gene III fusion protein can be effectively controlled to avoid “chelate effects” yet maintained at high enough levels in the phagemid pool to permit panning of large epitope libraries (>$10^{10}$). The data here show that hGH (a 22 kD protein) can be displayed in its native folded form. Binding selections performed on receptor affinity beads eluted with free hGH, efficiently enriched for wild-type hGH phagemids over a mutant hGH phagemid shown to have reduced receptor binding affinity. Thus, it is possible to sort phagemid particles whose binding constants are down in the nanomolar range.

Protein-protein and antibody-antigen interactions are dominated by discontinuous epitopes (Janin, J., et al., *J. Mol. Biol.,* 204: 155–164, (1988); Argos, P., *Prot. Eng.,* 2: 101–113, (1988); Barlow, D. J., et al., *Nature.* 322: 747–748, (1987); and Davies, D. R., et al., *J. Biol. Chem.* 263: 10541–10544, (1988)); that is the residues directly involved in binding are close in tertiary structure but separated by residues not involved in binding. The screening system presented here should allow one to analyze more conveniently protein-receptor interactions and isolate discontinuous epitopes in proteins with new and high affinity binding properties.

Example VII

Selection of hGH Mutants from a Library Randomized at hGH Codons 172, 174, 176, 178

Construction of template

A mutant of the hGH-gene III fusion protein was constructed using the method of Kunkel., et al. *Meth. Enzymol.* 154, 367–382 (1987). Template DNA was prepared by growing the plasmid pS0132 (containing the natural hGH gene fused to the carboxy-terminal half of M13 gene III, under control of the alkaline phosphatase promoter) in CJ236 cells with M13-K07 phage added as helper. Single-stranded, uracil-containing DNA was prepared for mutagenesis to introduce (1) a mutation in hGH which would greatly reduce binding to the hGH binding protein (hGHbp); and (2) a unique restriction site (KpnI) which could be used for assaying for—and selecting against—parental background phage. Oligonucleotide-directed mutagenesis was carried out using T7 DNA polymerase and the following oligodeoxy-nucleotide

```
                                       Gly  Thr
hGH codon:                             178  179
           5'-G  ACA  TTC  CTG  GGT  ACC  GTG  CAG  T-3'
                                    < KpnI >
                                          (SEQ ID NO:11)
```

This oligo introduces the KpnI site as shown, along with mutations (R178G, I179T) in hGH. These mutations are predicted to reduce binding of hGH to hGHbp by more than 30-fold. Clones from the mutagenesis were screened by KpnI digestion and confirmed by dideoxy DNA sequencing. The resulting construct, to be used as a template for random mutagenesis, was designated pHO415.

Random mutagenesis within helix-4 of hGH

Codons 172, 174, 176, 178 were targeted for random mutagenesis in hGH, again using the method of Kunkel. Single-stranded template from pH0415 was prepared as above and mutagenesis was carried out using the following pool of oligos:

As shown, this oligo pool reverts codon 179 to wild-type (Ile), destroys the unique KpnI site of pH0415, and introduces random codons (NNS, where N=A,G,C, or T and S=G or C) at positions 172,174,176, and 178. Using this codon selection in the context of the above sequence, no additional KpnI sites can be created. The choice of the NNS degenerate sequence yields 32 possible codons (including one "stop" codon, and at least one codon for each amino acid) at 4 sites, for a total of $(32)^4$=1,048,576 possible nucleotide sequences (12% of which contain at least one stop codon), or $(20)^4$=160,000 possible polypeptide sequences plus 34,481 prematurely terminated sequences (i.e. sequences containing at least one stop codon).

Propagation of the initial library

The mutagenesis products were extracted twice with phenol:chloroform (50:50) and ethanol precipitated with an excess of carrier tRNA to avoid adding salt that would confound the subsequent electroporation step. Approximately 50 ng (15 fmols) of DNA was electroporated into WJM101 cells ($2.8\times10^{10}$ cells/mL) in 45 $\mu$L total volume in a 0.2 cm cuvette at a voltage setting of 2.49 kV with a single pulse (time constant=4.7 msec.).

The cells were allowed to recover 1 hour at 37° C. with shaking, then mixed with 25 mL 2 YT medium, 100 $\mu$g/mL carbenicillin, and M13-K07 (multiplicity of infection=1000). Plating of serial dilutions from this culture onto carbenicllin-containing media indicated that $8.2\times10^6$ electrotransformants were obtained. After 10' at 23° C., the culture was incubated overnight (15 hours) at 37° C. with shaking.

After overnight incubation, the cells were pelleted, and double-stranded DNA (dsDNA), designated pLIB1, was prepared by the alkaline lysis method. The supernatant was spun again to remove any remaining cells, and the phage, designated phage pool ϕ1, were PEG-precipitated and resuspended in 1 mL STE buffer (10 mM Tris, pH 7.6, 1 mM EDTA, 50 mM NaCl). Phage titers were measured as colony-forming units (CFU) for the recombinant phagemid containing hGH-g3p gene III fusion (hGH-$g^3$) plasmid, and plaque-forming units (PFU) for the M13-K07 helper phage.

Binding selection using immobilized hGHbp

An aliquot of phage pool ϕ1 ($6\times10^9$ CFU, $6\times10^7$ PFU) was diluted 4.5-fold in buffer A (Phosphate-buffered saline, 0.5% BSA, 0.05% Tween-20, 0.01% thimerosal) and mixed with a 5 $\mu$L suspension of oxirane-polyacrylamide beads coupled to the hGHbp containing a Ser237 Cys mutation (350 fmols) in a 1.5 mL silated polypropylene tube. As a control, an equivalent aliquot of phage were mixed in a separate tube with beads that had been coated with BSA only. The phage were allowed to bind to the beads by incubating 3 hours at room temperature (23° C.) with slow rotation (approximately 7 RPM). Subsequent steps were carried out with a constant volume of 200 $\mu$L and at room temperature.

The beads were spun 15 sec., and the supernatant was removed (Sup. 1). To remove phage/phagemid not specifically bound, the beads were washed twice by resuspending in buffer A, then pelleting. A final wash consisted of rotating the beads in buffer A for 2 hours.

```
hGH  codon:                                 172        174
5'-    GC  TTC  AGG  AAG  GAC  ATG  GAC  NNS  GTC  NNS  ACA-

                         Ile
   176          178     179
-  NNS  CTG  NNS  ATC  GTG  CAG  TGC  CGC  TCT  GTG  G-3' (SEQ ID NO:12)
```

Phage/phagemid binding weakly to the beads were removed by stepwise elution with hGH. In the first step, the beads were rotated with buffer A containing 2 nM hGH. After 17 hours, the beads were pelleted and resuspended in buffer A containing 20 nM hGH and rotated for 3 hours, then pelleted. In the final hGH wash, the beads were suspended in buffer A containing 200 nM hGH and rotated for 3 hours then pelleted.

To remove the tightest-binding phagemid (i.e. those still bound after the hGH washes), beads were suspended in Glycine buffer (1M-Glycine, pH 2.0 with HCl), rotated 2 hours and pelleted. The supernatant (fraction "G"; 200 $\mu$L) was neutralized by adding 30 $\mu$L of 1M Tris base.

Fraction G eluted from the hGHbp-beads ($1\times10^6$ CFU, $5\times10^4$ PFU) was not substantially enriched for phagemid over K07 helper phage. This resulted from the fact that K07 phage packaged during propagation of the recombinant phagemid display the hGH-g3p fusion.

However, when compared with fraction G eluted from the BSA-coated control beads, the hGHbp-beads yielded 14 times as many CFU's. This reflects the enrichment of tight-binding hGH-displaying phagemid over nonspecifically-binding phagemid.

An aliquot ($4.3\times10^5$ CFU) of fraction G eluted from the hGHbp-beads was used to infect log-phase WJM101 cells. Transductions were carried out by mixing 100 $\mu$L fraction G with 1 mL WJM101 cells, incubating 20 min. at 37° C., then adding K07 (multiplicity of infection=1000). Cultures (25 mL 2 YT plus carbenicillin) were grown as described above and the second pool of phage (Library 1G, for first glycine elution) were prepared as described above.

Phage from library 1G (FIG. 3) were selected for binding to hGHbp beads as described above. Fraction G eluted from hGHbp beads contained 30 times as many CFU's as fraction G eluted from BSA-beads in this selection. Again, an aliquot of fraction G was propagated in WJM101 cells to yield library $1G^2$ (indicating that this library had been twice selected by glycine elution). Double-stranded DNA (pLIB $1G^2$) was also prepared from this culture.

KpnI assay and restriction-selection of Double Strand DNA

Figure 3:
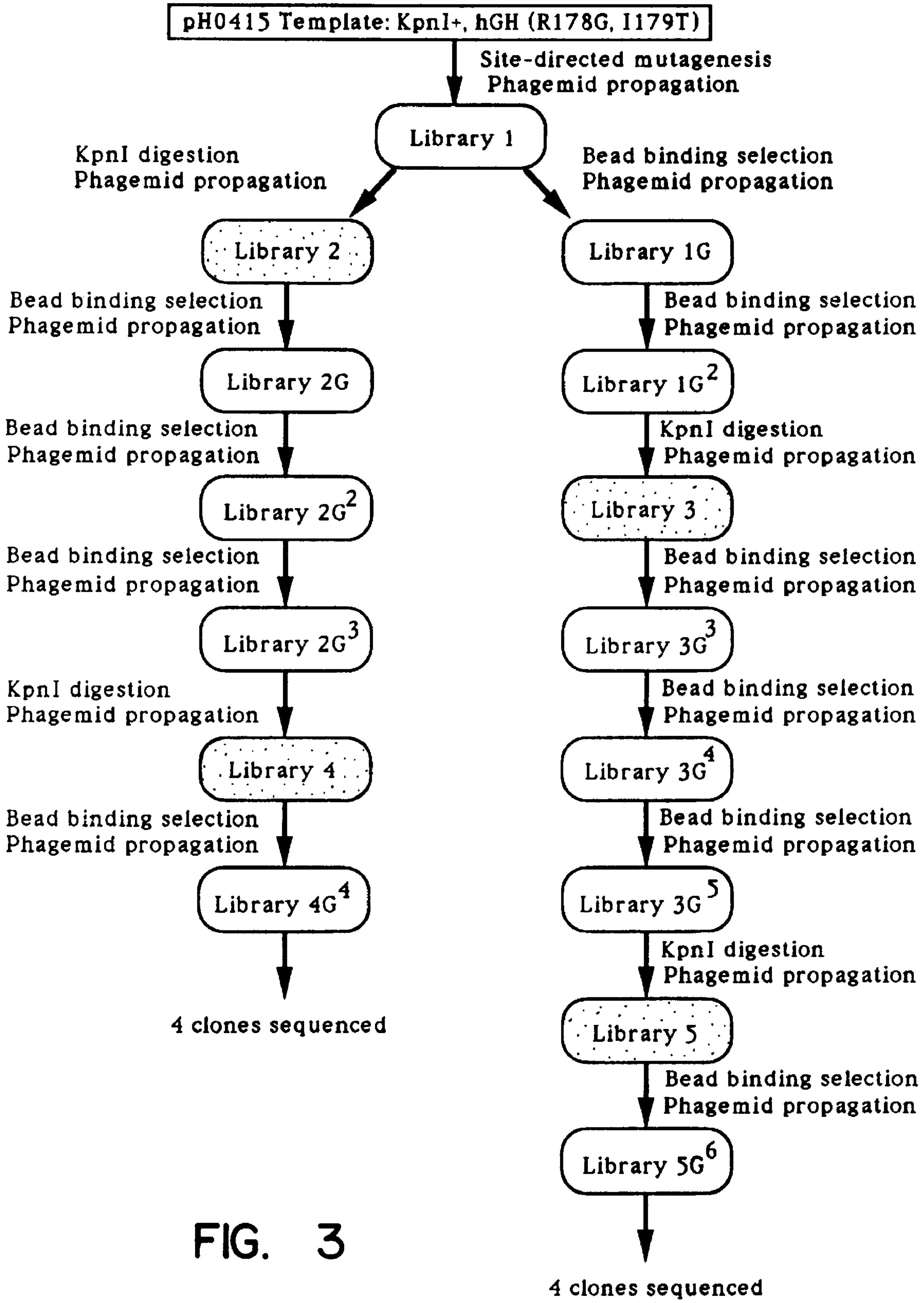
FIG. 3. Summary diagram of steps in the selection process for an hGH-phage library randomized at codons 172, 174, 176, and 178. The template molecules, pH0415, containing a unique KpnI restriction site and the hGH(R178G,I179T) gene was mutagenized as described in the text and electrotransformed into *E. coli* strain WJM101 to obtain the initial phagemid library, Library 1. An aliquot (approximately 2%) from Library 1 was used directly in an initial selection round as described in the text to yield Library 1G. Meanwhile, double-stranded DNA (dsDNA) was prepared from Library I, digested with restriction enzyme KpnI to eliminate template background, and electrotransformed into WJM101 to yield Library 2. Subsequent rounds of selection (or KpnI digestion, shaded boxes) followed by phagemid propagation were carried out as indicated by the arrows, according to the procedure described in the text. Four independent clones from Library $4G^4$ and four independent clones from Library $5G^6$ were sequenced by dideoxy sequencing. All of these clones had the identical DNA sequence, corresponding to the hGH mutant (Glu 174 Ser, Phe 176 Tyr).
Figure 4:
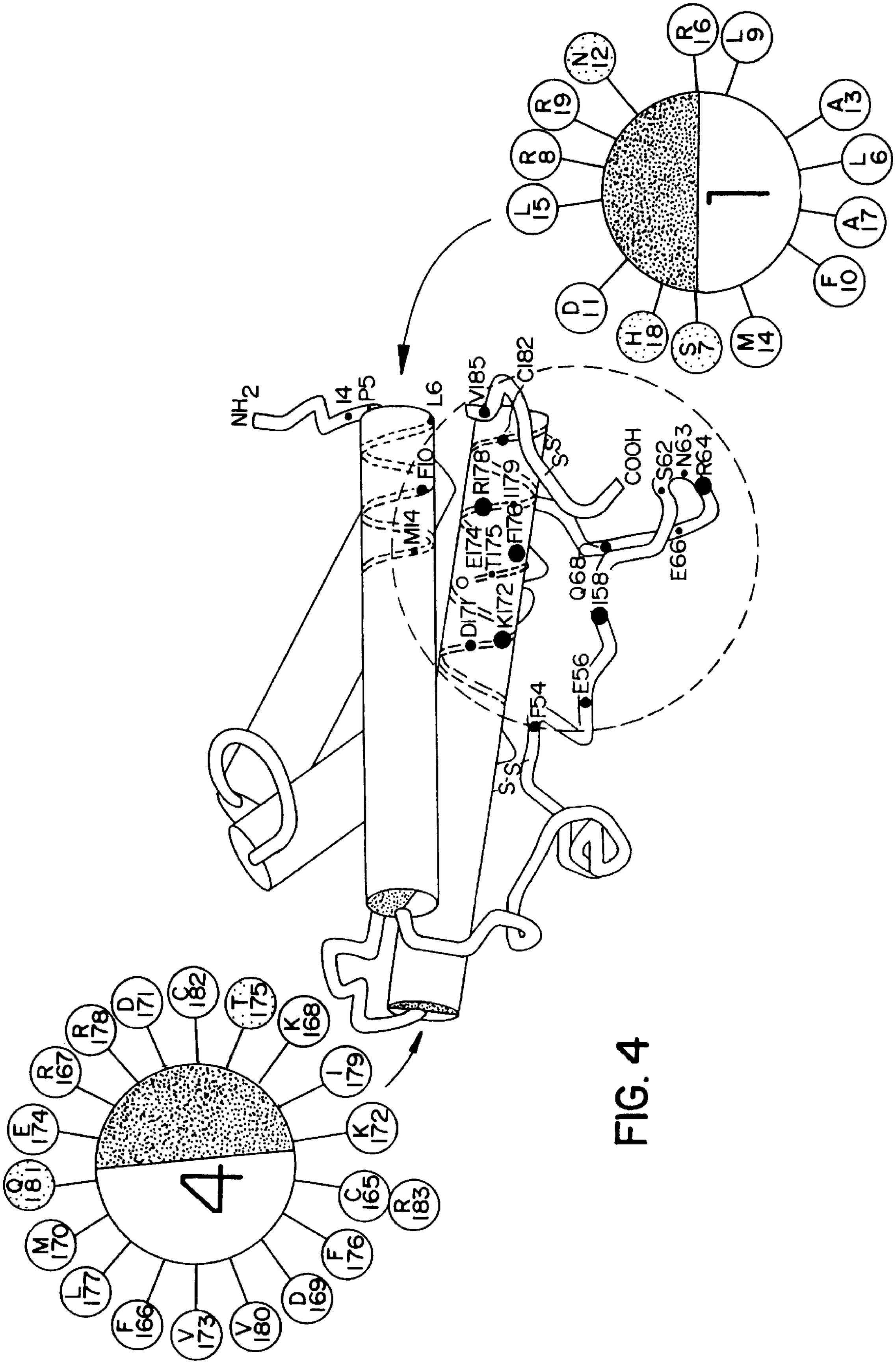
FIG. 4. Structural model of hGH derived from a 2.8 Å folding diagram of porcine growth hormone determined crystallographically. Location of residues in hGH that strongly modulate its binding to the hGH-binding protein are within the shaded circle. Alanine substitutions that cause a greater than tenfold reduction(I), a four- to tenfold reduction (I), or increase (I), or a two- to fourfold reduction (I), in binding affinity are indicated. Helical wheel projections in the regions of α-helix reveal their amphipathic quality. Blackened, shaded, or nonshaded residues are charged, polar, or nonpolar, respectively. In helix-4 the most important residues for mutation are on the hydrophilic face.
Figure 5:
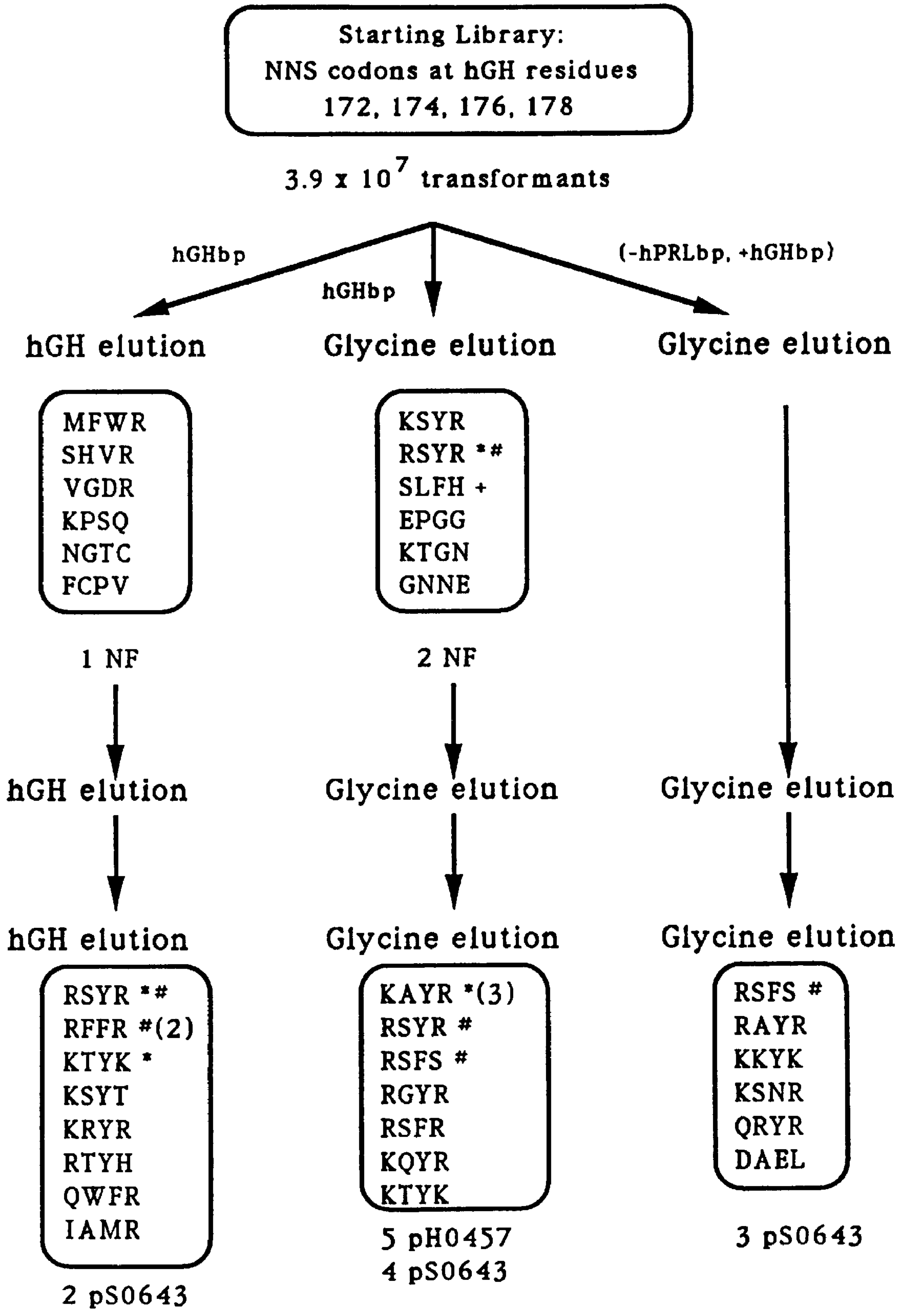
FIG. 5. Amino acid substitutions at positions 172, 174, 176 and 178 of hGH (The notation, e.g. KSYR, (SEQ ID NO:1) denotes hGH mutant 172K/174S/176Y/178R.) found after sequencing a number of clones from rounds 1 and 3 of the selection process for the pathways indicated (hGH elution; Glycine elution; or Glycine elution after preadsorption). Non-functional sequences (i.e. vector background, or other prematurely terminated and/or frameshifted mutants) are shown as "NF". Functional sequences which contained a non-silent, spurious mutation (i.e. outside the set of target residues) are marked with a "+". Protein sequences which appeared more than once among all the sequenced clones, but with different DNA sequences, are marked with a "#". Protein sequences which appeared more than once among the sequenced clones and with the same DNA sequence are marked with a "*". Note that after three rounds of selection, 2 different contaminating sequences were found; these clones did not correspond to cassette mutants, but to previously constructed hormone phage. The pS0643 contaminant corresponds to wild-type hGH-phage (hGH "KEFR" (SEQ ID NO:2)). The pH0457 contaminant, which dominates the third-round glycine-selected pool of phage, corresponds to a previously identified mutant of hGH, "KSYR." The amplification of these contaminants emphasizes the ability of the hormone-phage selection process to select for rarely occurring mutants. The convergence of sequences is also striking in all three pathways: R or K occurs most often at positions 172 and 178; Y or F occurs most often at position 176; and S, T, A, and other residues occur at position 174.
Figure 6:
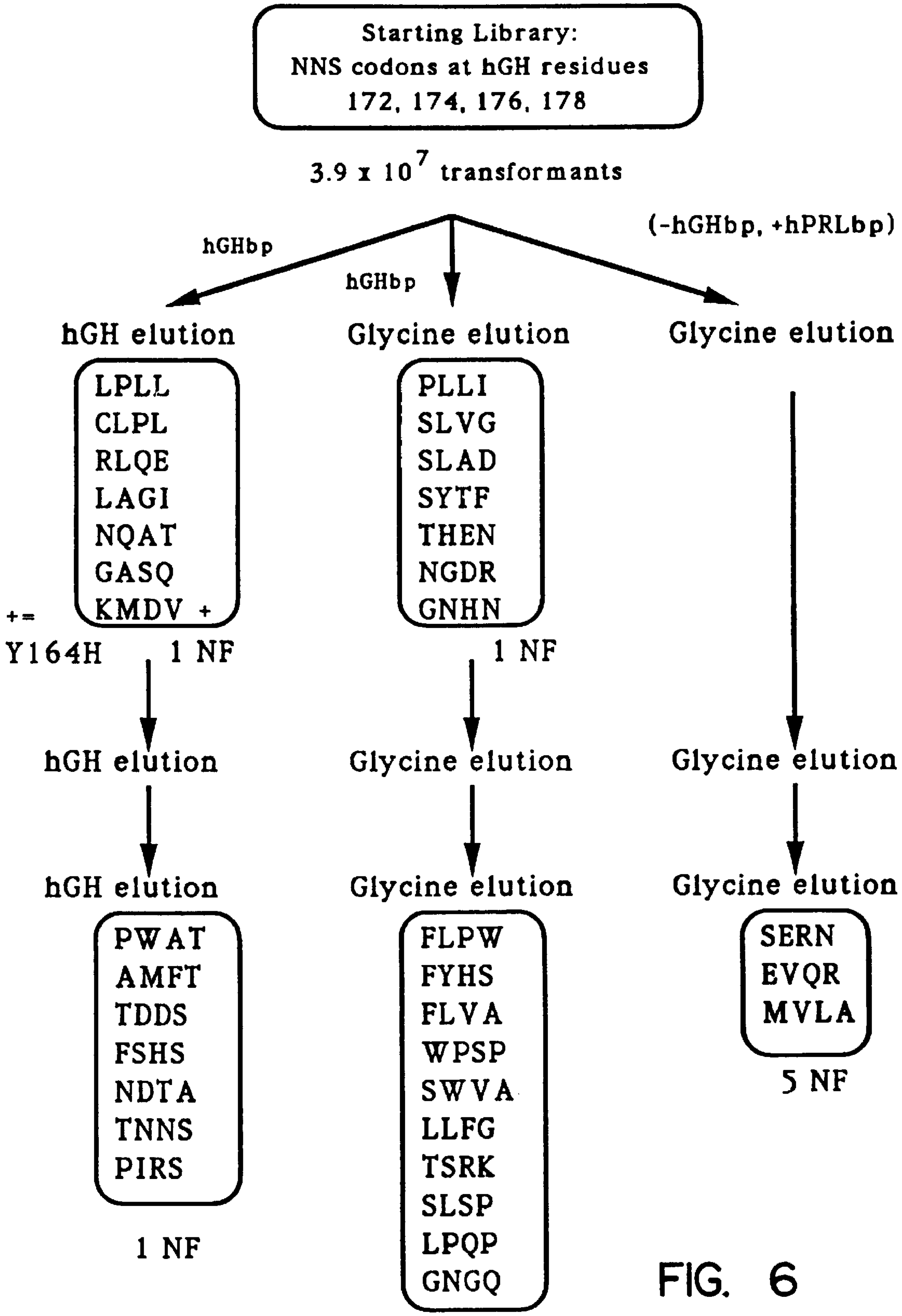
FIG. 6. Sequences from phage selected on hPRLbp-beads in the presence of zinc. The notation is as described in FIG. 5. Here, the convergence of sequences is not predictable, but there appears to be a bias towards hydrophobic sequences under the most stringent (Glycine) selection conditions; L, W and P residues are frequently found in this pool.
Figure 7:
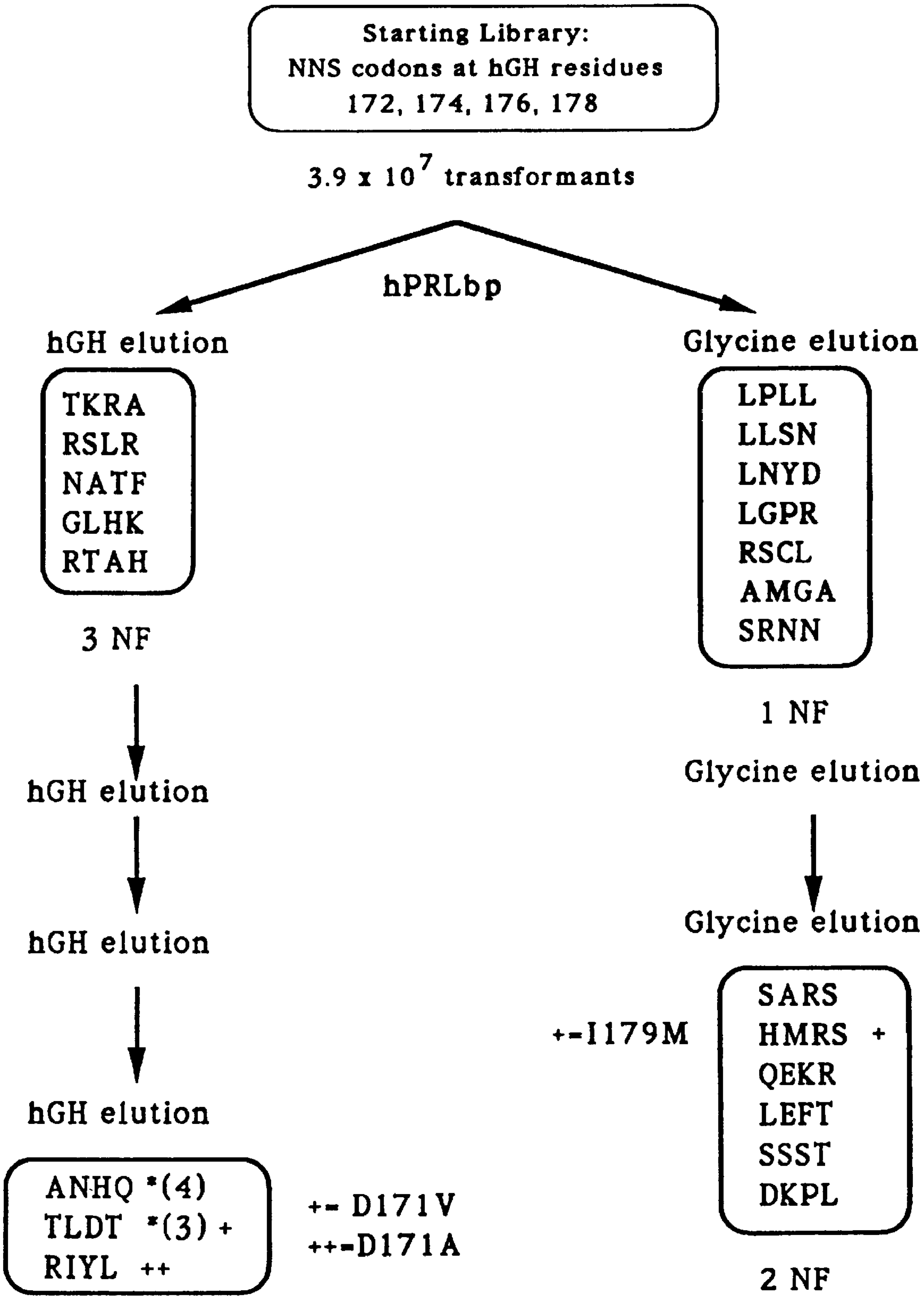
FIG. 7. Sequences from phage selected on hPRLbp-beads in the absence of zinc. The notation is as described in FIG. 5. In contrast to the sequences of FIG. 6, these sequences appear more hydrophilic. After 4 rounds of selection using hGH elution, two clones (ANHQ, (SEQ ID NO:3) and TLDT (SEQ ID NO:4)/171V) dominate the pool.
Figure 8:
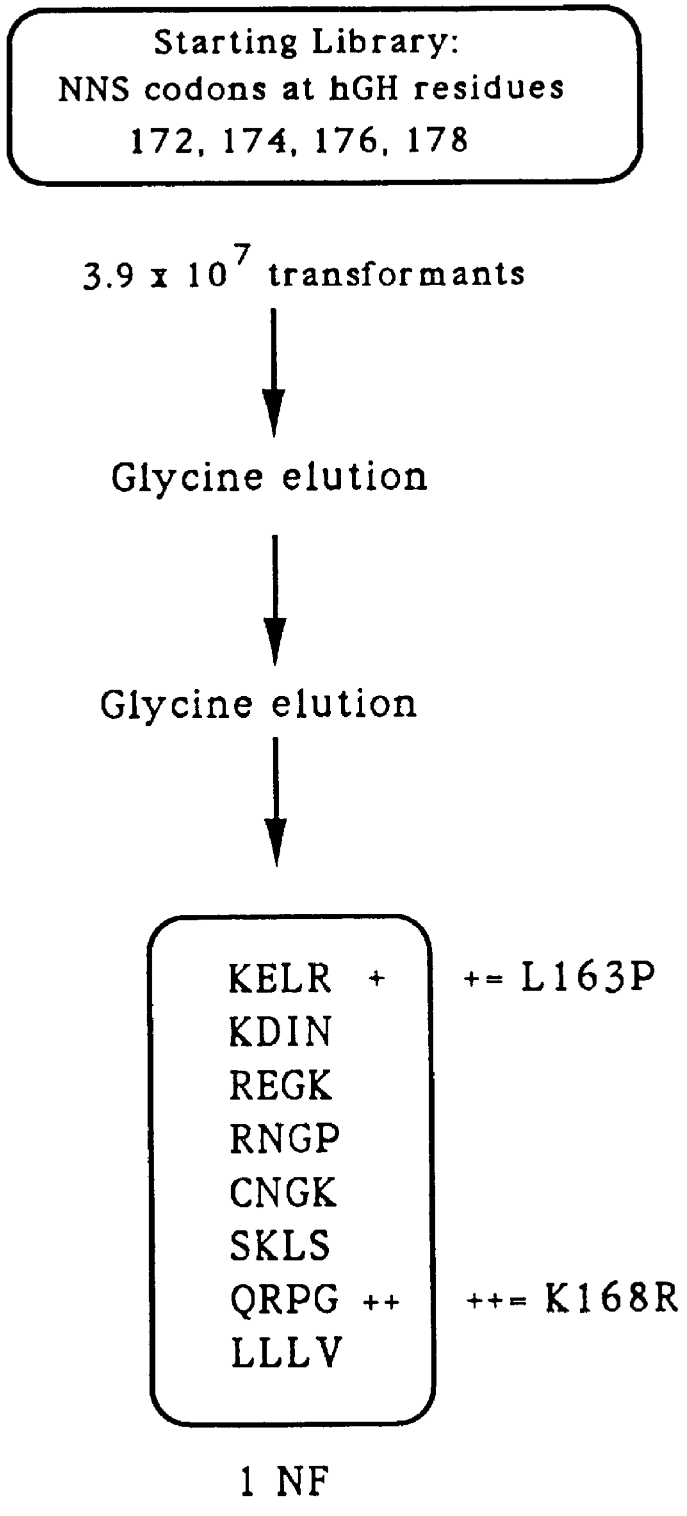
FIG. 8. Sequences from phage selected on blank beads. The notation is as described in FIG. 5. After three rounds of selection with glycine elution, no siblings were observed and a background level of non-functional sequences remained.

To reduce the level of background ($KpnI^+$) template, an aliquot (about 0.5 $\mu$g) of pLIB $1G^2$ was digested with KpnI and electroporated into WJM101 cells. These cells were grown in the presence of K07 (multiplicity of infection=100) as described for the initial library, and a new phage pool, pLIB 3, was prepared (FIG. 3).

In addition, an aliquot (about 0.5 $\mu$g) of dsDNA from the initial library (pLIB1) was digested with KpnI and electroporated directly into WJM101 cells. Transformants were allowed to recover as above, infected with M13-K07, and grown overnight to obtain a new library of phage, designated phage Library 2 (FIG. 3).

Successive rounds of selection

Phagemid binding, elution, and propagation were carried out in successive rounds for phagemid derived from both pLIB 2 and pLIB 3 (FIG. 3) as described above, except that (1) an excess (10-fold over CFU) of purified K07 phage (not displaying hGH) was added in the bead-binding cocktail, and (2) the hGH stepwise elutions were replaced with brief washings of buffer A alone. Also, in some cases, XL1-Blue cells were used for phagemid propagation.

An additional digestion of dsDNA with KpnI was carried out on pLIB $2G^3$ and on pLIB 3G5 before the final round of bead-binding selection (FIG. 3).

DNA Sequencing of selected phagemids

Four independently isolated clones from LIB $4G^4$ and four independently isolated clones from LIB $5G^6$ were sequenced by dideoxy sequencing. All eight of these clones had identical DNA sequences:

```
hGH codon:  172          174          176          178
     5'-AAG  GTC  TCC  ACA  TAC  CTG  AGG  ATC-3'
                                        (SEQ ID NO:13)
```

Thus, all these encode the same mutant of hGH: (E174S, F176Y). Residue 172 in these clones is Lys as in wild-type. The codon selected for 172 is also identical to wild-type hGH. This is not surprising since AAG is the only lysine-codon possible from a degenerate "NNS" codon set. Residue 178-Arg is also the same as wild-type, but here, the codon selected from the library was AAG instead of CGC as is found in wild-type hGH, even though the latter codon is also possible using the "NNS" codon set.

Multiplicity of K07 infection

The multiplicity of infection of K07 infection is an important parameter in the propagation of recombinant phagemids. The K07 multiplicity of infection must be high enough to insure that virtually all cells transformed or transfected with phagemid are able to package new phagemid particles. Furthermore, the concentration of wild-type gene III in each cell should be kept high to reduce the possibility of multiple hGH-gene III fusion molecules being displayed on each phagemid particle, thereby reducing chelate effects in binding. However, if the K07 multiplicity of infection is too high, the packaging of K07 will compete with that of recombinant phagemid. We find that acceptable phagemid yields, with only 1–10% background K07 phage, are obtained when the K07 multiplicity of infection is about 100.

TABLE IV

| Phage Pool | moi (K07) | Enrichment CFU/PFU | hGHbp/BSA beads | Fraction KpnI |
|---|---|---|---|---|
| LIB 1 | 1000 | ND | 14 | 0.44 |
| LIB 1G | 1000 | ND | 30 | 0.57 |
| LIB 3 | 100 | ND | 1.7 | 0.26 |
| LIB $3G^3$ | 10 | ND | 8.5 | 0.18 |
| LIB $3G^4$ | 100 | 460 | 220 | 0.13 |
| LIB 5 | 100 | ND | 15 | ND |
| LIB 2 | 100 | ND | 1.7 | <0.05 |
| LIB 2G | 10 | ND | 4.1 | <0.10 |
| LIB $2G^2$ | 100 | 1000 | 27 | 0.18 |
| LIB 4 | 100 | 170 | 38 | ND |

Phage pools are labelled as shown (FIG. 3). The multiplicity of infection (moi) refers to the multiplicity of K07 infection (PFU/cells) in the propagation of phagemid. The enrichment of CFU over PFU is shown in those cases where purified K07 was added in the binding step. The ratio of CFU eluting from hGHbp-beads over CFU eluting from BSA-beads is shown. The fraction of KpnI-containing template (i.e., pH0415) remaining in the pool was determined by digesting dsDNA with KpnI plus EcoRI, running the products on a 1% agarose gel, and laser-scanning a negative of the ethidium bromide-stained DNA.

Receptor-binding affinity of the hormone hGH(E174S, F176Y)

The fact that a single done was isolated from two different pathways of selection (FIG. 3) suggested that the double mutant (E174S,F176Y) binds strongly to hGHbp. To determine the affinity of this mutant of hGH for hGHbp, this mutant of hGH was constructed using site-directed mutagenesis, using a plasmid (pB0720) which contains the wild-type hGH gene as template and the following oligonucleotide which changes codons 174 and 176:

| hGH codon: | | | 172 | | 174 | | 176 | | 178 | | | |
|---|---|---|---|---|---|---|---|---|---|---|---|---|
| | | | Lys | | Ser | | Tyr | | Arg | | | |
| 5'- | ATG | GAC | AAG | GTG | TCG | ACA | TAC | CTG | CGC | ATC | GTG | -3' (SEQ ID NO:14) |

The resulting construct, pH0458B, was transformed into *E. coli* strain 16C9 for expression of the mutant hormone. Scatchard analysis of competitive binding of hGH(E174S, F176Y) versus $^{125}$I-hGH to hGHbp indicated that the (E174S,F176Y) mutant has a binding affinity at least 5.0-fold tighter than that of wild-type hGH.

Example VIII

Figure 9:
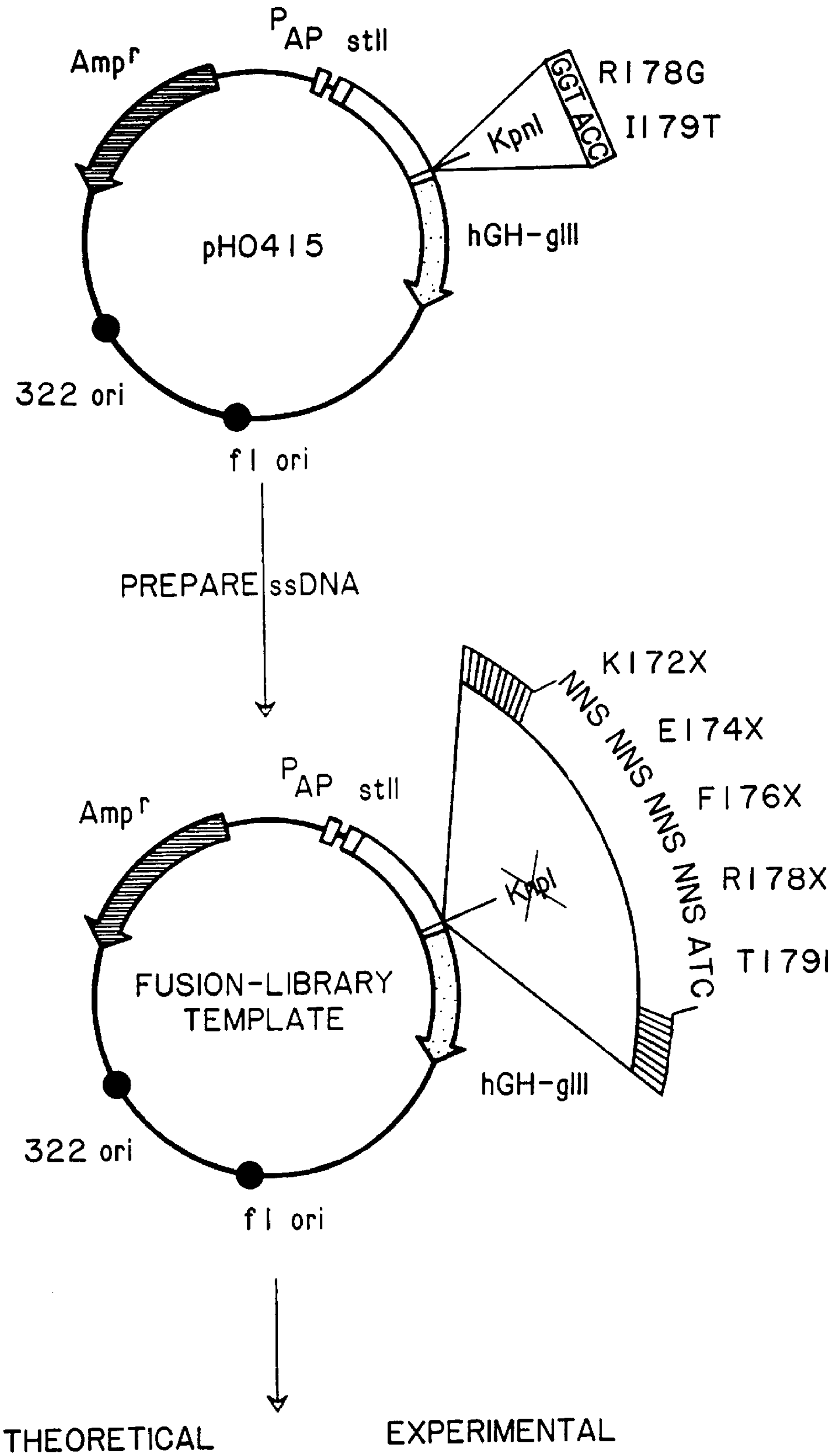
FIG. 9. Construction of phagemid fl ori from pHO415. This vector for cassette mutagenesis and expression of the hGH-gene III fusion protein was constructed as follows. Plasmid pS0643 was constructed by oligonucleotide-directed mutagenesis of pS0132, which contains pBR322 and f1 origins of replication and expresses an hGH-gene III fusion protein (hGH residues 1–191, followed by a single Gly residue, fused to Pro-198 of gene III) under the control of the *E. coli* phoA promoter. Mutagenesis was carried out with the oligonucleotide 5'-GGC-AGC-TGT-GGC-TTC-TAG-AGT-GGC-GGC-GGC-TCT-GGT-3', (SEQ ID NO:5) which introduced a XbaI site (underlined) and an amber stop codon (TAG) following Phe-191 of hGH.
Figure 10A:
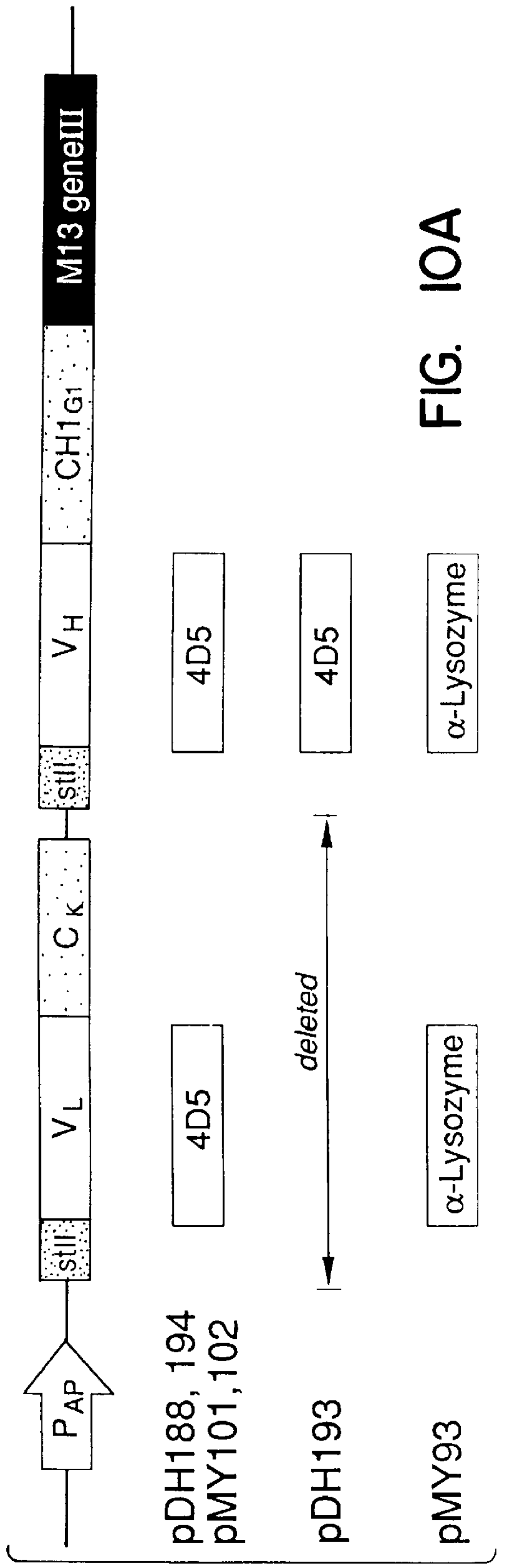
FIGS. 10A and 10B. A. Diagram of plasmid pDH188 insert containing the DNA encoding the light chain and heavy chain (variable and constant domain 1) of the $F_{ab}$ humanized antibody directed to the HER-2 receptor. $V_L$ and $V_H$ are the variable regions for the light and heavy chains, respectively. $C_k$ is the constant region of the human kappa light chain. $CH1_{G1}$ is the first constant region of the human gamma 1 chain. Both coding regions start with the bacterial st II signal sequence.
Figure 10B:
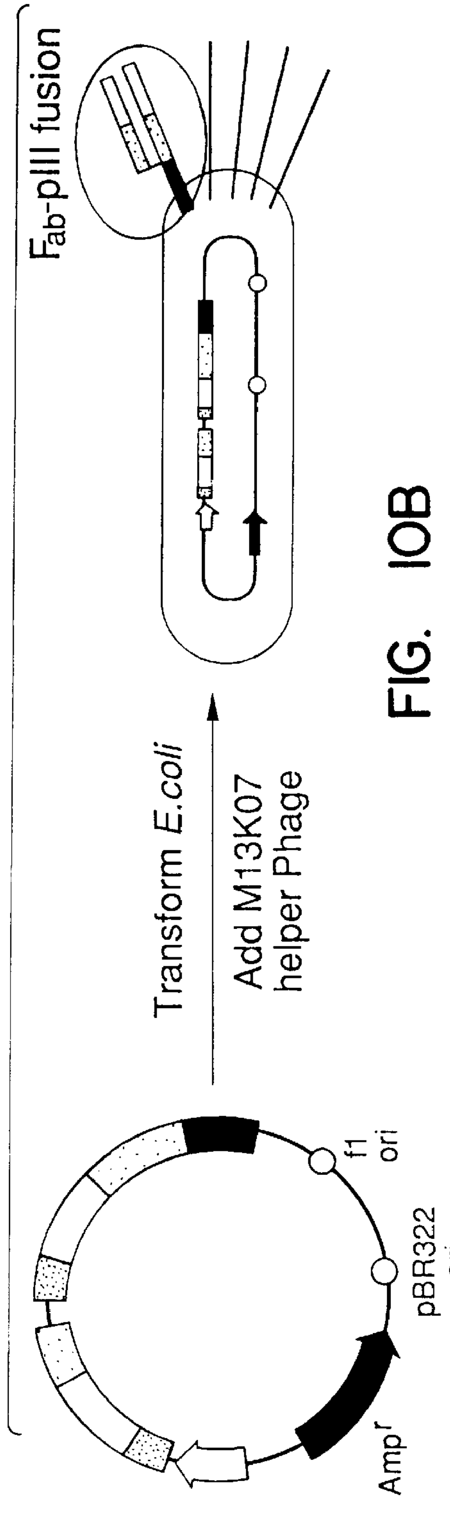
Figure 12:
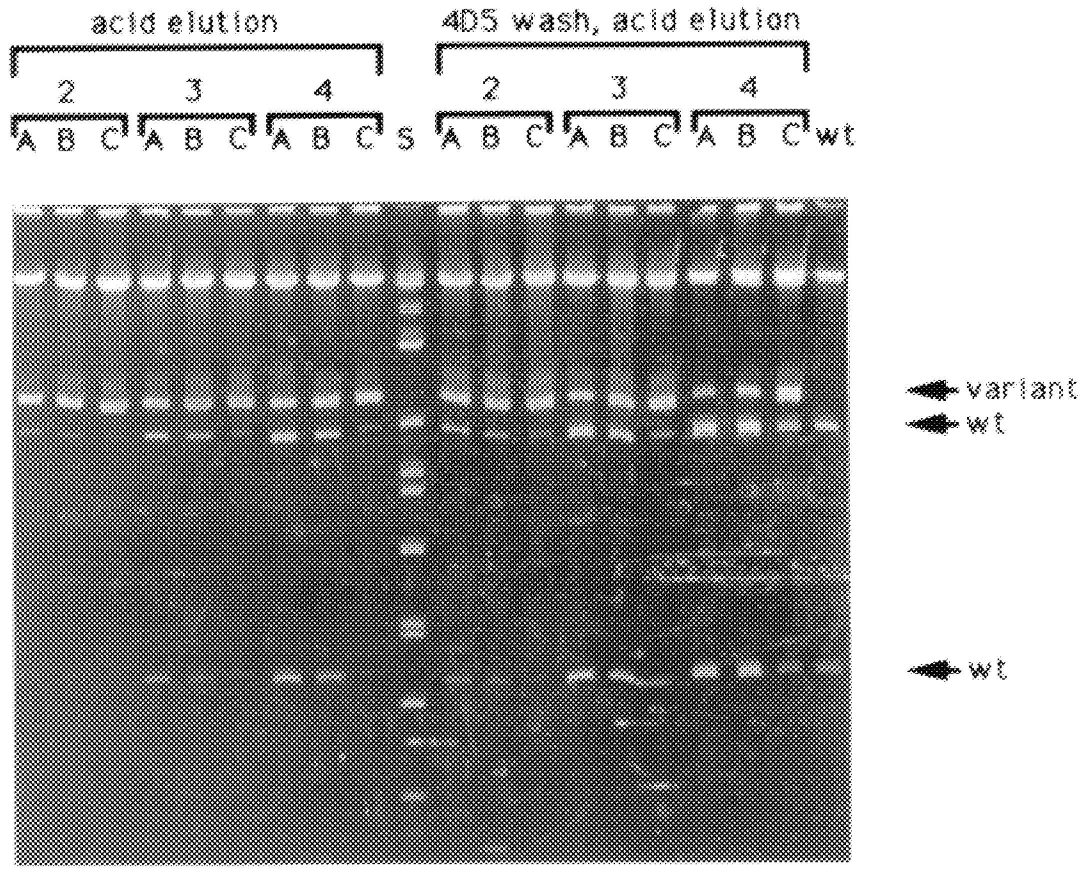
FIG. 12. Enrichment of wild-type 4D5 $F_{ab}$ phagemid from variant $F_{ab}$ phagemid. Mixtures of wild-type phagemid and variant 4D5 $F_{ab}$ phagemid in a ratio of 1:1,000 were selected on plates coated with the extra-cellular domain protein of the HER-2 receptor. After each round of selection, a portion of the eluted phagemid were infected into *E. coli* and plasmid DNA was prepared. This plasmid DNA was then digested with Eco RV and Pst I, separated on a 5% polyacrylamide gel, and stained with ethidium bromide. The bands were visualized under UV light. The bands due to the wild-type and variant plasmids are marked with arrows. The first round of selection was eluted only under acid conditions; subsequent rounds were eluted with either an acid elution (left side of Figure) or with a humanized 4D5 antibody wash step prior to acid elution (right side of Figure) using methods described in Example VIII. Three variant 4D5 $F_{ab}$ molecules were made: H91A (amino acid histidine at position 91 on the $V_L$ chain mutated to alanine; indicated as 'A' lanes in Figure), Y49A (amino acid tyrosine at position 49 on the $V_L$ chain mutated to alanine; indicated as 'B' lanes in the Figure), and Y92A (amino acid tyrosine at position 92 on the $V_L$ chain mutated to alanine; indicated as 'C' lanes in the Figure). Amino acid position numbering is according to Kabat et al., (*Sequences of proteins of immunological interest,* 4th ed., U.S. Dept of Health and Human Services, Public Health Service, Nat'l. Institute of Health, Bethesda, Md. (1987)).

Selection of hGH Variants from a Helix-4 Random Cassette Library of Hormone-Phage Human growth hormone variants were produced by the method of the present invention using the phagemid described in FIG. 9.

Construction of a de-fusable hormone-phage vector

A vector useful for cassette mutagenesis was designed (Wells et al., *Gene* 34, 315–323 (1985)) and expression of the hGH-gene III fusion protein with the objectives of: (1) improving the linkage between hGH and the gene III moiety to more favorably display the hGH moiety on the phage; (2) limiting expression of the fusion protein to obtain essentially "monovalent display,"; (3) allowing for restriction nuclease selection against the starting vector; (4) eliminating expression of fusion protein from the starting vector; and (5) achieving facile expression of the corresponding free hormone from a given hGH-gene III fusion mutant.

Plasmid pS0643 was constructed by oligonucleotide-directed mutagenesis (Kunkel et al., *Methods Enzymol,* 154, 367–382 (1987)) of pS0132, which contains pBR322 and f1 origins of replication and expresses an hGH-gene III fusion protein (hGH residues 1–191, followed by a single Gly residue, fused to Pro-198 of gene III) under the control of the *E. coli* phoA promoter (Bass et al., *Proteins* 8, 309–314 (1990))(FIG. 9). Mutagenesis was carried out with the oligonucleotide 5'-GGC-AGC-TGT-GGC-TTC-TAG-AGT-GGC-GGC-GGC-TCT-GGT-3', (SEQ ID NO:15) which introduces a XbaI site (underlined) and an amber stop codon (TAG) following Phe-191 of hGH. In the resulting construct, pS0643, a portion of gene III was deleted, and two silent mutations (underlined) occurred, yielding the following junction between hGH and gene III:

| — hGH → | | | | | | gene III → | | | | | | |
|---|---|---|---|---|---|---|---|---|---|---|---|---|
| 187 | 188 | 189 | 190 | 191 | am* | 249 | 250 | 251 | 252 | 253 | 254 | |
| Gly | Ser | Cys | Gly | Phe | Glu | Ser | Gly | Gly | Gly | Ser | Gly | (SEQ ID NO:16) |
| GGC | AGC | TGT | GGA | TTC | TAG | AGT | GGC | GGT | GGC | TCT | GGT | (SEQ ID NO:17) |

This shortens the total size of the fusion protein from 401 residues in pS0132 to 350 residues in pS0643. Experiments using monoclonal antibodies against hGH have demonstrated that the hGH portion of the new fusion protein, assembled on a phage particle, is more accessible than was the previous, longer fusion.

For propagation of hormone-displaying phage, pS0643 and derivatives can be grown in a amber-suppressor strain of *E. coli* such as JM101 or XL1-Blue (Bullock et al., *Bio-Techniques* 5, 376–379 (1987)). Shown above is substitution of Glu at the amber codon which occurs in supE suppressor strains. Suppression with other amino acids is also possible in various available strains of *E. coli* well known and publicly available.

To express hGH (or mutants) free of the gene III portion of the fusion, pS0643 and derivatives can simply be grown in a non-suppressor strain such as 16C9. In this case, the amber codon (TAG) leads to termination of translation, which yields free hormone, without the need for an independent DNA construction.

To create sites for cassette mutagenesis, pS0643 was mutated with the oligonucleotides (1) 5'-CGG-ACT-GGG-CAG-ATA-TTC-AAG-CAG-ACC-3', (SEQ ID NO:18) which destroys the unique BglII site of pS0643; (2) 5'-CTC-AAG-AAC-TAC-GGG-TTA-CCC-TGA-CTG-CTT-CAG-GAA-GG-3', (SEQ ID NO: 19) which inserts a unique BstEII site, a single-base frameshift, and a non-amber stop codon (TGA); and (3) 5'-CGC-ATC-GTG-CAG-TGC-AGA-TCT-GTG-GAG-GGC-3', (SEQ ID NO: 20) which introduces a new BglII site, to yield the starting vector, pH0509. The addition of a frameshift along with a TGA stop codon insures that no geneIII-fusion can be produced from the starting vector. The BstEII-BglII segment is cut out of pH0509 and replaced with a DNA cassette, mutated at the codons of interest. Other restriction sites for cassette mutagenesis at other locations in hGH have also been introduced into the hormone-phage vector.

Cassette mutagenesis within helix 4 of hGH

Codons 172, 174, 176 and 178 of hGH were targeted for random mutagenesis because they all lie on or near the surface of hGH and contribute significantly to receptor-binding (Cunningham and Wells, *Science* 244, 1081–1085 (1989)); they all lie within a well-defined structure, occupying 2 "turns" on the same side of helix 4; and they are each substituted by at least one amino acid among known evolutionary variants of hGH.

At each of the target residues, NNS (N=A/G/C/T; S=G/C) was substituted. The choice of the NNS degenerate sequence yields 32 possible codons (including at least one codon for each amino acid) at 4 sites, for a total of $(32)^4$=1,048,576 possible nucleotide sequences, or $(20)^4$=160,000 possible polypeptide sequences. Only one stop codon, amber (TAG), is allowed by this choice of codons, and this codon is suppressible as Glu in supE strains of *E. coli.*

Two degenerate oligonucleotides, with NNS at codons 172, 174, 176, and 178, were synthesized, phosphorylated, and annealed to construct the mutagenic cassette: 5'-GT-TAC-TCT-ACT-GCT-TTC-AGG-AAG-GAC-ATG-GAC-NNS-GTC-NNS-ACA-NNS-CTG-NNS-ATC-GTG-CAG-TGC-A-3', (SEQ ID NO: 21) and 5'-GA-TCT-GCA-CTG- CAC-GAT-SNN-CAG-SNN-TGT-SNN-GAC-SNN-GTC-CAT-GTC-CTT-CCT-GAA-GCA-GTA-GA-3' (SEQ ID NO:22).

The vector was prepared by digesting pH0509 with BstEII followed by BglII. The products were run on a 1% agarose gel and the large fragment excised, phenol-extracted, and ethanol precipitated. This fragment was treated with calf intestinal phosphatase (Boehringer), then phenol:chloroform extracted, ethanol precipitated, and resuspended for ligation with the mutagenic cassette.

Propagation of the initial library in XL1-Blue cells

Following ligation, the reaction products were again digested with BstEII, then phenol:chloroform extracted, ethanol precipitated and resuspended in water. (A BstEII recognition site (GGTNACC) (SEQ ID NO:23) is created within cassettes which contain a G at position 3 of codon 172 and an ACC (Thr) codon at 174. However, treatment with BstEII at this step should not select against any of the possible mutagenic cassettes, because virtually all cassettes will be heteroduplexes, which cannot be cleaved by the enzyme.) Approximately 150 ng (45 fmols) of DNA was electroporated into XL1-Blue cells ($1.8\times10^9$ cells in 0.045 mL) in a 0.2 cm cuvette at a voltage setting of 2.49 kV with a single pulse (time constant=4.7 msec.).

The cells were allowed to recover 1 hour at 37° C. in S.O.C media with shaking, then mixed with 25 mL 2 YT medium, 100 mg/mL carbenicillin, and M13-K07 (moi=100). After 10' at 23° C., the culture was incubated overnight (15 hours) at 37° C. with shaking. Plating of serial dilutions from this culture onto carbenicillin-containing media indicated that $3.9\times10^7$ electrotransformants were obtained.

After overnight incubation, the cells were pelleted, and double-stranded DNA (dsDNA), designated pH0529E (the initial library), was prepared by the alkaline lysis method. The supernatant was spun again to remove any remaining cells, and the phage, designated phage pool ϕH0529E (the initial library of phage), were PEG-precipitated and resuspended in 1 mL STE buffer (10 mM Tris, pH 7.6, 1 mM EDTA, 50 mM NaCl). Phage titers were measured as colony-forming units (CFU) for the recombinant phagemid containing hGH-g3p. Approximately $4.5\times10^{13}$ CFU were obtained from the starting library.

Degeneracy of the starting library

From the pool of electrotransformants, 58 clones were sequenced in the region of the BstEII-BglII cassette. Of these, 17% corresponded to the starting vector, 17% contained at least one frame shift, and 7% contained a non-silent (non-terminating) mutation outside the four target codons. About 41% of the clones were defective by one of the above measures, leaving a total functional pool of $2.0\times10^7$ initial transformants. This number still exceeds the possible number of DNA sequences by nearly 20-fold. Therefore, it appears that all possible sequences are represented in the starting library.

The sequences of non-selected phage were examined to evaluate the degree of codon bias in the mutagenesis (Table V). The results indicated that, although some codons (and amino acids) are under- or over-represented relative to the random expectation, the library is extremely diverse, with no evidence of large-scale "sibling" degeneracy (Table VI).

TABLE V

Codon distribution (per 188 codons) of non-selected hormone phage. Clones were sequenced from the starting library (pH0529E). All codons were tabulated, including those from clones which contained spurious mutations and/or frameshifts. *Note: the amber stop codon (TAG) is suppressed as Glu in XLI-Blue cells. Highlighted codons were over/under-represented by 50% or more.

| Residue | Number expected | Number found | Found/Expected |
|---|---|---|---|
| Leu | 17.6 | 18 | 1.0 |
| Ser | 17.6 | 26 | 1.5 |
| Arg | 17.6 | 10 | 0.57 |
| Pro | 11.8 | 16 | 1.4 |
| Thr | 11.8 | 14 | 1.2 |
| Ala | 11.8 | 13 | 1.1 |
| Gly | 11.8 | 16 | 1.4 |
| Val | 11.8 | 4 | 0.3 |
| Ile | 5.9 | 2 | 0.3 |
| Met | 5.9 | 1 | 0.2 |
| Tyr | 5.9 | 1 | 0.2 |
| His | 5.9 | 2 | 0.3 |
| Trp | 5.9 | 2 | 0.3 |
| Phe | 5.9 | 5 | 0.9 |
| Cys | 5.9 | 5 | 0.9 |
| Gln | 5.9 | 7 | 1.2 |
| Asn | 5.9 | 14 | 2.4 |
| Lys | 5.9 | 11 | 1.9 |
| Asp | 5.9 | 9 | 1.5 |
| Glu | 5.9 | 6 | 1.0 |
| amber* | 5.9 | 6 | 1.0 |

TABLE VI

Non-selected (pH0529E) clones with an open reading frame. The notation, e.g. TWGS, denotes the hGH mutant 172T/174W/176G/178S. Amber (TAG) codons, translated as Glu in XL1-Blue cells are shown as ϵ.

| | | |
|---|---|---|
| KϵNT (SEQ ID NO: 24) | KTEQ (SEQ ID NO:37) | CVLQ (SEQ ID NO:50) |
| TWGS (SEQ ID NO:25) | NNCR (SEQ ID NO:38) | EASL (SEQ ID NO:51) |
| PϵER (SEQ ID NO:26) | FPCL (SEQ ID NO:39) | SSKE (SEQ ID NO:52) |
| LPPS (SEQ ID NO:27) | NSDF (SEQ ID NO:40) | ALLL (SEQ ID NO:53) |
| SLDP (SEQ ID NO:28) | HRPS (SEQ ID NO:41) | PSHP (SEQ ID NO:54) |
| QQSN (SEQ ID NO:29) | LSLϵ (SEQ ID NO:42) | SYAP (SEQ ID NO:55) |
| GSKT (SEQ ID NO:30) | NGSK (SEQ ID NO:43) | ASNG (SEQ ID NO:56) |
| TPVT (SEQ ID NO:31) | LTTE (SEQ ID NO:44) | EANN (SEQ ID NO:57) |
| RSRA (SEQ ID NO:32) | PSGG (SEQ ID NO:45) | KNAK (SEQ ID NO:58) |
| LCGL (SEQ ID NO:33) | LWFP (SEQ ID NO:46) | SRGK (SEQ ID NO:59) |
| TGRL (SEQ ID NO:34) | PAGS (SEQ ID NO:47) | GLDG (SEQ ID NO:60) |
| AKAS (SEQ ID NO:35) | GRAK (SEQ ID NO:48) | NDPI (SEQ ID NO:61) |
| GNDD (SEQ ID NO:36) | GTNG (SEQ ID NO:49) | |

Preparation of immobilized hGHbp and hPRLbp

Immobilized hGHbp ("hGHbp-beads") was prepared as described (Bass et al., *Proteins* 8, 309–314 (1990)), except that wild-type hGHbp (Fuh et al., *J. Biol. Chem.* 265, 3111–3115 (1990)) was used. Competitive binding experiments with ($^{125}$I) hGH indicated that 58 fmols of functional hGHbp were coupled per μL of bead suspension.

Immobilized hPRLbp ("hPRLbp-beads") was prepared as above, using the 211-residue extracellular domain of the prolactin receptor (Cunningham et al., *Science* 250, 1709–1712 (1990)). Competitive binding experiments with ($^{125}$I) hGH in the presence of 50 μM zinc indicated that 2.1 fmols of functional hPRLbp were coupled per μL of bead suspension.

"Blank beads" were prepared by treating the oxirane-acrylamide beads with 0.6M ethanolamine (pH 9.2) for 15 hours at 4° C.

Binding selection using immobilized hGHbp and hPRLbp

Binding of hormone-phage to beads was carried out in one of the following buffers: Buffer A (PBS, 0.5% BSA, 0.05% Tween 20, 0.01% thimerosal) for selections using hGHbp and blank beads; Buffer B (50 mM tris pH 7.5, 10 mM $MgCl_2$, 0.5% BSA, 0.05% Tween 20, 100 mM $ZnCl_2$) for selections using hPRLbp in the presence of zinc (+$Zn^{2+}$); or Buffer C (PBS, 0.5% BSA, 0.05% Tween 20, 0.01% thimerosal, 10 mM EDTA) for selections using hPRLbp in the absence of zinc (+EDTA). Binding selections were carried out according to each of the following paths: (1) binding to blank beads, (2) binding to hGHbp-beads, (3) binding to hPRLbp-beads (+$Zn^{2+}$), (4) binding to hPRLbp-beads (+EDTA), (5) pre-adsorbing twice with hGHbp beads then binding the non-adsorbed fraction to hPRLbp-beads ("−hGHbp, +hPRLbp" selection), or (6) pre-adsorbing twice with hPRLbp-beads then binding the non-adsorbed fraction to hGHbp-beads ("−hPRLbp, +hGHbp" selection). The latter two procedures are expected to enrich for mutants binding hPRLbp but not hGHbp, or for mutants binding hGHbp but not hPRLbp, respectively. Binding and elution of phage was carried out in each cycle as follows:

An aliquot of hormone phage (typically $10^9$–$10^{10}$ CFU) was mixed with an equal amount of non-hormone phage (pCAT), diluted into the appropriate buffer (A, B, or C), and mixed with a 10 mL suspension of hGHbp, hPRLbp or blank beads in a total volume of 200 mL in a 1.5 mL polypropylene tube. The phage were allowed to bind to the beads by incubating 1 hour at room temperature (23° C.) with slow rotation (approximately 7 RPM). Subsequent steps were carried out with a constant volume of 200 $\mu$L and at room temperature.

The beads were spun 15 sec., and the supernatant was removed. To reduce the number of phage not specifically bound, the beads were washed 5 times by resuspending briefly in the appropriate buffer, then pelleting.

Phage binding weakly to the beads were removed by elution with hGH. The beads were rotated with the appropriate buffer containing 400 nM hGH for 15–17 hours. The supernatant was saved as the "hGH elution" and the beads. The beads were washed by resuspending briefly in buffer and pelleting.

To remove the tightest-binding phage (i.e. those still bound after the hGH wash), beads were suspended in Glycine buffer (Buffer A plus 0.2M Glycine, pH 2.0 with HCl), rotated 1 hour and pelleted. The supernatant ("Glycine elution"; 200 $\mu$L) was neutralized by adding 30 mL of 1M Tris base and stored at 4° C.

Aliquots from the hGH elutions and from the Glycine elutions from each set of beads under each set of conditions were used to infect separate cultures of log-phase XL1-Blue cells. Transductions were carried out by mixing phage with 1 mL XL1-Blue cells, incubating 20 min. at 37° C., then adding K07 (moi=100). Cultures (25 mL 2 YT plus carbenicillin) were grown as described above and the next pool of phage was prepared as described above.

Phage binding, elution, and propagation were carried out in successive rounds, according to the cycle described above. For example, the phage amplified from the hGH elution from hGHbp-beads were again selected on hGHbp-beads and eluted with hGH, then used to infect a new culture of XL1-Blue cells. Three to five rounds of selection and propagation were carried out for each of the selection procedures described above.

DNA Sequencing of selected phagemids

From the hGH and Glycine elution steps of each cycle, an aliquot of phage was used to inoculate XL1-Blue cells, which were plated on LB media containing carbenicillin and tetracycline to obtain independent clones from each phage pool. Single-stranded DNA was prepared from isolated colony and sequenced in the region of the mutagenic cassette. The results of DNA sequencing are summarized in terms of the deduced amino acid sequences in FIGS. 5, 6, 7, and 8.

Expression and assay of hGH mutants

To determine the binding affinity of some of the selected hGH mutants for the hGHbp, DNA from sequenced clones was transformed into *E. coli* strain 16C9. As described above, this is a non-suppressor strain which terminates translation of protein after the final Phe-191 residue of hGH. Single-stranded DNA was used for these transformations, but double-stranded DNA or even whole phage can be easily electroporated into a non-suppressor strain for expression of free hormone.

Mutants of hGH were prepared from osmotically shocked cells by ammonium sulfate precipitation as described for hGH (Olson et al., *Nature* 293, 408–411 (1981)), and protein concentrations were measured by laser densitomoetry of Coomassie-stained SDS-polyacrylamide gel electrophoresis gels, using hGH as standard (Cunningham and Wells, *Science* 244, 1081–1085 (1989)).

The binding affinity of each mutant was determined by displacement of $^{125}$I hGH as described (Spencer et al., *J. Biol. Chem.* 263, 7862–7867 (1988); Fuh et al., *J. Biol. Chem.* 265, 3111–3115 (1990)), using an anti-receptor monoclonal antibody (Mab263).

The results for a number of hGH mutants, selected by different pathways (FIG. 6) are shown in Table VII. Many of these mutants have a tighter binding affinity for hGHbp than wild-type hGH. The most improved mutant, KSYR, has a binding affinity 5.6 times greater than that of wild-type hGH. The weakest selected mutant, among those assayed was only about 10-fold lower in binding affinity than hGH.

Binding assays may be carried out for mutants selected for hPRLbp-binding.

TABLE VII

Competitive Binding to hGHbp

The selected pool in which each mutant was found is indicated as 1G (first glycine selection), 3G (third glycine selection), 3H (third hGH selection), 3* (third selection, not binding to hPRLbp, but binding to hGHbp). The number of times each mutant occurred among all sequenced clones is shown ( ).

| Mutant | Kd (nM) | Kd(mut)/Kd(hGH) | Pool |
|---|---|---|---|
| KSYR(6) (SEQ ID NO:1) | 0.06 + 0.01 | 0.18 | 1G, 3G |
| RSFR (SEQ ID NO:62) | 0.10 + 0.05 | 0.30 | 3G |
| RAYR (SEQ ID NO:63) | 0.13 + 0.04 | 0.37 | 3* |
| KTYK (2) (SEQ ID NO:64) | 0.16 + 0.04 | 0.47 | H, 3G |
| RYSR(3) (SEQ ID NO:65) | 0.20 + 0.07 | 0.58 | 1G, 3H, 3G |

-continued

| Mutant | Kd (nM) | Kd(mut)/Kd(hGH) | Pool |
|---|---|---|---|
| KAYR(3) (SEQ ID NO:66) | 0.22 + 0.03 | 0.66 | 3G |
| RFFR(2) (SEQ ID NO:67) | 0.26 + 0.05 | 0.76 | 3H |
| KQYR (SEQ ID NO:68) | 0.33 + 0.03 | 1.0 | 3G |
| KEFR = wt(9) (SEQ ID NO:69) | 0.34 + 0.05 | 1.0 | 3H, 3G, 3* |
| RTYH (SEQ ID NO:70) | 0.68 + 0.17 | 2.0 | 3H |
| QRYR (SEQ ID NO:71) | 0.83 + 0.14 | 2.5 | 3* |
| KKYK (SEQ ID NO:72) | 1.1 + 0.4 | 3.2 | 3* |
| RSFS(2) (SEQ ID NO:73) | 1.1 + 0.2 | 3.3 | 3G,* |
| KSNR (SEQ ID NO:74) | 3.1 + 0.4 | 9.2 | 3* |

Additive and non-additive effects on binding

At some residues, substitution of a particular amino acid has essentially the same effect independent of surrounding residues. For example, substitution of F176Y in the background of 172R/174S reduces binding affinity by 2.0-fold (RSFR (SEQ ID NO:62) vs. RSYR (SEQ ID NO:65). Similarly, in the background of 172K/174A the binding affinity of the F176Y mutant (KAYR (SEQ ID NO:66)) is 2.9-fold weaker than the corresponding 176F mutant (KAFR (SEQ ID NO:74); Cunningham and Wells, 1989).

On the other hand, the binding constants determined for several selected mutants of hGH demonstrate non-additive effects of some amino acid substitutions at residues 172, 174, 176, and 178. For example, in the background of 172K/176Y, the substitution E174S results in a mutant (KSYR) (SEQ ID NO: 1) which binds hGHbp 3.7-fold tighter than the corresponding mutant containing E174A (KAYR) (SEQ ID NO:66). However, in the background of 172R/176Y, the effects of these E174 substitutions are reversed. Here, the E174A mutant (RAYR) (SEQ ID NO:63) binds 1.5-fold tighter than the E174S mutant (RSYR) (SEQ ID NO: 65).

Such non-additive effects on binding for substitutions at proximal residues illustrate the utility of protein-phage binding selection as a means of selecting optimized mutants from a library randomized at several positions. In the absence of detailed structural information, without such a selection process, many combinations of substitutions might be tried before finding the optimum mutant.

Example IX

Selection of hGH Variants from a Helix-1 Random Cassette Library of Hormone-Phage Using the methods described in Example VIII, another region of hGH was targeted. This region is involved in binding to the hGHbp and/or hPRLbp, helix 1 residues 10, 14, 18, 21, for random mutagenesis in the phGHam-g3p vector (also known as pS0643; see Example VIII).

The "amber" hGH-g3 construct (called phGHam-g3p) was used because it appears to make the polypeptide, hGH, more accessible for binding. This is supported by data from comparative ELISA assays of monoclonal antibody binding. Phage produced from both pS0132 (S. Bass, R. Greene, J. A. Wells, *Proteins* 8, 309 (1990).) and phGHam-g3 were tested with three antibodies (Medix 2, 1B5.G2, and 5B7.C10) that are known to have binding determinants near the carboxyl-terminus of hGH (B. C. Cunningham, P. Jhurani, P. Ng, J. A. Wells, *Science* 243, 1330 (1989); B. C. Cunningham and J. A. Wells, *Science* 244, 1081 (1989); L. Jin and J. Wells, unpublished results), and one antibody (Medix 1) that recognizes determinants in helices 1 and 3 ((B. C. Cunningham, P. Jhurani, P. Ng, J. A. Wells, *Science* 243, 1330 (1989); B. C. Cunningham and J. A. Wells, *Science* 244, 1081 (1989))). Phagemid particles from phGHam-g3 reacted much more strongly with antibodies Medix 2, 1B5.G2, and 5B7.C10 than did phagemid particles from pS0132. In particular, binding of pS0132 particles was reduced by >2000-fold for both Medix 2 and 5B7.C10 and reduced by >25-fold for 1B5.G2 compared to binding to Medix 1. On the other hand, binding of phGHam-g3 phage was weaker by only about 1.5-fold, 1.2-fold, and 2.3-fold for the Medix 2, 1B5.G2, and 5B7.C10 antibodies, respectively, compared with binding to MEDIX 1.

Construction of the helix 1 library by cassette mutagenesis

Residues in helix 1 that were previously identified by alanine-scanning mutagenesis were mutated (B. C. Cunningham, P. Jhurani, P. Ng, J. A. Wells, *Science* 243, 1330 (1989); B. C. Cunningham and J. A. Wells, *Science* 244, 1081 (1989), 15, 16) to modulate the binding of the extracellular domains of the hGH and/or hPRL receptors (called hGHbp and hPRLbp, respectively). Cassette mutagenesis was carried out essentially as described (J. A. Wells, M. Vasser, D. B. Powers, *Gene* 34, 315 (1985)). This library was constructed by cassette mutagenesis that fully mutated four residues at a time (see Example VIII) which utilized a mutated version of phGHam-g3 into which unique KpnI (at hGH codon 27) and XhoI (at hGH codon 6) restriction sites (underlined below) had been inserted by mutagenesis (T. A. Kunkel, J. D. Roberts, R. A. Zakour, *Methods Enzymol.* 154, 367–382) with the oligonucleotides 5'-GCC TTT GAC A<u>GG TAC C</u>AG GAG TTT G-3' and 5'-CCA ACT ATA CCA CT<u>C TCG AG</u>G TCT ATT CGA TAA C-3', respectively. The later oligo also introduced a +1 frameshift (italicized) to terminate translation from the starting vector and minimize wild-type background in the phagemid library. This starting vector was designated pH0508B. The helix 1 library, which mutated hGH residues 10, 14, 18, 21, was constructed by ligating to the large XhoI-KpnI fragment of pH0508B a cassette made from the complementary oligonucleotides 5'-pTCG AGG CTC NNS GAC AAC GCG NNS CTG CGT GCT NNS CGT CTT NNS CAG CTG GCC TTT GAC ACG TAC-3' and 5'-pGT GTC AAA GGC CAG CTG SNN AAG ACG SNN AGC ACG CAG SNN CGC GTT GTC SNN GAG CC-3'. The KpnI site was destroyed in the junction of the ligation product so that restriction enzyme digestion could be used for analysis of non-mutated background.

The library contained at least $10^7$ independent transformants so that if the library were absolutely random ($10^6$ different combinations of codons) there would be an average of about 10 copies of each possible mutated hGH gene. Restriction analysis using KpnI indicated that at least 80% of helix 1 library constructs contained the inserted cassette.

Binding enrichments of hGH-phage from the libraries was carried out using hGHbp immobilized on oxirane-polyacrylamide beads (Sigma Chemical Co.) as described (Example VIII). Four residues in helix 1 (F10, M14, H18, and H21) were similarly mutated and after 4 and 6 cycles a non-wild-type consensus developed (Table VIII). Position 10 on the hydrophobic face of helix 1 tended to be hydrophobic whereas positions 21 and 18 on the hydrophillic face tended were dominated by Asn; no obvious consensus was evident for position 14 (Table IX).

The binding constants for these mutants of hGH to hGHbp was determined by expressing the free hormone variants in the non-suppressor *E. coli* strain 16C9, purifying the protein, and assaying by competitive displacement of labelled wt-hGH from hGHbp (see Example VIII). As indicated, several mutants bind tighter to hGHbp than does wt-hGH.

TABLE VIII

Selection of hGH Helix 1 Mutants
Variants of hGH (randomly mutated at residues F10, M14, H18, H21) expressed on phagemid particles were selected by binding to hGHbp-beads and eluting with hGH (0.4 mM) buffer followed by glycine (0.2 M, pH 2) buffer (see Example VIII).

| | Gly elution | | |
|---|---|---|---|
| F10 | M14 | H18 | H21 |
| | 4 Cycles | | |
| H | G | N | N |
| A | W | D | N(2) |
| Y | T | V | N |
| I | N | I | N |
| L | N | S | H |
| F | S | F | G |
| | 6 Cycles | | |
| H | G | N | N(6) |
| F | S | F | L |
| | Consensus: | | |
| H | G | N | N |

TABLE IX

Consensus Sequences from the Selected Helix 1 Library
Observed frequency is fraction of all clones sequenced with the indicated amino acid. The nominal frequency is calculated on the basis of NNS 32 codon degeneracy. The maximal enrichment factor varies from 11 to 32 depending upon the nominal frequency value for a given residue. Values of ($K_d$(Ala mut)/$K_d$(wt hGH)) for single alanine mutations were taken from B. C. Cunningham and J. A. Wells, Science 244, 1081 (1989); B. C. Cunningham, D. J. Henner, J. A. Wells, Science 247, 1461 (1990); B. C. Cunningham and J. A. Wells, Proc. Natl. Acad. Sci. USA 88, 3407 (1991).

| Wild type residue | $K_d$(Ala mut) | Selected | Frequency | | |
|---|---|---|---|---|---|
| Enrichment | $K_d$(wt hGH) | residue | | observed | nominal |
| F10 | 5.9 | H | 0.50 | 0.031 | 17 |
| | | F | 0.14 | 0.031 | 5 |
| | | A | 0.14 | 0.062 | 2 |
| M14 | 2.2 | G | 0.50 | 0.062 | 8 |
| | | W | 0.14 | 0.031 | 5 |
| | | N | 0.14 | 0.031 | 5 |
| | | S | 0.14 | 0.093 | 2 |
| H18 | 1.6 | N | 0.50 | 0.031 | 17 |
| | | D | 0.14 | 0.031 | 5 |
| | | F | 0.14 | 0.031 | 5 |
| H21 | 0.33 | N | 0.79 | 0.031 | 26 |
| | | H | 0.07 | 0.031 | 2 |

TABLE X

Binding of Purified hGH Helix 1 Mutants to hGHbp
Competition binding experiments were performed using ($^{125}$I)hGH (wild-type), hGHbp (containing the extracellular receptor domain, residues 1–238), and Mab263 (B. C. Cunningham, P. Jhurani, P. Ng, J. A. Wells, Science 243, 1330 (1989)); The number P indicates the fractional occurrence of each mutant among all the clones sequenced after one or more rounds of selection.

| | Sequence position | | | | | | |
|---|---|---|---|---|---|---|---|
| | 10 | 14 | 18 | 21 | P | $K_d$ (nM)\f($K_d$ mut) | $K_d$(wt hGH)) |
| | H | G | N | N | 0.50 | 0.14 ± 0.04 | 0.42 |
| | A | W | D | N | 0.14 | 0.10 ± 0.03 | 0.30 |
| wt = | F | M | H | H | 0 | 0.34 ± 0.05 | (1) |
| | F | S | F | L | 0.07 | 0.68 ± 0.19 | 2.0 |
| | Y | T | V | N | 0.07 | 0.75 ± 0.19 | 2.2 |
| | L | N | S | H | 0.07 | 0.82 ± 0.20 | 2.4 |
| | I | N | I | N | 0.07 | 1.2 ± 0.31 | 3.4 |

Example X

Selection of hGH Variants from a Helix-4 Random Cassette Library Containing Previously Found Mutations by Enrichment of Hormone-Phage Design of mutant proteins with improved binding properties by iterative selection using hormone-phage It is possible that many individual amino acid substitutions of hGH can be combined to yield cumulatively improved mutants of hGH with respect to binding a particular receptor (B. C. Cunningham, D. J. Henner, J. A. Wells, *Science* 247, 1461 (1990); B. C. Cunningham and J. A. Wells, *Proc. Natl. Acad. Sci. USA* 88, 3407 (1991); H. B. Lowman, B. C. Cunningham, J. A. Wells, *J. Biol. Chem.* 266, in press (1991)).

The helix 4b library was constructed in an attempt to further improve the helix 4 double mutant (E174S/F176Y) selected from the helix 4a library that was found to bind tighter to the hGH receptor (see Example VIII). With the E174S/F176Y hGH mutant as the background starting hormone, residues were mutated that surrounded positions 174 and 176 on the hydrophilic face of helix 4 (R167, D171, T175 and I179).

Construction of the helix 4b library by cassette mutagenesis

Cassette mutagenesis was carried out essentially as described (J. A. Wells, M. Vasser, D. B. Powers, *Gene* 34, 315 (1985)). The helix 4b library, which mutated residues 167, 171, 175 and 179 within the E174S/F176Y background, was constructed using cassette mutagenesis that fully mutated four residues at a time (see Example VIII) and which utilized a mutated version of phGHam-g3 into which unique BstEII and BglII restriction sites had been inserted previously (Example VIII). Into the BstEII-BglII sites of the vector was inserted a cassette made from the complementary oligonucleotides 5'-pG TTA CTC TAC TGC TTC NNS AAG GAC ATG NNS AAG GTC AGC NNS TAC CTG CGC NNS GTG CAG TGC A-3' (SEQ ID NO: 19) and 5'-pGA TCT GCA CTG CAC SNN GCG CAG GTA SNN GCT GAC CTT SNN CAT GTC CTT SNN GAA GCA GTA GA-3' (SEQ ID NO: 80). The BstEII site was eliminated in the ligated cassette. From the helix 4b library, 15 unselected clones were sequenced. Of these, none lacked a cassette insert, 20% were frame-shifted, and 7% had a non-silent mutation.

Results of hGHbp enrichment

Binding enrichments of hGH-phage from the libraries was carried out using hGHbp immobilized on oxirane-polyacrylamide beads (Sigma Chemical Co.) as described (Example VIII). After 6 cycles of binding a reasonably clear consensus developed (Table XI). Interestingly, all positions tended to contain polar residues, notably Ser, Thr and Asn (XIII).

Assay of hGH mutants

The binding constants for some of these mutants of hGH to hGHbp was determined by expressing the free hormone variants in the non-suppressor *E. coli* strain 16C9, purifying the protein, and assaying by competitive displacement of labelled wt-hGH from hGHbp (see Example VIII). As indicated, the binding affinities of several helix-4b mutants for hGHbp were tighter than that of wt-hGH Table XIV).

Receptor-selectivity of hGH variants

Finally, several of the tighter hGHbp binding mutants have been analyzed for their ability to bind to the hPRLbp. The E174S/F176Y mutant binds 200-fold weaker to the hPRLbp than hGH. The E174T/F176Y/R178K and R167N/D171S/E174S/F176Y/I179T mutants each bind >500-fold weaker to the hPRLbp than hGH. Thus, it is possible to use the produce new receptor selective mutants of hGH by phage display technology.

Hormone-phagemid selection identifies the information-content of particular residues Of the 12 residues mutated in three hGH-phagemid libraries (see Examples VIII, IX and X), 4 showed a strong, although not exclusive, conservation of the wild-type residues (K172, T175, F176, and R178). These were residues that when converted to Ala caused the largest disruptions (4- to 60-fold) in binding affinity to the hGHbp. There was a class of 4 other residues (F10, M14, D171, and I179) where Ala substitutions caused weaker effects on binding (2- to 7-fold) and these positions exhibited little wild-type consensus. Finally the other 4 residues (H18, H21, R167, and E174), that promote binding to he hPRLbp but not the hGHbp, did not exhibit any consensus for the wild-type hGH sequence by selection on hGHbp-beads. In fact two residues (E174 and H21), where Ala substitutions enhance binding affinity to the hGHbp by 2- to 4-fold (B. C. Cunningham, P. Jhurani, P. Ng, J. A. Wells, *Science* 243, 1330 (1989); B. C. Cunningham and J. A. Wells, *Science* 244, 1081 (1989); B. C. Cunningham, D. J. Henner, J. A. Wells, *Science* 247, 1461 (1990); B. C. Cunningham and J. A. Wells, *Proc. Natl. Acad. Sci. USA* 88, 3407 (1991)). Thus, the alanine-scanning mutagenesis data correlates reasonably well with the flexibility to substitute each position. In fact, the reduction in binding affinity caused by alanine substitutions (B. C. Cunningham, P. Jhurani, P. Ng, J. A. Wells, *Science* 243, 1330 (1989); B. C. Cunningham and J. A. Wells, *Science* 244, 1081 (1989)), B. C. Cunningham, D. J. Henner, J. A. Wells, *Science* 247, 1461 (1990); B. C. Cunningham and J. A. Wells, *Proc. Natl. Acad. Sci. USA* 88, 3407 (1991)) is a reasonable predictor of the percentage that the wild-type residue is found in the phagemid pool after 3–6 rounds of selection. The alanine-scanning information is useful for targeting side-chains that modulate binding, and the phage selection is appropriate for optimizing them and defining the flexibility of each site (and/or combinations of sites) for substitution. The combination of scanning mutational methods (B. C. Cunningham, P. Jhurani, P. Ng, J. A. Wells, *Science* 243, 1330 (1989); B. C. Cunningham and J. A. Wells, *Science* 244, 1081 (1989)) and phage display is a powerful approach to designing receptor-ligand interfaces and studying molecular evolution in vitro.

Variations on iterative enrichment of hormone-phagemid libraries

In cases where combined mutations in hGH have additive effects on binding affinity to receptor, mutations identified through hormone-phagemid enrichment to improve binding can be combined by simple cutting and ligation of restriction fragments or mutagenesis to yield cumulatively optimized mutants of hGH.

On the other hand, mutations in one region of hGH which optimize receptor binding may be structurally or functionally incompatible with mutations in an overlapping or another region of the molecule. In these cases, hormone phagemid enrichment can be carried out by one of several variations on the iterative enrichment approach: (1) random DNA libraries can be generated in each of two (or perhaps more) regions of the molecule by cassette or another mutagenesis method. Thereafter, a combined library can be created by ligation of restriction fragments from the two DNA libraries; (2) an hGH variant, optimized for binding by mutation in one region of the molecule, can be randomly mutated in a second region of the molecule as in the helix-4b library example; (3) two or more random libraries can be partially selected for improved binding by hormone-phagemid enrichment; after this "roughing-in" of the optimized binding site, the still-partially-diverse libraries can be recombined by ligation of restriction fragments to generate a single library, partially diverse in two or more regions of the molecules, which in turn can be further selected for optimized binding using hormone-phagemid enrichment.

TABLE XI

Mutant Phagemids of hGH Selected from Helix 4b Library after 4 and 6 Cycles of Enrichment Selection of hGH helix 4b mutants (randomly mutated at residues 167, 171, 175, 179), each containing the E1745/F176Y double mutant, by binding to hGHbp-beads and eluting with hGH (0.4 mM) buffer followed by glycine (0.2 M, pH 2) buffer. One mutant (+) contained the spurious mutation R178H.

| R167 | D171 | T175 | I179 |
|---|---|---|---|
| | | 4 Cycles | |
| N | S | T | T |
| K | S | T | T |
| S | N | T | T |
| D | S | T | T |
| D | S | T | T+ |
| D | S | A | T |
| D | S | A | N |
| T | D | T | T |
| N | D | T | N |
| A | N | T | N |
| A | S | T | T |
| | | 6 Cycles | |
| N | S | T | T(2) |
| N | N | T | T |
| N | S | T | Q |
| D | S | S | T |
| E | S | T | I |
| K | S | T | L |
| | | Consensus: | |
| N | S | T | T |
| | | D | N |

TABLE XII

Consensus Sequences from the Selected Library

Observed frequency is fraction of all clones sequenced with the indicated amino acid. The nominal frequency is calculated on the basis of NNS 32 codon degeneracy. The maximal enrichment factor varies from 11 to 16 to 32 depending upon the nominal frequency value for a given residue. Values of ($K_d$(Ala mut)/$K_d$(wt hGH)) for single alanine mutations were taken from the references that follow: B. C. Cunningham, P. Jhurani, P. Ng, J. A. Wells, Science 243, 1330 (1989); B. C. Cunningham and J. A. Wells, Science 244, 1081 (1989); B. C. Cunningham, D. J. Henner, J. A. Wells, Science 247, 1461 (1990); B. C. Cunningham and J. A. Wells, Proc. Natl. Acad. Sci. USA 88, 3407 (1991).

| Wild type residue | $\frac{K_d(Ala\ mut)}{K_d(\text{wt}\ hGH)}$ | Selected residue | Frequency observed | Frequency nominal | Enrichment |
|---|---|---|---|---|---|
| R167 | 0.75 | N | 0.35 | 0.031 | 11 |
| | | D | 0.24 | 0.031 | 8 |
| | | K | 0.12 | 0.031 | 4 |
| | | A | 0.12 | 0.062 | 2 |
| D171 | 7.1 | S | 0.76 | 0.093 | 8 |
| | | N | 0.18 | 0.031 | 6 |
| | | D | 0.12 | 0.031 | 4 |
| T175 | 3.5 | T | 0.88 | 0.062 | 14 |
| | | A | 0.12 | 0.031 | 4 |
| I179 | 2.7 | T | 0.71 | 0.062 | 11 |
| | | N | 0.18 | 0.031 | 6 |

TABLE XIII

Binding of Purified hGH Mutants to hGHbp
Competition binding experiments were performed using ($^{125}$I)hGH (wild-type), hGHbp (containing the extracellular receptor domain, residues 1–238), and Mab263 (11). The number P indicates the fractional occurrence of each mutant among all the clones sequenced after one or more rounds of selection. Note that the helix 4b mutations (*) are in the background of hGH(E174S/F176Y). In the list of helix 4b mutants,, the E174S/F176Y mutant (*), with wt residues at 167, 171, 175, 179, is shown in bold.

| Sequence position * 167 | * 171 | * 175 | * 179 | P | $K_d$(nM) | $\frac{K_d(Ala\ mut)}{K_d(\text{wt}\ hGH)}$ |
|---|---|---|---|---|---|---|
| N | S | T | T | 0.18 | 0.04 ± 0.02 | 0.12 |
| E | S | T | J | 0.06 | 0.04 ± 0.02 | 0.12 |
| K | S | T | L | 0.06 | 0.05 ± 0.03 | 0.16 |
| N | N | T | T | 0.06 | 0.06 ± 0.03 | 0.17 |
| R | D | T | I | 0 | 0.06 ± 0.01 | (0.18) |
| N | S | T | Q | 0.06 | 0.26 ± 0.11 | 0.77 |

Example XI

Assembly of $F_{ab}$ Molecule on the Phagemid Surface

Construction of plasmids

Plasmid pDH 188 contains the DNA encoding the $F_{ab}$ portion of a humanized IgG antibody, called 4D5, that recognizes the HER-2 receptor. This plasmid is contained in *E. coli* strain SR 101, and has been deposited with the ATCC in Rockville, Md.

Figure 16:
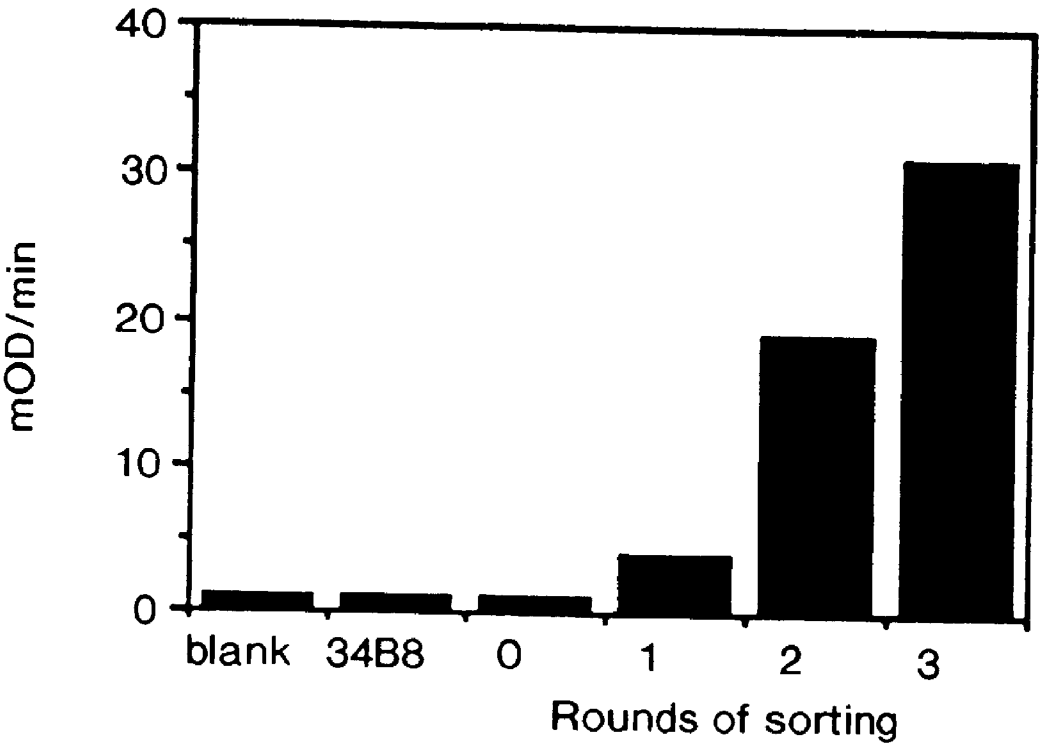
FIG. 16. Schematic diagram of the increase in amount of alkaline phosphatase activity that is detected as a function of the rounds of sorting of phagemid particles.

Briefly, the plasmid was prepared as follows: the starting plasmid was pS0132, containing the alkaline phosphatase promoter as described above. The DNA encoding human growth hormone was excised and, after a series of standard manipulations to make the ends of the plasmid compatible for ligation, the DNA encoding 4D5 was inserted. The 4D5 DNA contains two genes. The first gene encodes the variable and constant regions of the light chain, and contains at its 5' end the DNA encoding the st II signal sequence. The second gene contains four portions: first, at its 5' end is the DNA encoding the st II signal sequence. This is followed by the DNA encoding the variable domain of the heavy chain, which is followed by the DNA encoding the first domain of the heavy chain constant region, which in turn is followed by the DNA encoding the M13gene III. The salient features of this construct are shown in FIGS. 16A and B. The sequence of the DNA encoding 4D5 is shown in FIGS. 11A–11H.

*E. coli* transformation and phage production

Both polyethylene glycol (PEG) and electroporation were used to transform plasmids into SR101 cells. PEG competent cells were prepared and transformed according to the method of Chung and Miller (*Nucleic Acids Res.* 16: 3580 (1988). Cells that were competent for electroporation were prepared, and subsequently transformed via electroporation according to the method of Zabarovsky and Winberg (*Nucleic Acids Res.* 18: 5912 (1990)). After placing the cells in 1 ml of the SOC media (described in Sambrook et al., supra), they were grown for 1 hour at 37° C. with shaking. At this time, the concentration of the cells was determined using light scattering at $OD_{600}$. A titered KO7 phage stock was added to achieve an multiplicity of infection (MOI) of 100, and the phage were allowed to adhere to the cells for 20 minutes at room temperature. This mixture was then diluted into 25 mls of 2 YT broth (described in Sambrook et al., supra) and incubated with shaking at 37° C. overnight. The next day, cells were pelleted by centrifugation at 5000×g for 10 minutes, the supernatant was collected, and the phage particles were precipitated with 0.5M NaCl and 4% PEG (final concentration) at room temperature for 10 minutes. Phage particles were pelleted by centrifugation at 10,000×g for 10 minutes, resuspended in 1 ml of TEN (10 mM Tris, pH 7.6, 1 mM EDTA, and 150 mM NaCl), and stored at 4° C.

Production of antigen coated plates

Aliquots of 0.5 ml from a solution of 0.1 mg/ml of the extra-cellular domain of the HER-2 antigen (ECD) or a solution (control antigen) in 0.5 mg/ml of BSA (control antigen) in 0.1M sodium bicarbonate, pH 8.5 were used to coat one well of a Falcon 12 well tissue culture plate. Once the solution was applied to the wells, the plates were incubated at 4° C. on a rocking platform overnight. The plates were then blocked by removing the initial solution, applying 0.5 ml of blocking buffer (30 mg/ml BSA in 0.1M sodium bicarbonate), and incubating at room temperature for one hour. Finally, the blocking buffer was removed, 1 ml of buffer A (PBS, 0.5% BSA, and 0.05% Tween-20) was added, and the plates were stored up to 10 days at 4° C. before being used for phage selection.

Phage selection process

Approximately $10^9$ phage particles were mixed with a 100-fold excess of KO7 helper phage and 1 ml of buffer A. This mixture was divided into two 0.5 ml aliquots; one of which was applied to ECD coated wells, and the other was applied to BSA coated wells. The plates were incubated at room temperature while shaking for one to three hours, and were then washed three times over a period of 30 minutes with 1 ml aliquots of buffer A. Elution of the phage from the plates was done at room temperature by one of two methods: 1) an initial overnight incubation of 0.025 mg/ml purified Mu4D5 antibody (murine) followed by a 30 minute incubation with 0.4 ml of the acid elution buffer (0.2M glycine, pH 2.1, 0.5% BSA, and 0.05% Tween-20), or 2) an incubation with the acid elution buffer alone. Eluates were then neutralized with 1M Tris base, and a 0.5 ml aliquot of TEN was added. These samples were then propagated, titered, and stored at 4° C.

Phage propagation

Aliquots of eluted phage were added to 0.4 ml of 2 YT broth and mixed with approximately $10^8$ mid-log phase male *E. coli* strain SR101. Phage were allowed to adhere to the cells for 20 minutes at room temperature and then added to 5 ml of 2 YT broth that contained 50 $\mu$g/ml of carbenicillin and 5 $\mu$g/ml of tetracycline. These cells were grown at 37°

C. for 4 to 8 hours until they reached mid-log phase. The $OD_{600}$ was determined, and the cells were superinfected with KO7 helper phage for phage production. Once phage particles were obtained, they were titered in order to determine the number of colony forming units (cfu). This was done by taking aliquots of serial dilutions of a given phage stock, allowing them to infect mid-log phase SR101, and plating on LB plates containing 50 μg/ml carbenicillin.

RIA affinity determination

Figure 13:
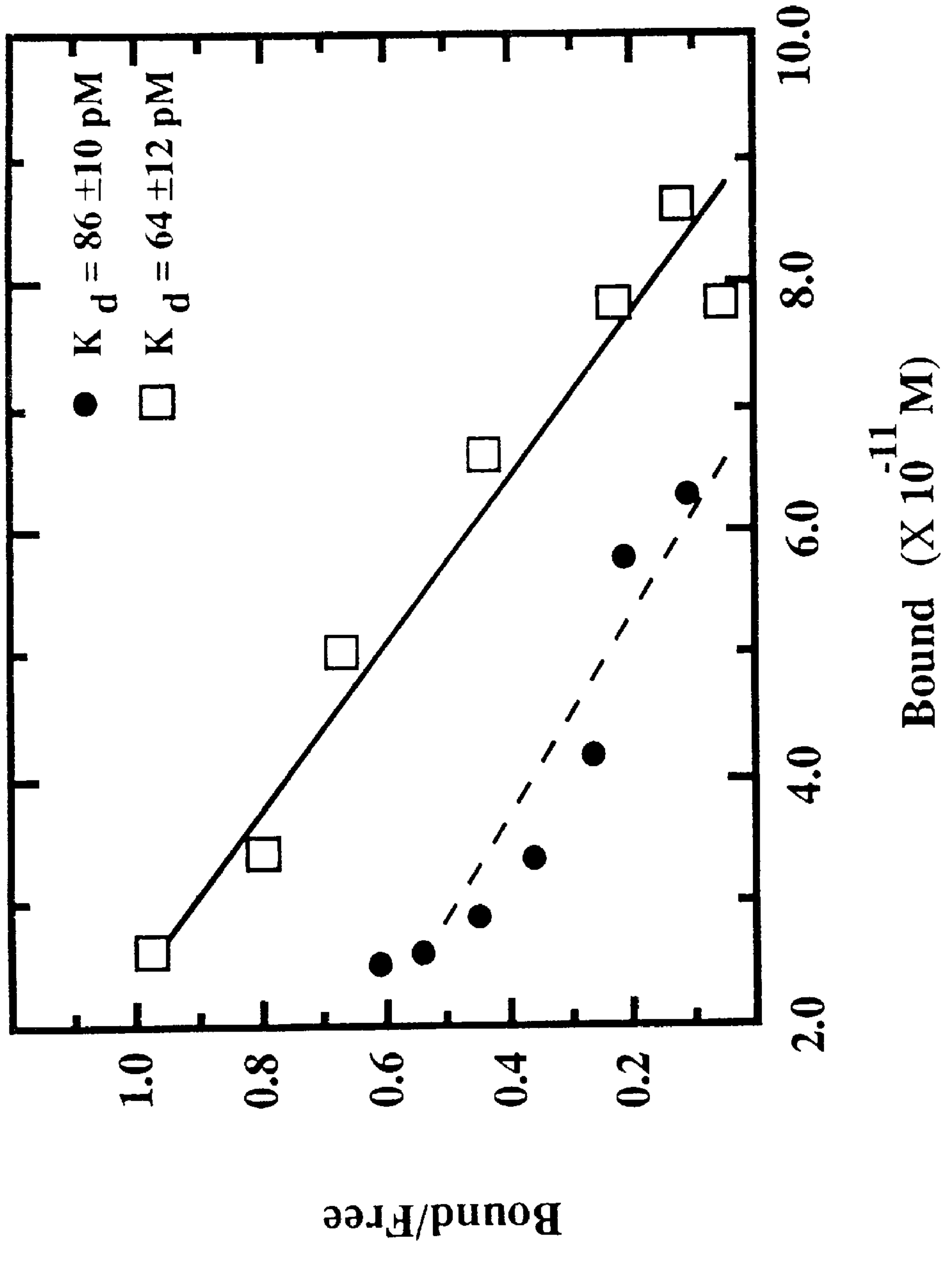
FIG. 13. The Scatchard analysis of the RIA affinity determination described in Experimental Protocols is shown here. The amount of labeled ECD antigen that is bound is shown on the x-axis while the amount that is bound divided by the amount that is free is shown on the y-axis. The slope of the line indicates the $K_a$; the calculated $K_d$ is $1/K_a$.

The affinity of h4D5 $F_{ab}$ fragments and $F_{ab}$ phage for the ECD antigen was determined using a competitive receptor binding RIA (Burt, D. R., *Receptor Binding in Drug Research*. O'Brien, R. A. (Ed.). pp. 3–29, Dekker, New York (1986)). The ECD antigen was labeled with $^{125}$-Iodine using the sequential chloramine-T method (De Larco, J. E. et al., *J. Cell. Physiol.* 109: 143–152 (1981)) which produced a radioactive tracer with a specific activity of 14 μCi/μg and incorporation of 0.47 moles of Iodine per mole of receptor. A series of 0.2 ml solutions containing 0.5 ng (by ELISA) of $F_{ab}$ or $F_{ab}$ phage, 50 nCi of $^{125}$I ECD tracer, and a range of unlabeled ECD amounts (6.4 ng to 3277 ng) were prepared and incubated at room temperature overnight. The labeled ECD-$F_{ab}$ or ECD-$F_{ab}$ phage complex was separated from the unbound labeled antigen by forming an aggregate complex induced by the addition of an anti-human IgG (Fitzgerald 40-GH23) and 6% PEG 8000. The complex was pelleted by centrifugation (15,000×g for 20 minutes) and the amount of labeled ECD (in cpm) was determined by a gamma counter. The dissociation constant ($K_d$) was calculated by employing a modified version of the program LIGAND (Munson, P. and Rothbard, D., *Anal. Biochem.* 107: 220–239 (1980)) which utilizes Scatchard analysis (Scatchard, G., *Ann. N.Y. Acad. Sci.* 51: 660–672 (1949)). The Kd values are shown in FIG. 13.

Competitive cell binding assay

Murine 4D5 antibody was labeled with 125-I to a specific activity of 40–50 μCi/μg using the Iodogen procedure. Solutions containing a constant amount of labeled antibody and increasing amounts of unlabeled variant Fab were prepared and added to near confluent cultures of SK-BR-3 cells grown in 96-well microtiter dishes (final concentration of labeled antibody was 0.1 nM). After an overnight incubation at 4° C., the supernatant was removed, the cells were washed and the cell associated radioactivity was determined in a gamma counter. $K_d$ values were determined by analyzing the data using a modified version of the program LIGAND (Munson, P. and Rothbard, D., supra)

This deposit of plasmid pDH188 ATCC no. 68663 was made under the provisions of the Budapest Treaty on the International Recognition of the Deposit of Microorganisms for the Purpose of Patent Procedure and the Regulations thereunder (Budapest Treaty). This assures maintenance of a viable culture for 30 years from the date of deposit. The organisms will be made available by ATCC under the terms of the Budapest Treaty, and subject to an agreement between Genentech, Inc. and ATCC, which assures permanent and unrestricted availability of the progeny of the cultures to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.14 with particular reference to 886 OG 638).

The assignee of the present application has agreed that if the cultures on deposit should die or be lost or destroyed when cultivated under suitable conditions, they will be promptly replaced on notification with a viable specimen of the same culture. Availability of the deposited cultures is not to be construed as a license to practice the invention in contravention of the rights granted under the authority of any government in accordance with its patent laws.

Example XII

Selection of hGH Variants from Combinations of Helix-1 and Helix-4 Hormone-Phage Variants Construction of additive variants of hGH According to additivity principles (J. A. Wells, *Biochemistry* 29, 8509 (1990)), mutations in different parts of a protein, if they are not mutually interacting, are expected to combine to produce additive changes in the free energy of binding to another molecule (changes are additive in terms of $\Delta\Delta G_{binding}$, or multiplicative in terms of $K_d$=exp(−ΔG/RT)). Thus a mutation producing a 2-fold increase in binding affinity, when combined with a second mutation causing a 3-fold increase, would be predicted to yield a double mutant with a 6-fold increased affinity over the starting variant.

To test whether multiple mutations obtained from hGH-phage selections would produce cumulatively favorable effects on hGHbp (hGH-binding protein; the extracellular domain of the hGH receptor) binding, we combined mutations found in the three tightest-binding variants of hGH from the helix-1 library (Example IX: F10A/M14W/H18D/H21N, F10H/M14G/H18N/H21N, and F10F/M14S/H18F/H21L) with those found in the three tightest binding variants found in the helix-4b library (Example X: R167N/D171S/T175/I179T, R167E/D171S/T175/I179, and R167N/D171N/T175/I179T).

hGH-phagemid double-stranded DNA (dsDNA) from each of the one-helix variants was isolated and digested with the restriction enzymes EcoRI and BstXI. The large fragment from each helix-4b variant was then isolated and ligated with the small fragment from each helix-1 variant to yield the new two-helix variants shown in Table XIV. All of these variants also contained the mutations E174S/F176Y obtained in earlier hGH-phage binding selections (see Example X for details).

Construction of selective combinatorial libraries of hGH

Although additivity principles appear to hold for a number of combinations of mutations, some combinations (e.g. E174S with F176Y) are clearly non-additive (see Examples VIII and X). In order to identify certainty the tightest binding variant with, for example, 4 mutations in helix-1 and 4 mutations in helix-4, one would ideally mutate all 8 residues at once and then sort the pool for the globally tightest binding variant. However, such a pool would consist of 1.1×10$^{12}$ DNA sequences (utilizing NNS codon degeneracy) encoding 2.6×10$^{10}$ different polypeptides. Obtaining a random phagemid library large enough to assure representation of all variants (perhaps 10$^{13}$ transformants) is not practical using current transformation technology.

This difficulty has been addressed using two methods. The first utilizes successive rounds of mutagenesis, taking the tightest binding variant from one library, then mutating other residues to further improve binding (Example X). The second method, the principle of additivity is used to combine the best mutations from two independently sorted libraries to create multiple mutants with improved binding (described above). Here, the possible combinations of mutations at positions 10, 14, 18, 21, 167, 171, 175, and 179 in hGH have been searched by creating combinatorial libraries of random or partially-random mutants. Three different combinatorial libraries of hGH-phagemids were constructed using the pooled phagemids from the helix 1 library (independently sorted for 0, 2, or 4 cycles; Example IX), and the pooled phagemids from the helix-4b library (independently sorted for 0, 2, or 4 cycles; Example X).

hGH-phagemid double-stranded DNA (dsDNA) from each of the one-helix library pools (selected for 0, 2, or 4 rounds) was isolated and digested with the restriction enzymes AccI and BstXI. The large fragment from each helix-1 variant pool was then isolated and ligated with the small fragment from each helix-4b variant pool to yield the three combinatorial libraries pH0707A (unselected helix 1 and helix 4b pools, as described in Examples IX and X), pH0707B (twice-selected helix-1 pool with twice-selected helix-4b pool), and pH0707C (4-times selected helix-1 pool with 4-times selected helix-4b pool). Duplicate ligations were also set up with less DNA and designated as pH0707D, pH0707E, and pH0707F, corresponding to the 0-, 2-, and 4-round starting libraries respectively. All of these variant pools also contained the mutations E174S/F176Y obtained in earlier hGH-phage binding selections (see Example X for details).

Sorting combinatorial libraries of hGH-phage variants

The ligation products pH0707A–F were processed and electro-transformed into XL1-Blue cells as described (Example VIII). Based on colony-forming units (CFU), the number of transformants obtained from each pool was as follows: $2.4\times10^6$ from pH0707A, $1.8\times10^6$ from pH0707B, $1.6\times10^6$ from pH0707C, $8\times10^5$ from pH0707D, $3\times10^5$ from pH0707E, and $4\times10^5$ from pH0707F. hGH-phagemid particles were prepared and selected for hGHbp-binding over 2 to 7 cycles as described in Example VIII.

Rapid sorting of hGH-phagemid libraries increasing the binding time and increasing the wash time and/or concentration with cognate ligand (hGH).

From time-course analysis of wild-type hGH-phagemid binding to immobilized hGHbp, it appears that, of the total hGH-phagemid particles that can be eluted in the final pH 2 wash (see Example VIII for the complete binding and elution protocol), less than 10% are bound after 1 minute of incubation, while greater than 90% are bound after 15 minutes of incubation.

For "rapid-binding selection," phagemid particles from the pH0707B pool (twice-selected for helices 1 and 4 independently) were incubated with immobilized hGHbp for only 1 minute, then washed six times with 1 mL of binding buffer; the hGH-wash step was omitted; and the remaining hGH-phagemid particles were eluted with a pH2 (0.2M glycine in binding buffer) wash. Enrichment of hGH-phagemid particles over non-displaying particles indicated that even with a short binding period and no cognate-ligand (hGH) challenge, hGH-phagemid binding selection sorts tight-binding variants out of a randomized pool.

Assay of hGH mutants

The binding constants for some of these mutants of hGH to hGHbp was determined by expressing the free hormone variants in the non-suppressor *E. coli* strain 16C9 or 34B8, purifying the protein, and assaying by competitive displacement of labelled wt-hGH from hGHbp (see Example VIII) in a radio-immunoprecipitation assay. In Table XIV below, all the variants have $glutamate_{174}$ replaced by $serine_{174}$ and $phenylalanine_{176}$ replaced by $tyrosine_{176}$ (E174S and F1176Y) plus the additional substitutions as indicated at hGH amino acid positions 10, 14, 18, 21, 167, 171, 175 and 179.

TABLE XIV hGH variants from addition of helix-1 and helix-4b mutations

| | Helix 1 | | | | Helix 4 | | | |
|---|---|---|---|---|---|---|---|---|
| wild-type residue: | F10 | M14 | H18 | H21 | R167 | D171 | T175 | I179 |
| Variant | | | | | | | | |
| H0650AD | H | G | N | N | N | S | T | T |
| H0650AE | H | G | N | N | E | S | T | I |
| H0650AF | H | G | N | N | N | N | T | T |
| H0650BD | A | W | D | N | N | S | T | T |
| H0650BE | A | W | D | N | E | S | T | I |
| H0650BF | A | W | D | N | N | N | T | T |
| H0650CD | F | S | F | L | N | S | T | T |
| H0650CD | F | S | F | L | E | S | T | I |
| H0650CD | F | S | F | L | N | N | T | T |

In addition to sorting phagemid libraries for tight-binding protein variants, as measured by equilibrium binding affinity, it was of interest to sort for variants which were altered in either the on-rate ($k_{on}$) or the off-rate ($k_{off}$) of binding to a receptor or other molecule. These rates are related to the equilibrium dissociation constant, $K_d=(k_{off}/k_{on})$. It is expected that certain variants of a particular protein have similar $K_d$'s for binding while having very different $k_{on}$'s and $k_{off}$'s. Conversely, changes in $K_d$ from one variant to another may be due to effects on $k_{on}$, effects on $k_{off}$, or both. The pharmacological properties of a protein may be dependent on binding affinity or on $k_{on}$ or $k_{off}$, depending on the detailed mechanism of action. hGH variants with higher on-rates were identified in order to investigate the effects of changes in $k_{on}$. It is anticipated that the selection could alternatively be weighted toward $k_{off}$ by In Table XV below, hGH variants were selected from combinatorial libraries by the phagemid binding selection process. All hGH variants in Table XV contain two background mutations (E174S/F176Y). hGH-phagemid pools from the libraries pH0707A (Part A), pH0707B and pH0707E (Part B), or pH0707C (Part C) were sorted for 2 to 7 cycles for binding to hGHbp. The number P indicates the fractional occurrence of each variant type among the set of clones sequenced from each pool.

TABLE XV

| | | hGH Variants from Hormone-Phagemid Binding Selection of Combinatorial Libraries. | | | | | | | |
|---|---|---|---|---|---|---|---|---|---|
| | | Helix 1 | | | | Helix 4 | | | |
| wild-type residue: | | F10 | M14 | H18 | H21 | R167 | D171 | T175 | I179 |
| P | Variant | | | | | | | | |
| Part A: | 4 cycles: | | | | | | | | |
| 0.60 | H0714A.1 | H | G | N | N | N | S | T | N |
| 0.40 | H0714A.4 | A | N | D | A | N | N | T | N |
| Part B: | 2 cycles: | | | | | | | | |
| 0.13 | H0712B.1 | F | S | F | G | H | S | T | T |
| 0.13 | H0712B.2 | H | Q | T | S | A | D | N | S |
| 0.13 | H0712B.4 | H | G | N | N | N | A | T | T |
| 0.13 | H0712B.5 | F | S | F | L | S | D | T | T |
| 0.13 | H0712B.6 | A | S | T | N | R | D | T | I |
| 0.13 | H0712B.7 | Q | Y | N | N | H | S | T | T |
| 0.13 | H0712B.8 | W | G | S | S | R | D | T | I |
| 0.13 | H0712E.1 | F | L | S | S | K | N | T | V |
| 0.13 | H0712E.2 | W | N | N | S | H | S | T | T |
| 0.13 | H0712E.3 | A | N | A | S | N | S | T | T |
| 0.13 | H0712E.4 | P | S | D | N | R | D | T | I |
| 0.13 | H0712E.5 | H | G | N | N | N | N | T | S |
| 0.13 | H0712E.6 | F | S | T | G | R | D | T | I |
| 0.13 | H0712E.7 | M | T | S | N | Q | S | T | T |
| 0.13 | H0712E.8 | F | S | F | L | T | S | T | S |
| | 4 cycles: | | | | | | | | |
| 0.17 | H0714B.1 | A | W | D | N | R | D | T | I |
| 0.17 | H0714B.2 | A | W | D | N | H | S | T | N |
| 0.17 | H0714B.3 | M | Q | M | N | N | S | T | T |
| 0.17 | H0714B.4 | H | Y | D | H | R | D | T | T |
| 0.17 | H0714B.5 | L | N | S | H | R | D | T | I |
| 0.17 | H0714B.6 | L | N | S | H | T | S | T | T |
| | 7 cycles: | | | | | | | | |
| 0.57 | H0717B.1 | A | W | D | N | N | A | T | T |
| 0.14 | H0717B.2 | F | S | T | G | R | D | T | I |
| 0.14 | H0717B.6 | A | W | D | N | R | D | T | I |
| 0.14 | H0717B.7 | I | Q | E | H | N | S | T | T |
| 0.50 | H0717E.1 | F | S | L | A | N | S | T | V |
| Part C: | 4 cycles: | | | | | | | | |
| 0.67 | H0714C.2 | F | S | F | L | K | D | T | T |

* = also contained the mutations L15R, K168R.

In Table XVI below, hGH variants were selected from combinatorial libraries by the phagemid binding selected process. All hGH variants in Table XVI contain two background mutations (E174S/F176). The number P is the fractional occurrence of a given variant among all clones sequenced after 4 cycles of rapid-binding selection.

In table XVII below, binding constants were measured by competitive displacement of $^{125}$I-labelled hormone H0650BD or labelled hGH using hGHbp (1–238) and either Mab5 or Mab263. The variant H0650BD appears bind more than 30-fold tighter than wild-type hGH.

TABLE XVI

| | | hGH Variants from RAPID hGHbp Binding Selection of an hGH-Phagemid Combinatorial Library | | | | | | | |
|---|---|---|---|---|---|---|---|---|---|
| | | Helix 1 | | | | Helix 4 | | | |
| wild-type residue: | | F10 | M14 | H18 | H21 | R167 | D171 | T175 | I179 |
| P | Variant | | | | | | | | |
| 0.14 | H07BF4.2 | W | G | S | S | R | D | T | I |
| 0.57 | H07BF4.3 | M | A | D | N | N | S | T | T |
| 0.14 | H07BF4.6 | A | W | D | N | S | S | V | T‡ |
| 0.14 | H07BF4.7 | H | Q | T | S | R | D | T | I |

‡ = also contained the mutation Y176F (wild-type hGH also contains F176).

TABLE XVII

Equilibrium Binding Constants of Selected hGH Variants

| hGH Variant | Kd (variant) / Kd (H0650BD) | Kd (variant) / Kd (hGH) | Kd (pM) |
|---|---|---|---|
| hGH | 32 | -1- | 340 ± 50 |
| H0650BD | -1- | 0.031 | 10 ± 3 |
| H0650BF | 1.5 | 0.045 | 15 ± 5 |
| H0714B.6 | 3.4 | 0.099 | 34 ± 19 |
| H0712B.7 | 7.4 | 0.22 | 74 ± 30 |
| H0712E.2 | 16 | 0.48 | 60 ± 70 |

Example XIII

Selective Enrichment of hGH-Phage Containing a Protease Substrate Sequence Versus Non-Substrate Phage As described in Example I, the plasmid pS0132 contains the gene for hGH fused to the residue Pro198 of the gene III protein with the insertion of an extra glycine residue. This plasmid may be used to produce hGH-phage particles in which the hGH-gene III fusion product is displayed monovalently on the phage surface (Example IV). The fusion protein comprises the entire hGH protein fused to the carboxy terminal domain of gene III via a flexible linker sequence.

To investigate the feasibility of using phage display technology to select favourable substrate sequences for a given proteolytic enzyme, a genetically engineered variant of wild-type subtilisin BPN' was used (Carter, P. et al., Proteins: Structure, function and genetics 6: 240–248 (1989) ). This variant (hereafter referred to as A64SAL subtilisin) contains the following mutations: Ser24Cys, His64Ala, Glu156Ser, Gly169Ala and Tyr217Leu. Since this enzyme lacks the essential catalytic residue His64, its substrate specificity is greatly restricted so that certain histidine-containing substrates are preferentially hyrdrolysed (Carter et al., Science 237: 394–399 (1987)).

Construction of a hGH-substrate-phage vector

The sequence of the linker region in pS0132 was mutated to create a substrate sequence for A64SAL subtilisin, using the oligonucleotide 5'-TTC-GGG-CCC-TTC-GCT-GCT-CAC-TAT-ACG-CGT-CAG-TCG-ACT-GAC-CTG-CCT-3' (SEQ ID NO: 81). This resulted in the introduction of the protein sequence Phe-Gly-Pro-Phe-Ala-His-Tyr-Thr-Arg-Gln-Ser-Thr-Asp (SEQ ID NO: 82) in the linker region between hGH and the carboxy terminal domain of gene III, where the first Phe residue in the above sequence is Phe191 of hGH. The sequence Ala-Ala-His-Tyr-Thr-Arg-Gln (SEQ ID NO: 83) is known to be a good substrate for A64SAL subtilisin (Carter et al (1989), supra). The resulting plasmid was designated pS0640.

Selective enrichment of hGH-substrate-phage

Phagemid particles derived from pS0132 and pS0640 were constructed as described in Example I. In initial experiments, a 10 μl aliquot of each phage pool was separately mixed with 30 μl of oxirane beads (prepared as described in Example II) in 100 μl of buffer comprising 20 mM Tris-HCl pH 8.6 and 2.5M NaCl. The binding and washing steps were performed as described in Example VII. The beads were then resuspended in 400 μl of the same buffer, with or without 50 nM of A64SAL subtilisin. Following incubation for 10 minutes, the supernatants were collected and the phage titres (cfu) measured. Table XVIII shows that approximately 10 times more substrate-containing phagemid particles (pS0640) were eluted in the presence of enzyme than in the absence of enzyme, or than in the case of the non-substrate phagemids (pS0132) in the presence or absence of enzyme. Increasing the enzyme, phagemid or bead concentrations did not improve this ratio.

Improvement of the selective enrichment procedure

In an attempt to decrease the non-specific elution of immobilised phagemids, a tight-binding variant of hGH was introduced in place of the wild-type hGH gene in pS0132 and pS0640. The hGH variant used was as described in Example XI (pH0650bd) and contains the mutations Phe10Ala, Met14Trp, His18Asp, His21Asn, Arg167Asn, Asp171Ser, Glu174Ser, Phe176Tyr and Ile179Thr. This resulted in the construction of two new phagemids: pDM0390 (containing tight-binding hGH and no substrate sequence) and pDM0411 (containing tight-binding hGH and the substrate sequence Ala-Ala-His-Tyr-Thr-Arg-Gln) (SEQ ID NO: 83). The binding washing and elution protocol was also modified as follows:

For binding, COSTAR 12-well tissue culture plates were coated for 16 hours with 0.5 ml/well of 2 ug/ml hGHbp in sodium carbonate buffer at pH 10.0. The plates were then incubated with 1 ml/well of blocking buffer (phosphate buffered saline (PBS) containing 0.1% w/v bovine serum albumin) for 2 hours and washed in an assay buffer containing 10 mM Tris-HCl pH 7.5, 1 mM EDTA and 100 mM NaCl. Phagemids were again prepared as described in Example I: the phage pool was diluted 1:4 in the above assay buffer and 0.5 ml of phage incubated per well for 2 hours.

The plates were washed thoroughly with PBS+0.05% Tween-20 and incubated for 30 minutes with 1 ml of this wash buffer. This washing step was repeated three times.

To elute the phage the plates were incubated for 10 minutes in an elution buffer consisting of 20 mM Tris-HCl pH 8.6+100 mM NaCl, and the phage were eluted with 0.5 ml of the above buffer in either the presence or absence of 500 nM of A64SAL subtilisin.

Table XVIII shows that there was a dramatic increase in the ratio of specifically eluted substrate-phagemid particles compared to the method previously described for pS0640 and pS0132. It is likely that this is due to the fact that the tight-binding hGH mutant has a significantly slower off-rate for binding to hGH binding protein as compared to wild-type hGH.

Colony forming units (cfu) were estimated by plating out 10 μl of 10-fold dilutions of phage on 10 μl spots of *E.coli* XL-1 blue cells on LB agar plates containing 50 μg/ml carbenicillin.

TABLE XVIII

Specific Elution of Substrate-Phagemids by A64SAL Subtilisin

| phagemid | +500 nM A64SAL | no enzyme |
|---|---|---|
| (i) Wild-type hGH gene: binding to hGHbp-oxirane beads | | |
| pS0640 (substrate) | $9 \times 10^6$ cfu/10 μl | $1.5 \times 10^6$ cfu/10 μl |
| pS0132 (non-substrate) | $6 \times 10^5$ cfu/10 μl | $3 \times 10^5$ cfu/10 μl |
| (ii) pH0650bd mutant hGH gene: binding to hGHbp-coated plates | | |
| pDM0411 (substrate) | $1.7 \times 10^5$ cfu/10 μl | $2 \times 10^3$ cfu/10 μl |
| pDM0390 (non-substrate) | $2 \times 10^3$ cfu/10 μl | $1 \times 10^3$ cfu/10 μl |

Example XIV

Identification of Preferred Substrates for A64SAL Subtilisin Using Selective Enrichment of a Library of Substrate Sequences The selective enrichment procedure described in Example XIII was used to identify preferable substrate sequences from a library of random substrate sequences.

Construction of a vector for insertion of randomised substrate cassettes

A vector suitable for introduction of randomized substrate cassettes and subsequent expression of a library of substrate sequences was designed. The starting material was the vector pS0643, described in Example VIII. Site-directed mutagenesis was carried out using the oligonucleotide 5'-AGC-TGT-GGC-TTC-GGG-CCC-GCC-GCC-GC G-TCG-ACT-GGC-GGT-GGC-TCT-3' (SEQ ID NO: 84), which introduces ApaI (GGGCCC) and SalI (GTCGAC) restriction sites between hGH and Gene III. This new construct was designated pDM0253. (The actual sequence of this region of pDM0253 is 5'-AGC-TGT-GGC-TTC-G G G - C C C - G C C - CCC-GCG-TCG-ACT-GGC-GGT-GGC-TCT-3' (SEQ ID NO: 85) where the underlined base substitution is due to a spurious error in the mutagenic oligonucleotide). In addition, the tight-binding hGH variant described in example was introduced by substituting in the appropriate DNA fragment from pDM0411 (Example XIII). The resulting library vector was designated pDM0454.

Preparation of the library cassette vector and insertion of the mutagenic cassette To introduce substrate cassette into the vector in order to generate a substrate library, pDM0454 was digested with ApaI followed by SalI, then precipitated with 13% PEG 8000 and 10 mM $MgCl_2$, washed twice in 70% ethanol and resuspended. This efficiently precipitates the vector but leaves the small Apa-Sal fragment in solution (Paithankar, K. R. and Prasad, K. S. N., Nucleic Acids Research 19: 1346). The product was run on a 1% agarose gel and the ApaI-SalI digested vector excised, purified using a Band-prep kit (Pharmacia) and resuspended for ligation with the mutagenic cassette.

The cassette to be inserted contained a DNA sequence similar to that in the linker region of pS0640 and pDM0411, but with the codons for the histidine and tyrosine residues in the substrate sequence replaced by randomized codons. At each of the randomized positions the codon NNS was substituted in (where N represents all four bases G, A, T and C and S represents the bases G and C) as described in Example VIII. The oligonucleotides used in the mutagenic cassettes were: 5'-C-TTC-GCT-GCT-NNS-NNS-ACC-CGG-CAA-3' (SEQ ID NO:86) (coding strand) and 5'-T-CGA-TTG-CCG-GGT-SNN-SNN-AGC-AGC-GAA-GGG-CC-3' (SEQ ID NO:87) (non-coding strand). This cassette also destroys the SalI site, so that digestion with SalI may be used to reduce the vector background. The oligonucleotides were not phosphorylated before insertion into the Apa-Sal cassette site. Following annealing and ligation, the reaction products were phenol: chloroform extracted, ethanol precipitated and resuspended in water using standard procedures. Initially, no digestion with SalI to reduce the background vector was performed. Approximately 200 ng was electroporated into *E.coli* XL-1 blue cells and a phagemid library was prepared as described in Example VIII.

Selection of highly cleavable substrates from the substrate library

The selection procedure used was identical to that described for pDM0411 and pDM0390 in Example XIII. After each round of selection, the eluted phage were propagated by transducing a fresh culture of XL-1 blue cells and propagating a new phagemid library as described for hGH-phage in Example VIII. The progress of the selection procedure was monitored by measuring eluted phage titres and by sequencing individual clones after each round of selection.

Table XIX shows the successive phage titres for elution in the presence and absence of enzyme after 1, 2 and 3 rounds of selection. Clearly, the ratio of specifically eluted phage: non-specifically eluted phage (ie phage eluted with enzyme-:phage eluted without enzyme) increases dramatically from round 1 to round 3, suggesting that the population of good substrates is indicating with each round of selection.

Sequencing of 10 isolates from the starting library showed them all to consist of the wild-type pDM0464 sequence. This is attributed to the fact that after digestion with ApaI, the SalI site is very close to the end of the DNA fragment, thus leading to low efficiency of digestion. Nevertheless, there are only 400 possible sequences in the library, so this population should still be well represented.

Tables XX and XXI show the sequences of isolates obtained after round 2 and round 3 of selection. After 2 rounds of selection, there was clearly a high incidence of histidine residues. After 3 rounds of selection, each of the 10 clones sequenced had a histidine in the randomised cassette. Note, however, that 2 of the sequences are of pDM0411, which was not present in the starting library and is therefore a contaminant.

Colony forming units (cfu) were estimated by plating out 10 μl of 10-fold dilutions of phage on 10 μl spots of *E.coli* XL-1 blue cells, on LB agar plates containing 50 μg/ml carbenicillin.

TABLE XIX

Titration of initial phage pools and eluted phage from 3 rounds of selective enrichment

| | | |
|---|---|---|
| ROUND 1 | | |
| Starting library: | $3 \times 10^{12}$ cfu/ml | |
| LIBRARY: | +500 nM A64SAL | $4 \times 10^{3}$ cfu/10 μl |
| | no enzyme | $3 \times 10^{3}$ cfu/10 μl |
| pDM0411: | +500 nM A64SAL | $2 \times 10^{6}$ cfu/10 μl |
| (control) | no enzyme | $8 \times 10^{3}$ cfu/10 μl |
| ROUND 2 | | |
| Round 1 library: | $7 \times 10^{12}$ cfu/ml | |
| LIBRARY: | +500 nM A64SAL | $3 \times 10^{4}$ cfu/10 μl |
| | no enzyme | $6 \times 10^{3}$ cfu/10 μl |
| pDM0411: | +500 nM A64SAL | $3 \times 10^{6}$ cfu/10 μl |
| (control) | no enzyme | $1.6 \times 10^{4}$ cfu/10 μl |
| ROUND 3 | | |
| Round 2 library: | $7 \times 10^{11}$ cfu/ml | |
| LIBRARY: | +500 nM A64SAL | $1 \times 10^{5}$ cfu/10 μl |
| | no enzyme | $<10^{3}$ cfu/10 μl |
| pDM0411: | +500 nM A64SAL | $5 \times 10^{6}$ cfu/10 μl |
| (control) | no enzyme | $3 \times 10^{4}$ cfu/10 μl |

TABLE XX

Sequences of eluted phage after 2 rounds of selective enrichment

All protein sequences are of the form AA**TRQ, where * represents a randomized codon. In the table below, the randomized codons and amino acids are underlined and in bold.

After round 2:

| Sequence | | No. of occurrences |
|---|---|---|
| A A *H* *Y* T R Q | (SEQ ID NO:88) | |
| . . . GCT GCT CAC TAC ACC CGG CAA . . . | (SEQ ID NO:89) | 2 |
| A A H M T R Q | (SEQ ID NO:90) | |
| . . . GCT GCT CAC ATG ACC CGG CAA . . . | (SEQ ID NO:91) | 1 |
| A A L H T R Q | (SEQ ID NO:92) | |
| . . . GCT GCT CTC CAC ACC CGG CAA . . . | (SEQ ID NO:93) | 1 |
| A A L H T R Q | (SEQ ID NO:92) | |
| . . . GCT GCT CTG CAC ACC CGG CAA . . . | (SEQ ID NO:94) | 1 |
| A A H T R Q | (SEQ ID NO:95) | |
| . . . GCT GCT CAC ACC CGG CAA . . . | (SEQ ID NO:96) | 1 # |
| A A ? H T R Q | (SEQ ID NO:97) | |
| . . . GCT GCT ? ? ? CAC ACC CGG CAA | (SEQ ID NO:98) | 1 ## |
| . . . wild-type pDM0454 | | 3 |

\# - spurious deletion of 1 codon within the cassette

\## - ambiguous sequence

TABLE XXI

Sequences of eluted phage after 3 rounds of selective enrichment

All protein sequences should be of the form AA**TRQ, where * represents a randomised codon. In the table below, the randomised codons and amino acids are underlined and in bold.

After round 3:

| Sequence | | No. of occurrences |
|---|---|---|
| A A **H** **Y** T R Q | (SEQ ID NO:88) | |
| . . . GCT GCT **CAC** **TAT** ACG CGT CAG . . . | (SEQ ID NO:99) | 2 # |
| A A **L** **H** T R Q | (SEQ ID NO:92) | |
| . . . GCT GCT **CTC** **CAC** ACC CGG CAA . . . | (SEQ ID NO:93) | 2 |
| A A **O** **H** T R Q | (SEQ ID NO:100) | |
| . . . GCT GCT **CAG** **CAC** ACC CGG CAA . . . | (SEQ ID NO:101) | 1 |
| A A **T** **H** T R Q | (SEQ ID NO:102) | |
| . . . GCT GCT **ACG** **CAC** ACC CGG CAA . . . | (SEQ ID NO:103) | 1 |
| A A **H** **S** R Q | (SEQ ID NO:104) | |
| . . . GCT GCT **CAC** **TCC** CGG CAA . . . | (SEQ ID NO:105) | 1 |
| A A **H** **H** T R Q | (SEQ ID NO:106) | |
| . . . GCT GCT **CAT** **CAT** ACC CGG CAA | (SEQ ID NO:107) | 1 ## |
| A A **H** **F** R Q | (SEQ ID NO:108) | |
| . . . GCT GCT **CAC** **TTC** CGG CAA . . . | (SEQ ID NO:109) | 1 |
| A A **H** **T** R Q | (SEQ ID NO:95) | |
| . . . GCT GCT **CAC** **ACC** CGG CAA . . . | (SEQ ID NO:96) | 1 |

TABLE XXI-continued

| Sequences of eluted phage after 3 rounds of selective enrichment | |
|---|---|
| All protein sequences should be of the form AA**TRQ, where * represents a randomised codon. In the table below, the randomised codons and amino acids are underlined and in bold. | |
| After round 3: | |
| Sequence | No. of occurrences |

- contaminating sequence from pDM0411

- contains the "illegal" codon CAT - T should not appear in the 3rd position of a codon.

Example XV

Production of Subtilisin Substrate Peptides

A random polypeptide substrate phage library was constructed by inserting the sequence, Gly-Gly-X-X-X-X-X-Gly-Gly (SEQ ID NO: 110) between the hGH variant and gene III. Here, X represents any of the 20 naturally occurring amino acids ($20\times10^5$ possible protein sequences). To generate this library, suitable vector (pDM0612) was first constructed from the vector pDM0454 (see Example XIII). The short ApaI-SalI cassette from pDM0454 was excised and replaced by a cassette constructed from the complementary oligonucleotides 5'-CTAATGATAATGAATTAATTGATAATGATAATG-3' (SEQ ID NO: 111) and 5'-TCGACATTATCATTATCAATTAATTCATTATCATTAGGGCC-3' (SEQ ID NO:112). This cassette separates the ApaI and SalI sites so that the SalI site is no longer at the end of a fragment and can be cut more efficiently. Furthermore, the cassette contains 8 stop codons and introduces a frameshift between hGH and gene III, so that when library cassettes of substrate peptide fragments are introduced, only plasmids containing a randomized substrate peptide insert will be propagated as hGH-displaying phage. This construct also contains a truncated form of gene III which has been shown (Lowman et al., *Biochemistry* 30, 10832 (1991)) to give better display of hGH as estimated by the binding of monoclonal antibodies with epitopes near the C-terminus.

Substrate polypeptide libraries were constructed by cassette mutagenesis, in a similar manner to the method described by Lowman et al., *Biochemistry* 30, 10832 (1991). The oligonucleotide substrate peptide cassettes were designed to contain randomized sequences of DNA and fixed flanking residues, plus ApaI and SalI compatible cohesive ends. The SalI cohesive end was designed to destroy the SalI site on insertion of the cassette into the vector.

The substrate polypeptide library cassettes were constructed using the oligonucleotides:

5'-CGGTGGTNNSNNSNNSNNSNNSGGTGGTCCTGGC-3' (SEQ ID NO: 113) and

5'-TCGAGCCAGGACCACCSNNSNNSNNSNNSNNACCACCGGGCC-3' (SEQ ID NO:114), where N represents an equal mixture of G, A, T and C, and S represents an equal mixture of G and C bases. This created a peptide sequence Gly-Gly-XXXXX-Gly-Gly (SEQ ID NO:110) between the ApaI and SalI sites of the cassette. The random substrate peptide sequences were flanked with di-glycine linkers (Fontana et al., *Biochem.* 24,1847 (1986)). The two complementary strands of each cassette were annealed by heating the oligonucleotides to 90° C. and cooling slowly to room temperature. The resulting oligonucleotide cassette was ligated together with approximately 1 μg of the ApaI/SalI digested vector (which had previously been purified by gel electrophoresis in 1% TAE agarose) in a (molar) ratio of approximately 1:10 vector:cassette. Following ligation with T4 ligase overnight at room temperature, the ligation product was heated to 65° C. for 10 minutes (to destroy the ligase activity), extracted with phenol:chloroform and precipitated with ethanol in the presence of 0.3M NaOAc and 10 μg carrier tRNA. The resulting product was resuspended in 5 μl $H_2O$ and transformed into *E.coli* XL-1 blue by electroporation as described (Dower et al., *Nuc. Ac. Res.* 16, 6127 (1988)). A control transformation was also carried out with no oligonucleotide cassette present. Transformed cells were used to prepare a phage library by growing them overnight with M13K07 helper phage, added at a suitable concentration to give a multiplicity of infection (moi) of approximately 100.

The library of substrate peptide-phage (containing a total of $4.9\times10^6$ independent transformants) was allowed to bind to the hGHbp coated onto microtiter wells. Elution of substrate phage was performed for 10 minutes at room temperature with the subtilisin mutant BPN' containing the mutations S24C:H64A:E156S:G169A:Y217L (Carter et al., *Proteins: Structure, Function and Genetics* 6, 240 (1989)). This specifically released protease-sensitive phage which were harvested (the "sensitive pool"). The plates were washed in phosphate buffered saline (PBS)+0.01% Tween20 and any phage still bound to the plates were eluted with 50 mM glycine at pH 2.0. (This phage pool contained the "resistant pool"). The phage obtained from selection were propagated by transducing a fresh log phase culture of *E.coli* XL-1 and growing overnight with M13K07 (moi=100). Following transduction for 1 hr at 37° C., the cells were centrifuged and resuspended in 1 ml 2YT, to prevent any active enzyme contaminating the overnight culture. This selection procedure was then repeated. Phage titers were measured at each round of selection: when the phage titres showed that significant enrichment for substrate sequences had occurred, samples were analyzed by DNA sequencing of individual clones. Alternatively, both phage pools and individual clones were analyzed by fusing hGH and substrate to alkaline phosphatase, as described below.

After three rounds of propagation, all clones that were subtilisin sensitive (the sensitive pool) contained a histidine residue someplace in their sequence that tended to be flanked by hydrophobic residues. These sequences are listed in Table XXII. Hydrophobic residues are known to be preferred at the P1 position of subtilisin (Estell et al., *Science* 233, 659–663 (1986)). The requirement for a hydrophobic residue at P3 was previously unknown, and may reflect the possibility that these were cleaved by the His assisting from the P1' position, thus placing them in the P1 position. Sequences containing a Pro at positions P1 to P2' are known to be very poor substrates (see Carter et al., *Proteins: Struct. Funct. Genet* 6, 240–248 (1989) and references therein) and this may explain why no Pro residues were found among substrate sequences. The absence of Cys residues may reflect difficulties in expressing a properly folded hGH-gene III fusion containing an unpaired Cys (hGH contains two disulfides and the carboxyl-terminal domain of gene III contains one).

Clones from the resistant pool exhibited mostly random sequences after three rounds of selection. However, the most common residues in non-substrate sequences were Asn, Ser, Leu and Pro. Ser and Leu codons are two of the three most common in the synthetic DNA used for mutagenesis, and Pro and Asn are poor substrate residues in many of the positions. Only one His containing sequence was isolated, -Gly-Gly-His-Pro-Ser-Glu-Pro-Gly-Gly- (SEQ ID NO:115). However, this cannot be cleaved using the His to assist from the P2 position because subtilisin is unable to cleave Pro-P1 substrates. The His cannot assist from the P1' position because Gly is bad at P1 (Estell et al., *Science* 233. 659–663 (1986)) and Pro is bad at P2'. Thus, protease sensitive sequences resemble good substrates whereas resistant clones resemble poor substrates.

Figure 15:
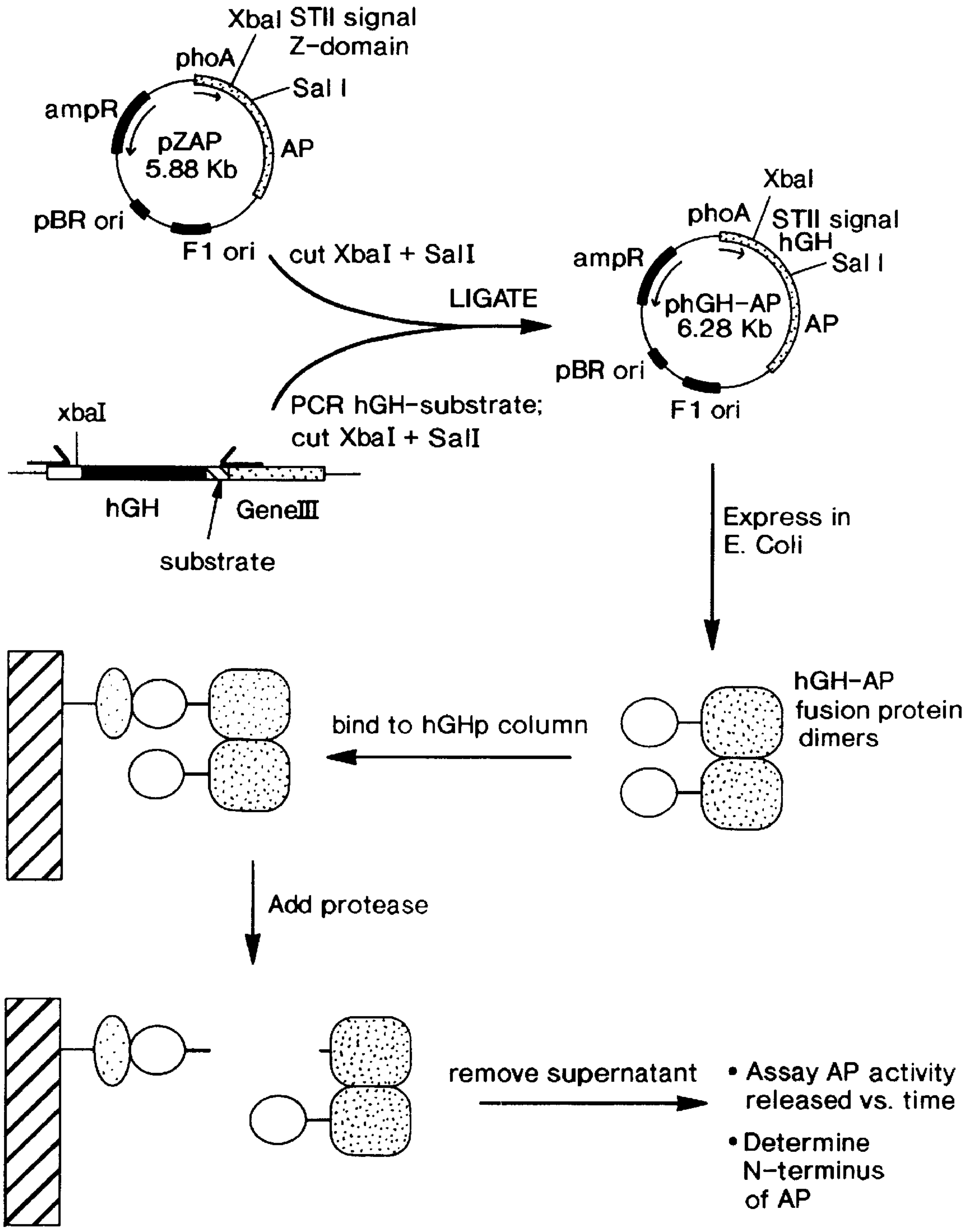
FIG. 15. Schematic diagram of the alkaline phosphatase release assay to measure the rate of hydrolysis of substrate peptide.

The results shown here indicate that the protease selection works to isolate protease sensitive sequences. However, the relative rates of hydrolysis of the substrate, as well as the specific sites of cleavage are unknown. Thus, a simple assay to evaluate these factors was developed. The assay is based on cleaving an hGH-alkaline phosphatase(AP) substrate fusion. This assay is illustrated in FIG. 15. as is construction of the vector. DNA coding for an hGH-peptide substrate sequence was generated using polymerase chain reaction (PCR) and ligated onto the 5'-end of the mature *E.coli* AP coding sequence. The resulting fusion construct was transfected into *E.coli* cells, expressed, secreted and then purified from crude periplasmic preparations by binding to the hGHbp immobilized on acrylamide beads (Bass et al., *Proteins: Struct. Funct. Genet.* 8, 309–314 (1990)). The dimeric fusion protein was presented in large excess over the hGHbp so that it would bind monomerically to the hGHbp. Subtilisin was added and the cleavage rate was measured by the linear release of the AP activity as a function of time. Simple SDS gels followed by Western blotting and protein sequencing allowed determination of the amino-terminus of the released product (see for example Carter et al., *Proteins: Struct. Funct. Genet.* 6, 240–248 (1989)).

This assay is also a convenient method for following the enrichment of substrate versus non-substrate sequences in sequential rounds of protease selection. A substrate-phage library in which only two codons were randomized in the sequence -Ala-Ala-X-X-Thr-Arg-Gln- (SEQ ID NO: 116) was generated and sorted as described in Example XIV. The entire starting substrate-phage pool and pools after each round of selection were PCR-assembled into the hGH-AP substrate assay vector which was transfected into *E. coli.* cells. The fusion protein was expressed and secreted into the periplasm. Release of alkaline phosphatase activity by cleavage of the fusion protein was quantitated as follows. hGHbp-coated oxirane beads were prepared as described previously (Bass et al., *Proteins, Structure, Function and Genetics* 8: 390 (1990)) 90 μl of periplasmic shockate was incubated with 10 μl of bead slurry for one hour at room temperature on an end-over-end mixer. The beads were then pelleted by centrifugation, the supernatant removed and the beads resuspended in 1 ml of 20 mM Tris pH8.6+100 mM NaCl. After washing for 15 minutes, the beads were again pelleted and resuspended in 100 μl of Tris/NaCl buffer containing 500 nM A64 subtilisin. After incubation for 10 minutes, the supernatant was collected and assayed as follows. 100 μl of supernatant was added to 900 μl of 6.6 mM p-nitrophenyl phosphate (PNP) substrate in 600 mM Tris buffer, pH 8.2 at 37° C. The formation of p-nitroaniline (pNA) product was estimated by monitoring the $OD_{410\ nm}$ of this solution over a period of 10 minutes. The results shown in FIG. 16 indicate that for each subsequent round of selection, the amount of AP released increased. The amount of hGH-AP fusion protein activity detected in periplasmic shockate from non transfected 34B8 cells was not detectable above the background rate of PNP hydrolysis. Each pool of hGH-AP substrates were bound to hGHbp-beads and digested with the subtilisin mutant enzyme for 10 min. The amount of AP activity released systematically increased as rounds of selection proceeded, indicating that better substrates were present in the hGH-AP substrate pool derived from the substrate-peptide phage.

TABLE XXII

Sequences from Gly—Gly—XXXXX—Gly—Gly (SEQ ID NO: 110) Library

| 3X sensitive pool | 3X resistant pool |
|---|---|
| F **H** M N V (SEQ ID NO: 117) | S P A Q N (SEQ ID NO: 135) |
| N **H** Y T L (SEQ ID NO: 118) | L S P N M (SEQ ID NO: 136) |
| T **H** Y F L (SEQ ID NO: 119) | M P R T F (SEQ ID NO: 137) |
| K **H** A Y L (SEQ ID NO: 120) | K S M V A (SEQ ID NO: 138) |
| Y **H** M M A (SEQ ID NO: 121) | I N D T L (SEQ ID NO: 139) |
| Y **H** L K M (SEQ ID NO: 122) | D V N K P (SEQ ID NO: 140) |
| T **H** T T Q (SEQ ID NO: 123) | A R R T V (SEQ ID NO: 141) |
| K **H** Y T I (SEQ ID NO: 124) | G N S Q S (SEQ ID NO: 142) |
| Q **H** Y V N (SEQ ID NO: 125) | E W A L L (SEQ ID NO: 143) |
| D G Y **H** L (SEQ ID NO: 126) | I S P L I (SEQ ID NO: 144) |
| T S N **H** I (SEQ ID NO: 127) | A L M D S (SEQ ID NO: 145) |
| L L R **H** T (SEQ ID NO: 128) | T N F S A (SEQ ID NO: 146) |
| A T L **H** L (SEQ ID NO: 129) | T G N N T (SEQ ID NO: 147) |
| A O M **H** M (SEQ ID NO: 130) | S R I S L (SEQ ID NO: 148) |
| T S M **H** T (SEQ ID NO: 131) | N L E L N (SEQ ID NO: 149) |
| Y S L **H** V (SEQ ID NO: 132) | V Y S T N (SEQ ID NO: 150) |
| Y A M **H** F (SEQ ID NO: 133) | **H** P S E P (SEQ ID NO: 151) |
| F R A M **H** (SEQ ID NO: 134) | P S K S Y (SEQ ID NO: 152) |

*—"O" indicates a TAG (amber) stop codon. In XL-1 blue cells (supE), the amber stop is suppressed as glutamate (E)

The foregoing written specification is considered to be sufficient to enable one skilled in the art to practice the invention. The present invention is not to be limited in scope by the cultures deposited, since the deposited embodiments are intended as separate illustrations of certain aspects of the invention and any cultures that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustrations that it represents. Indeed, various modifications of the invention in addition to those shown and described herein will become apparent to those skilled in the art from the foregoing description and fall within the scope of the appended claims.

While the invention has necessarily been described in conjunction with preferred embodiments, one of ordinary skill, after reading the foregoing specification, will be able to effect various changes, substitutions of equivalents, and alterations to the subject matter set forth herein, without departing from the spirit and scope thereof. Hence, the invention can be practiced in ways other than those specifically described herein. It is therefore intended that the protection granted by Letters Patent hereon be limited only by the appended claims and equivalents thereof.

We claim:

1. A method for selecting novel polypeptide substrates comprising:

(a) constructing a replicable expression vector comprising a transcription regulatory element operably linked to a gene fusion, wherein the gene fusion comprises:

(i) a first gene encoding a polypeptide;

(ii) a second gene encoding a substrate peptide; and (iii) a third gene encoding at least a portion of a phage coat protein, wherein the 3' end of the first gene is linked to the 5' end of the second gene, and the 3' end of the second gene is linked to the 5' end of the third gene;

(b) mutating the vector at one or more selected positions within the second gene thereby forming a family of related plasmids encoding substrate peptides;

(c) transforming suitable host cells with the plasmids;

(d) infecting the transformed host cells with a helper phage having a gene encoding the phage coat protein;

(e) culturing the transformed infected host cells under conditions suitable for forming recombinant phagemid particles containing at least a portion of the plasmid and capable of transforming the host, the conditions adjusted so that no more than a minor amount of phagemid particles display more than one copy of the fusion protein on the surface of the particle;

(f) exposing the phagemid particles to a process capable of modifying at least one covalent bond of an amino acid in the substrate peptide of at least a portion of the phagemid particles;

(g) contacting the family of exposed phagemid particles with an affinity molecule, wherein the affinity molecule has affinity for the amino acid residue having the modified covalent bond; and (h) separating the phagemid particles that bind to the affinity molecule from those that do not.

2. The method of claim 1 wherein the process comprises a post-translational covalent bond modifying process selected from the group consisting of a phosphorylation, glycosylation, carboxylation, ADP-ribosylation, methylation, isoprenylation and acylation.

3. The method of claim 2 wherein the process comprises phosphorylation of an amino acid selected from Thr, Ser, and Tyr.

4. The method of claim 2 wherein the affinity molecule is a monoclonal antibody having specificity for the modified amino acid of the process.

5. The method of claim 2 wherein the phagemid particles that bind the affinity molecule are eluted, infected into suitable host cells, and steps (d) through (h) are repeated two or more times.

6. The method of claim 2 wherein the phagemid particles that do not bind to the affinity molecule are infected into suitable host cells and steps (d) through (h) are repeated two or more times.

7. A method for selecting novel polypeptides substrates comprising:

(a) constructing a replicable expression vector comprising a transcription regulatory element operably linked to a gene fusion, wherein the gene fusion comprises:

(i) a first gene encoding a polypeptide;

(ii) a second gene encoding a substrate peptide; and (iii) a third gene encoding at least a portion of a phage coat protein, wherein the 3' end of the first gene is linked to the 5' end of the second gene, and the 3' end of the second gene is linked to the 5' end of the third gene;

(b) mutating the vector at one or more selected positions within the second gene thereby forming a family of related plasmids encoding substrate peptides;

(c) transforming suitable host cells with the plasmids;

(d) infecting the transformed host cells with a helper phage having a gene encoding the phage coat protein;

(e) culturing the transformed infected host cells under conditions suitable for forming recombinant phagemid particles containing at least a portion of the plasmid and capable of transforming the host, the conditions adjusted so that no more than a minor amount of phagemid particles display more than one copy of the fusion protein on the surface of the particle;

(f) exposing the phagemid particles to a process capable of modifying at least one covalent bond of an amino acid residue in the substrate peptide of at least a portion of the phagemid particles;

(g) derivatizing the modified amino acid residue with a substituent capable of binding with an affinity molecule;

(h) contacting the family of exposed derivitized particles with an affinity molecule, wherein the affinity molecule has affinity for the substituent; and (i) separating the phagemid particle that bind to the affinity molecule from those that do not.

8. The method of claim 7 wherein the process comprises a post-translational covalent bond modifying process selected from the group consisting of a phosphorylation, glycosylation, carboxylation, ADP-ribosylation, methylation, isoprenylation and acylation.

9. The method of claim 8 wherein the process comprises phosphorylation of an amino acid selected from Thr, Ser, and Tyr.

10. The method of claim 8 wherein the process comprises glycosylation of an amino acid selected from Asn, Ser, and Thr.

11. The method of claim 8 wherein the phagemid particles that bind the affinity molecule are eluted, infected into suitable host cells, and steps (d) through (h) are repeated two or more times.

12. The method of claim 8 wherein the phagemid particles that do not bind to the affinity molecule are infected into suitable host cells and steps (d) through (h) are repeated two or more times.

13. A method for selecting novel polypeptides substrates, comprising:

(a) constructing a family of replicable expression vectors comprising a transcription regulatory element operably linked to a gene fusion, wherein the gene fusion comprises a gene encoding a substrate peptide and a gene encoding at least a portion of a phage coat protein, wherein the 3' end of the gene encoding the substrate peptide is linked to the 5' end of the gene encoding at least a portion of the phage coat protein;

(b) transforming suitable host cells with the replicable expression vectors;

(c) infecting the transformed host cells with a helper phage having a gene encoding the phage coat protein;

(d) culturing the transformed infected host cells under conditions suitable for forming recombinant phagemid particles containing at least a portion of the replicable expression vector and capable of transforming the host cells, the conditions adjusted so that no more than a minor amount of phagemid particles display more than one copy of the fusion protein on the surface of the particles;

(e) exposing the phagemid particles to a process capable of modifying at least one covalent bond of an amino acid in the substrate peptide of at least a portion of the phagemid particles;

(f) contacting the family of exposed phagemid particles with an affinity molecule, wherein the affinity molecule has affinity for the amino acid residue having the modified covalent bond; and (g) separating the phagemid particles that bind to the affinity molecule from those that do not bind.

14. A method for selecting novel polypeptides substrates, comprising:

(a) constructing a family of replicable expression vectors comprising a transcription regulatory element operably linked to a gene fusion, wherein the gene fusion comprises a gene encoding a substrate peptide and a gene encoding at least a portion of a phage coat protein, wherein the 3' end of the gene encoding the substrate peptide is linked to the 5' end of the gene encoding at least a portion of the phage coat protein;

(b) transforming suitable host cells with the replicable expression vectors;

(c) infecting the transformed host cells with a helper phage having a gene encoding the phage coat protein;

(d) culturing the transformed infected host cells under conditions suitable for forming recombinant phagemid particles containing at least a portion of the replicable expression vector and capable of transforming the host cells, these conditions adjusted so that no more than a minor amount of phagemid particles display more than one copy of the fusion protein on the surface of the particles;

(e) exposing the phagemid particles to a process capable of modifying at least one covalent bond of an amino acid residue in the substrate peptide of at least a portion of the phagemid particles;

(f) derivatizing the modified amino acid residue with a substituent capable of binding with an affinity molecule;

(g) contacting the derivatized particles with an affinity molecule, wherein the affinity molecule has affinity for the substituent; and (h) separating the phagemid particles that bind to the affinity molecule from those that do not bind.

15. A method for selecting novel polypeptides, comprising:

(a) constructing a family of phagemid particles which display different polypeptides fused to at least a portion of a phage coat protein on the surface thereof, wherein no more than a minor amount of phagemid particles display more than one copy of the fusion protein on the surface of the particles;

(b) exposing the phagemid particles to a process capable of modifying at least one covalent bond of an amino acid in the polypeptide of at least a portion of the phagemid particles;

(c) contacting the family of exposed phagemid particles with an affinity molecule, wherein the affinity molecule has affinity for the amino acid residue having the modified covalent bond; and (d) separating the phagemid particles that bind to the affinity molecule from those that do not bind.

16. A method of claim 15, further comprising (e) infecting suitable host cells with the phagemid particles that bind or do not bind to the affinity molecule to produce a second family of phagemid particles and repeating steps (b)–(d).

* * * * *